(12) United States Patent
Birrell

(10) Patent No.: US 11,883,414 B2
(45) Date of Patent: *Jan. 30, 2024

(54) METHODS OF REDUCING MAMMOGRAPHIC BREAST DENSITY AND/OR BREAST CANCER RISK

(71) Applicant: Havah Therapeutics Pty Ltd., Stirling (AU)

(72) Inventor: Stephen Nigel Birrell, Picadilly (AU)

(73) Assignee: Havah Therapeutics Pty Ltd., Stirling (AU)

( * ) Notice: Subject to any disclaimer, the term of this patent is extended or adjusted under 35 U.S.C. 154(b) by 86 days.

This patent is subject to a terminal disclaimer.

(21) Appl. No.: 17/344,052

(22) Filed: Jun. 10, 2021

(65) Prior Publication Data

US 2022/0079954 A1 Mar. 17, 2022

Related U.S. Application Data

(63) Continuation of application No. 16/704,535, filed on Dec. 5, 2019, now Pat. No. 11,040,044, which is a continuation of application No. 16/055,588, filed on Aug. 6, 2018, now Pat. No. 10,525,063, which is a continuation of application No. 15/520,278, filed as application No. PCT/AU2015/000633 on Oct. 22, 2015, now Pat. No. 10,064,874.

(60) Provisional application No. 62/067,297, filed on Oct. 22, 2014.

(51) Int. Cl.
| | | |
|---|---|---|
| A61K 31/568 | (2006.01) | |
| A61K 45/06 | (2006.01) | |
| A61K 31/4196 | (2006.01) | |
| A61K 9/00 | (2006.01) | |
| A61K 31/569 | (2006.01) | |

(52) U.S. Cl.
CPC .......... *A61K 31/568* (2013.01); *A61K 9/0024* (2013.01); *A61K 9/0053* (2013.01); *A61K 31/4196* (2013.01); *A61K 31/569* (2013.01); *A61K 45/06* (2013.01)

(58) Field of Classification Search
CPC .. A61K 31/568; A61K 45/00; A61K 31/4196; A61K 9/00; A61K 31/569
See application file for complete search history.

(56) References Cited

U.S. PATENT DOCUMENTS

| | | | |
|---|---|---|---|
| 4,147,783 | A | 4/1979 | Van Der Vies |
| 4,412,993 | A | 11/1983 | Sokolowski |
| 5,824,286 | A | 10/1998 | Hodgen |
| 5,861,387 | A | 1/1999 | Labrie |
| 6,200,593 | B1 | 3/2001 | Place |
| 6,241,529 | B1 | 6/2001 | Place |
| 6,569,896 | B2 | 5/2003 | Dalton |
| 6,593,313 | B2 | 7/2003 | Place |
| 6,696,432 | B1 | 2/2004 | Elliesen |
| 6,995,284 | B2 | 2/2006 | Dalton |
| 7,772,433 | B2 | 8/2010 | Dalton |
| 8,003,689 | B2 | 8/2011 | Veverka |
| 8,008,348 | B2 | 8/2011 | Steiner |
| 8,980,569 | B2 | 3/2015 | Weinberg |
| 8,980,840 | B2 | 3/2015 | Truitt, III |
| 9,150,501 | B2 | 10/2015 | Dalton |
| 9,168,302 | B2 | 10/2015 | Birrell |
| 9,351,977 | B2 | 5/2016 | Birrell |
| 9,616,072 | B2 | 4/2017 | Birrell |
| 10,064,874 | B2 | 9/2018 | Birrell |
| 10,471,073 | B2 | 11/2019 | Birrell |
| 10,525,063 | B2 | 1/2020 | Birrell |
| 11,040,044 | B2 | 6/2021 | Birrell |
| 11,524,014 | B2 | 12/2022 | Birrell |
| 2003/0087885 | A1 | 5/2003 | Masini-Eteve |
| 2004/0191311 | A1 | 9/2004 | Liang |
| 2005/0032750 | A1 | 2/2005 | Steiner |
| 2005/0176692 | A1 | 8/2005 | Amory |
| 2005/0233970 | A1 | 10/2005 | Garnick |
| 2006/0069067 | A1 | 3/2006 | Bhatnagar |

(Continued)

FOREIGN PATENT DOCUMENTS

| | | |
|---|---|---|
| WO | 1990010462 | 9/1990 |
| WO | 1994016709 | 8/1994 |

(Continued)

OTHER PUBLICATIONS

Park et al. Annals of Oncology 22: 1755-1762, (2011).*
Glaser, R. et al., "Testosterone and Breast Cancer Prevention", Maturitas, 82(3), 290-294, (2015).
Glaser, R. et al., "Testosterone Implants in Women: Pharmacological Dosing for a Physiologic Effect," Maturitas, 74:179-184, (2013).
Glaser, R. et al., "Testosterone Therapy in Women: Myths and Misconceptions", Maturitas, 74:230-234, (2013).
Golatta, M. et al., "Evaluation of Virtual Touch Tissue Imaging Quantification, a New Shear Wave Velocity Imaging Method, for Breast Lesion Assessment by Ultrasound", Biomed. Res. Int., 2014:960262, 7 pages, (2014).
Goss, P. et al., "Anastrozole: A New Selective Nonsteroidal Aromatase Inhibitor", Oncology, 11(11):Abstract only (Complete copy from www.cancernetwork.com), 8 pages, (1997).
Goss, P. et al., "Chemoprevention with Aromatase Inhibitors-Trial Strategies", J. Steroid Biochem. Mol. Biol., 79:143-149, (2001).

(Continued)

*Primary Examiner* — Shirley V Gembeh
(74) *Attorney, Agent, or Firm* — Cynthia Hathaway; Brock Levin

(57) ABSTRACT

The present disclosure is directed to generally methods and/or compositions for treating mammographic breast density and/or breast stiffness in a patient in need thereof, such as a pre-menopausal, a peri-menopausal or a post-menopausal patient, comprising the administration of an effective amount of androgenic agent and an effective amount of an aromatase inhibitor. The present disclosure is also directed to methods and/or compositions for reducing breast pain. The present disclosure is also directed to method and/or compositions for reducing elasticity and/or decreasing mechano-transduction on the genome of breast cells. The present disclosure is also directed to methods and/or compositions for stabilizing and/or increasing the levels of androgen receptor expression in breast tissue.

9 Claims, 34 Drawing Sheets

(56) References Cited

U.S. PATENT DOCUMENTS

| | | |
|---|---|---|
| 2007/0066568 A1 | 3/2007 | Dalton |
| 2009/0264534 A1 | 10/2009 | Dalton |
| 2010/0144687 A1 | 6/2010 | Glaser |
| 2014/0018433 A1 | 1/2014 | Dalton |
| 2014/0080905 A1 | 3/2014 | Dalton |
| 2014/0162991 A1 | 6/2014 | Glaser |
| 2022/0088035 A1 | 3/2022 | Birrell |
| 2023/0088473 A1 | 3/2023 | Birrell |

FOREIGN PATENT DOCUMENTS

| | | |
|---|---|---|
| WO | 2000069467 | 11/2000 |
| WO | 2001087334 | 11/2001 |
| WO | 2002009721 | 2/2002 |
| WO | 2002030355 | 4/2002 |
| WO | 2004034978 | 4/2004 |
| WO | 2004035739 | 4/2004 |
| WO | 2004064747 | 8/2004 |
| WO | 2005011705 | 2/2005 |
| WO | 2005037263 | 4/2005 |
| WO | 2005070434 | 8/2005 |
| WO | 2007045027 | 4/2007 |
| WO | 2008127717 | 10/2008 |
| WO | 2009036566 | 3/2009 |
| WO | 2010065358 A | 6/2010 |
| WO | 2010118287 | 10/2010 |
| WO | 2013067170 | 5/2013 |
| WO | 2016061615 | 4/2016 |
| WO | 2017066827 | 4/2017 |
| WO | 2020243777 | 12/2020 |

OTHER PUBLICATIONS

Gunter, M. et al., "Circulating Adipokines and Inflammatory Markers and Postmenopausal Breast Cancer Risk", J. Natl. Cancer Inst., 107(9), 10 pages, (2015).

Haagensen, D. et al., "Breast Gross Cystic Disease Fluid Analysis. I. Isolation and Radioimmunoassay for a Major Component Protein", J. Natl. Cancer Inst., 62(2):239-247, (1979).

Hodgson, M. et al., "Reduced Androgen Receptor Expression Accelerates the Onset of ERBB2 Induced Breast Tumors in Female Mice", PLOS One, 8(4) e60455, 12 pages, (2013).

Hubalek, M, et al., "Does Obesity Interfere With Anastrozole Treatment? Positive Association Between Body Mass Index and Anastrozole Plasma Levels", Clin. Breast Cancer, 14(4), 6 pages, (2014).

International Application No. PCT/AU2006/001539; International Search Report and Written Opinion of the International Searching Authority, dated Jan. 3, 2007; 5 pages.

International Application No. PCT/AU2015/000633; International Preliminary Report on Patentability, dated Apr. 25, 2017; 6 pages.

International Application No. PCT/AU2015/000633; International Search Report and Written Opinion of the International Searching Authority, dated Dec. 16, 2015; 11 pages.

International Application No. PCT/AU2016/050973; International Search Report and Written Opinion of the International Searching Authority, dated Nov. 22, 2016; 9 pages.

International Application No. PCT/AU2020/050562; International Search Report and Written Opinion of the International Searching Authority, dated Sep. 2, 2020; 15 pages.

Iobagiu, C. et al., "Loss of Heterozygosity in Tumor Tissue in Hormonal Receptor Genesis Associated with Poor Prognostic Criteria in Breast Cancer", Cancer Genet., 208(4):135-142, (2015).

Ironside, A. et al., "Stromal Characteristics May Hold the Key to Mammographic Density: The Evidence to Date", Oncotarget, 13 pages, (2016).

Japanese Application No. 2008-535845; Office Action with English Translation; dated Jul. 3, 2012; 7 pages.

Javed, A. "Development of the Human Breast", Semin. Plast. Surg., 27(1):5-12 (2013).

Kass, L. et al., "Mammary Epithelial Cell: Influence of Extracellular Matrix Composition and Organization During Development and Tumorigenesis", Int. J. Biochem. Cell Biol., 39(11):1987-1994, (2007).

Li, C. et al., "Effect of Depo-Medroxyprogesterone Acetate on Breast Cancer Risk Among Women 20 to 44 Years of Age", Cancer Res., 72(8):2028-2035, (2012).

Li, X. et al., "Determination of the Elasticity of Breast Tissue During the Menstrual Cycle Using Real-Time Shear Wave Elastography", Ultrasound Med. Biol., 41(12):3140-3147, (2015).

Lienart, V. et al., "Effect of Preventive Hormonal Therapy on Breast Density: A Systematic Qualitative Review", Scientific World Journal, 2014:942386, 24 pages, (2014).

Lillie, E. et al., "Polymorphism in the Androgen Receptor and Mammographic Density in Women Taking and Not Taking Estrogen and Progestin Therapy", Cancer Res., 64(4):1237-1241, (2004).

Linton, L. et al., "Associations of Serum Levels of Sex Hormones in Follicular and Luteal Phases of the Menstrual Cycle with Breast Tissue Characteristics in Young Women", PLOS One, 11(10):e0163865, 14 pages, (2016).

Lombard, J. et al., "Aromatase Inhibitor Induced Musculoskelelal Syndrome: A Significant Problem with Limited Treatment Options", Support Care Cancer, doi:10.1007/s00520-015-3001-5, 8 pages, (2015).

Loprinzi, C., "Randomized Double-Blind Placebo Controlled Study of Testosterone in the Adjuvant Treatment of Postmenopausal Women with Aromatase Inhibitor Induced Arthralgias", Alliance for Clinical Trials in Oncology, Study A221102, NCI Version Date (Update #6) Sep. 10, 2018; 130 pages.

Lowdon, R. et al., "Regulatory Network Decoded from Epigenomes of Surface Ectoderm-Derived Cell Types", Nat. Commun., 5:5442, 27 pages, (2014).

Lundin, K. et al., "Androgen Receptor Genotypes Predict Response to Endocrine Treatment in Breast Cancer Patients", Br. J. Cancer, 105(11):1676-1683, (2011).

Miller, WR et al., "The Therapeutic Potential of Aromatase Inhibitors", Expert Opin. Invest. Drugs, 12(3):337-351, (2003).

Mocellin, S. et al., "Breast Cancer Chemoprevention: A Network Meta-Analysis of Randomized Controlled Trials", J. Natl. Cancer Inst., 108(2), 9 pages, (2016).

Mockus, M. et al., "First Pregnancy Characteristics, Postmenopausal Breast Density, and Salivary Sex Hormone Levels in a Population at High Risk for Breast Cancer", BBA Clin., 3:189-195, (2015).

Moshina, N. et al., "Mammographic Density and Histopathologic Characteristics of Screen-Detected Tumors in the Norwegian Breast Cancer Screening Program", Acta Radiol. Open, 4(9), 4 pages, (2015).

Mousa, N. et al., "Aromatase Inhibitors and Mammographic Breast Density in Postmenopausal Women Receiving Hormone Therapy" Menopause, 15(5):875-84, (2008).

Narayanan, R. et al., "Selective Androgen Receptor Modulators (SARMs) Negatively Regulate Triple-Negative Breast Cancer Growth and Epithelial:Mesenchymal Stem Cell Signaling", PLOS One, 9(7):e103202, 12 pages, (2014).

Ng, K-H et al., "Vision 20/20: Mammographic Breast Density and its Clinical Applications", Med. Phys., 42 (12):7059-7077, (2015).

Niravath, P., "Aromatase Inhibitor-Induced Arthralgia: A Review", Ann. Oncol., 24(6):1443-1449, (2013).

Ochnik, A. et al., "Antiandrogenic Actions of Medroxyprogesterone Acetate on Epithelial Cells Within Normal Human Breast Tissues Cultured Ex Vivo", Menopause, 21(1):79-88, (2014).

Olsen, N. et al., "Evidence that Androgens Modulate Human Thymic T Cell Output", J. Investig. Med., 59(1):32-35, (2011).

Ouimet-Oliva, D. et al., "Effect of Danazol on the Radiographic Density of Breast Parenchyma", Medline, XP002321074, Nov. 17, 2004; 1 page.

Ozkaya, E. et al., "Is Hyperandrogenemia Protective for Fibrocystic Breast Disease in PCOS?", Gynecol. Endocrinol., 28(6):468-471, (2012).

Park, S. et al., "Androgen Receptor Expression is Significantly Associated With Better Outcomes in Estrogen Receptor-Positive Breast Cancers", Annals of Oncology, 22:1755-1762, (2011).

(56) References Cited

OTHER PUBLICATIONS

Parsanezhad, M. et al., "A Randomized, Controlled Clinical Trial Comparing the Effects of Aromatase Inhibitor (Letrozole) and Gonadotropin-Releasing Hormone Agonist (Triptorelin) on Uterine Leiomyoma vol. and Hormonal Status", Fertil. Steril., 93(1):192-198, (2010).
Peres, J., "Why Is Breast Cancer Chemoprevention Such a Hard Sell?", J. Natl. Cancer Inst., 106(5):4-6, (2014).
Pettersson, A. et al., "Mammographic Density Phenotypes and Risk of Breast Cancer: A Meta-Analysis", J. Natl. Cancer Inst., 106(5):dju078, 11 pages, (2014).
Pike, MC et al., "Mammographic Density, MRI Background Parenchymal Enhancement and Breast Cancer Risk", Ann. Oncol., 24(Suppl 8):viii37-viii41, (2013).
Plourde, P. et al., "Arimidex®: A Potent and Selective Fourth-Generation Aromatase Inhibitor", Breast Cancer Res. Treat., 30:103-111, (1994).
Priority document AU 2005905768, dated Oct. 19, 2005, for International Application No. PCT/AU2006/001539, publicly made available on WIPO on Feb. 26, 2007; 23 pages.
Priority document U.S. Appl. No. 60/732,662, dated Nov. 3, 2005, for International Application No. PCT/AU2006/001539, publicly made available on WIPO on Feb. 26, 2007; 21 pages.
Priority document U.S. Appl. No. 60/798,308, dated May 8, 2006, for International Application No. PCT/AU2006/001539, publicly made available on WIPO on Feb. 26, 2007; 33 pages.
Abu Hashim, H. et al., "Randomized Comparison of Superovulation with Letrozole vs. Clomiphene Citrate in an IUI Program for Women with Recently Surgically Treated Minimal to Mild Endometriosis", Acta. Obstet. Gynecol. Scand., 91(3):338-345, (2012).
Alexander, H. et al., "Proteomic Analysis to Identify Breast Cancer Biomarkers in Nipple Aspirate Fluid", Clin. Cancer Res., 10(22):7500-7510, (2004).
Arendt, L. et al., "Working Stiff: How Obesity Boosts Cancer Risk", Sci. Transl. Med., 7(301), 301fs34, 3 pages, (2015).
Ashbeck, E. et al., "Benign Breast Biopsy Diagnosis and Subsequent Risk of Breast Cancer", Cancer Epidemiol Biomarkers Prev., 16(3):467-472, (2007).
Baker, E. et al., "Cancer Cell Stiffness: Integrated Roles of Three-Dimensional Matrix Stiffness and Transforming Potential", Biophys J., 99(7):2048-57, (2010).
Beattie, M. et al., "Endogenous Sex Hormones, Breast Cancer Risk, and Tamoxifen Response: An Ancillary Study in the NSABP Breast Cancer Prevention Trial (P-)", J. Natl. Cancer Inst., 98(2):110-115, (2006).
Beckmann, K. et al., "Impact of Hormone Replacement Therapy use on Mammographic Screening Outcomes", Cancer Causes Control, 24(7):1417-1426, (2013).
Beer, B. et al., "Development and Validation of a Liquid Chromatography-Tandem Mass Spectrometry Method for the Simultaneous Quantification of Tamoxifen, Anastrozole, and Letrozole in Human Plasma and its Application to a Clinical Study", Anal. Bioanal. Chem., 398(4):1791-1800, (2010).
Bhasin, S. et al., "Selective Androgen Receptor Modulators (SARMs) as Function Promoting Therapies", Curr. Opin. Clin. Nutr. Metab. Care, 12(3):232-240, (2009).
Birrell, S. et al., "Combined Hormone Replacement Therapy and Breast Cancer", Expert Report, 34 pages, dated Apr. 1, 2008.
Birrell, S. et al., "Disruption of Androgen Receptor Signaling by Synthetic Progestins May Increase Risk of Developing Breast Cancer", Faseb J., 21(10):2285-2293, (2007).
Bolduc, C. et al., "Transcriptomic Characterization of the Long-Term Dihydrotestosterone Effects in Adipose Tissue", Obesity, 15(5):1107-1132, (2007).
Boyd, N. et al., "Breast-Tissue Composition and Other Risk Factors for Breast Cancer in Young Women: A Cross-Sectional Study", Lancet Oncol., 10(6), 569-580, (2009).
Boyd, N. et al., "Evidence That Breast Tissue Stiffness Is Associated with Risk of Breast Cancer", PLOS One, 9(7): e100937, 8 pages, (2014).
Boyd, N. et al., "Mammographic Densities and Breast Cancer Risk", Breast Dis., 10(3,4):113-126, (1998).
Boyd, N. et al., "Mammographic Density, Response to Hormones, and Breast Cancer Risk", J. Clin. Oncol., 29 (22):2985-2992, (2011).
Braunstein, G., "Safety of Testosterone Treatment in Postmenopausal Women", Fertil. Steril., 88(1):1-17, (2007).
Byrne, C. et al., "Mammographic Density Change With Estrogen and Progestin Therapy and Breast Cancer Risk", J. Natl. Cancer Inst., 109(9):djx001, 7 pages, (2017).
Chen, R. et al., "Antiproliferative Effects of Anastrozole on MCF-7 Human Breast Cancer Cells In Vitro are Significantly Enhanced by Combined Treatment with Testosterone Undecanoate", Mol. Med. Rep., 12(1):769-775, (2015).
Chiu, S. et al., "Effect of Baseline Breast Density on Breast Cancer Incidence, Stage, Mortality, and Screening Parameters: 25-Year Follow-up of a Swedish Mammographic Screening", Cancer Epidemiol. Biomarkers Prev., 19 (5):1219-1228, (2010).
Chlebowski, R. et al., "Influence of Estrogen Plus Progestin on Breast Cancer and Mammography in Healthy Postmenopausal Women: The Women's Health Initiative Randomized Trial", JAMA, 289(24):3243-3253, (2003).
Cilotti, A. et al., "Male Osteoporosis and Androgenic Therapy: From Testosterone to SARMs", Clin. Cases Miner. Bone Metab., 6(3):229-233, (2009).
Crandall, C. et al., "Breast Tenderness After Initiation of Conjugated Equine Estrogens and Mammographic Density Change", Breast Cancer Res. Treat., 131(3):969-979, (2012).
Cuzick, J. et al., "Impact of Preventive Therapy on the Risk of Breast Cancer Among Women with Benign Breast Disease", Breast, 24:S51-S55, (2015).
Cuzick, J. et al., "Tamoxifen-Induced Reduction in Mammographic Density and Breast Cancer Risk Reduction: A Nested Case-Control Study", J. Natl. Cancer Inst., 103(9):744-752, (2011).
Dalton, J. et al., "The Selective Androgen Receptor Modulator GTx-024 (Enobosarm) Improves Lean Body Mass and Physical Function in Healthy Elderly Men and Postmenopausal Women: Results of a Double-Blind, Placebo-Controlled Phase II Trial", J. Cachexia Sarcopenia Muscle, 2(3):153-161, (2011).
Davis, S. et al., "Androgen Treatment of Postmenopausal Women", J. Steroid Biochem. Mol. Biol., 142:107-114, (2014).
Defilippis, R. et al., "CD36 Repression Activates a Multicellular Stromal Program Shared by High Mammographic Density and Tumor Tissues", Cancer Discov., 2(9):826-839, (2012).
Defilippis, R. et al., "Stress Signaling from Human Mammary Epithelial Cells Contributes to Phenotypes of Mammographic Density", Cancer Res., 74(18):5032-5044, (2014).
Dilley, W. et al., "Androgen Stimulation of Gross Cystic Disease Fluid Protein and Carcinoembryonic Antigen in Patients with Metastatic Breast Carcinoma", J. Natl. Cancer Inst., 70(1):69-74, (1983).
Dixon, JM et al., "Risk of Breast Cancer in Women with Palpable Breast Cysts: A Prospective Study", Lancet, 353:1742-1745, (1999).
Duhan, N. et al., "Role of the Aromatase Inhibitor Letrozole in the Management of Uterine Leiomyomas in Premenopausal Women", Eur. J. Obstet. Gynecol. Reprod. Biol., 171:329-332, (2013).
Eigeliene, N. et al., "Androgens Inhibit the Stimulatory Action of 17beta-Estradiol on Normal Human Breast Tissue in Explant Cultures", J. Clin. Endocrinol. Metab., 97(7), 12 pages, (2012).
European Patent No. 1945224; Extended European Search Report and Written Opinion, dated Aug. 24, 2009; 7 pages.
European Patent No. 3209301; Extended European Search Report and Written Opinion, dated Feb. 12, 2018; 8 pages.
Freer, P., "Mammographic Breast Density: Impact on Breast Cancer Risk and Implications for Screening", RadioGraphics, 35(2)302-315, (2015).
Gao, W. et al., "Expanding the Therapeutic use of Androgens via Selective Androgen Receptor Modulators (SARMs)", Drug Discov. Today, 12(5-6):241-248, (2007).

(56) References Cited

OTHER PUBLICATIONS

Gao, W. et al., "Ockham's Razor and Selective Androgen Receptor Modulators (SARMs): Are We Overlooking the Role of 5alpha-Reductase?", Mol. Interv., 7(1):10-13, (2007).
Gascard, P. et al., "Epigenetic and Transcriptional Determinants of the Human Breast", Nat. Commun., 6:6351, 10 pages (2015).
Gaubin, M. et al., "Potent Inhibition of CD4/TCR-Mediated T Cell Apoptosis by a CD4-Binding Glycoprotein Secreted from Breast Tumor and Seminal Vesicle Cells", J. Immunol., 162:2631-2638, (1999).
Ghajar, C., "A Stiffness-Mediated Oncogenic Hammer", Sci. Transl. Med., 6(237):237fs21, 3 pages, (2014).
Ghosh, S. et al., "Mechanical Phenotype is Important for Stromal Aromatase Expression", Steroids, 76(8):797-801, (2011).
Giess, C. et al., "Background Parenchymal Enhancement at Breast MR Imaging: Normal Patterns, Diagnostic Challenges, and Potential for False-Positive and False-Negative Interpretation", RadioGraphics, 34(1):234-247, (2014).
Gilliver, SC et al., "5alpha-Dihydrotestosterone (DHT) Retards Wound Closure by Inhibiting Re-Epithelialization", J. Pathol., 217:73-82, (2009).
Glaser, R. "Subcutaneous Testosterone-Anastrozole Implant Therapy in Breast Cancer Survivors", 2010 Breast Cancer Symposium, Abstract 221, Jan. 2010; 1 page.
Glaser, R. et al., "Beneficial Effects of Testosterone Therapy in Women Measured by the Validated Menopause Rating Scale {MRS}", Maturitas, 68(4):355-361, (2011).
Glaser, R. et al., "Rapid Response of Breast Cancer to Neoadjuvant Intramammary Testosterone-Anastrozole Therapy: Neoadjuvant Hormone Therapy in Breast Cancer", Menopause, 21(6):673-678, (2014).
Glaser, R. et al., "Reduced Breast Cancer Incidence in Women Treated with Subcutaneous Testosterone, or Testosterone with Anastrozole: A Perspective, Observational Study", Maturitas, 76:342-349, (2013).
Glaser, R. et al., "Subcutaneous Testosterone-Letrozole Therapy Before and Concurrent with Neoadjuvant Breast Chemotherapy: Clinical Response and Therapeutic Implications", Menopause: The Journal of The North American Menopause Society, 24(7):859-864, (2017).
Glaser, R. et al., "Subgroups of Patients Treated With An Aromatase Inhibitor (Anastrozole) Delivered Subcutaneously in Combination With Testosterone", Abstract, 9th European Congress on Menopause and Andropause, Maturitas, vol. 71, Supplement 1, Mar. 28, 2012; 1 page.
U.S. Appl. No. 17/437,525; Corrected Notice of Allowance, dated May 11, 2022; 6 pages.
U.S. Appl. No. 17/437,525; Non-Final Office Action, dated Jan. 27, 2022; 36 pages.
U.S. Appl. No. 17/437,525; Notice of Allowance, dated Apr. 26, 2022; 13 pages.
Bercoff, J., "ShareWave~ Elastography—White Paper" Super Sonic Imagine, S.A. copyright (2008).
Cheng, Q. et al., "Overexpression of CD36 in mammary fibroblasts suppresses colony growth in breast cancer cell lines", Biochem Biophys Res Commun., 526(1):41-7, (2020).
D'Orsi, C. et al., "Breast Imaging Reporting and Data System", ACR BI-RADS® Atlas, Reston, VA: American College of Radiology, (2013).
Das, L. et al., "Idiopathic gigantomastia: newer mechanistic insights implicating the paracrine milieu", Endocrine, 66 (2):166-77, (2019).
Dawson, C. et al., "Tissue-resident ductal macrophages survey the mammary epithelium and facilitate tissue remodelling", Nat Cell Biol., 22(5):546-58, (2020).
Goulabchand, R. et al., "Mastitis in Autoimmune Diseases: Review of the Literature, Diagnostic Pathway, and Pathophysiological Key Players", J Clin Med., 9(4):958, (2020).
Gubbels-Bupp, M. et al., "Androgen-Induced Immunosuppression", Front Immunol., 9:974, (2018).

Guhl, S. et al., "Testosterone exerts selective anti-inflammatory effects on human skin mast cells in a cell subset dependent manner", Exp Dermatol., 21(11):878-80, (2012).
Liu, Y. et al., "Sinomenine hydrochloride inhibits the progression of plasma cell mastitis by regulating IL-6/JAK2/ STAT3 pathway", Int Immunopharmacol., 81:106025, (2020).
Touraine, P. et al., "Breast inflammatory gigantomastia in a context of immune-mediated diseases", J Clin Endocrinol Metab., 90(9):5287-94, (2005).
Uray, I. et al., "Estradiol down-regulates CD36 expression in human breast cancer cells", Cancer Lett., 207(1):101-7, (2004).
Walecki, M. et al., "Androgen receptor modulates Foxp3 expression in CD4+CD25+Foxp3+ regulatory T-cells", Mol Biol Cell., 26(15):2845-57, (2015).
Wang, H. et al., "CD36-mediated metabolic adaptation supports regulatory T cell survival and function in tumors", Nat Immunol., 21(3):298-308, (2020).
Davis, S. et al., "The effect of transdermal testosterone on mammographic density in postmenopausal women not receiving systemic estrogen therapy", J Clin Endocrinol Metab., 94(12):4907-13, (2009).
Fabian, C. et al., "Reduction in proliferation with six months of letrozole in women on hormone replacement therapy", Breast Cancer Res Treat., 106(1):75-84, (2007).
Henry, N. et al., "Aromatase inhibitor-induced modulation of breast density: clinical and genetic effects", Br J Cancer, 109(9):2331-9, (2013).
Rhoden, El et al., "Treatment of Testosterone-Induced Gynecomastia with the Aromatase Inhibitor, Anastrozole", Intl. J. of Impotence Res., 16:95-97, (2004).
Rinsho, et al., Japanese Journal of Clinical and Experimental Medicine, 70(11):3428-3433, 7 pages, (1993).
Robinson, J. et al., "Androgen Receptor Driven Transcription in Molecular Apocrine Breast Cancer is Mediated by FoxA1", EMBO J., 30(15):3019-3027, (2011).
Robinson, J. et al., "FoxA1 is a Key Mediator of Hormonal Response in Breast and Prostate Cancer", Front. Endocrin., 3(68):1-6, (2012).
Santen, R., "Recent Progress in Development of Aromatase Inhibitors", J. Steroid Biochem. Molec. Biol., 37 (6):1029-1035, (1990).
Scurr, J. et al., "The Prevalence, Severity, and Impact of Breast Pain in the General Population", Breast J., 20 (5):508-13, (2014).
Smith, J. et al., "A Pilot Study of Letrozole for One Year in Women at Enhanced Risk of Developing Breast Cancer: Effects on Mammographic Density", Anticancer Res., 32(4):1327-31, (2012).
Smith, R. et al., "Evaluation and Management of Breast Pain", Mayo Clin. Proc., 79:353-372, (2004).
Somboonporn, W. et al., "Postmenopausal Testosterone Therapy and Breast Cancer Risk", Maturitas, 49:267-275, (2004).
Tarone, R. et al., "Breast Reduction Surgery and Breast Cancer Risk: Does Reduction Mammaplasty Have a Role in Primary Prevention Strategies for Women at High Risk of Breast Cancer?", Plasl. Reconstr. Surg., 113(7):2104-2110, (2004).
The Merck Index, 13th ed., Merck & Co., Inc., Entry Nos. 632 (p. 105), 3944 (p. 692) and 9255 (p. 1638), 2001).
The North American Menopause Society, "The Role of Testosterone Therapy in Postmenopausal Women: Position Statement of The North American Menopause Society", Menopause, 12(5):497-511, (2005).
Titus-Ernstoff, L. et al., "Breast Cancer Risk Factors in Relation to Breast Density (United States)", Cancer Causes Control, 17(10):1281-1290, (2006).
Tiwary, B. et al., "Parallel Evolution Between Aromatase and Androgen Receptor in the Animal Kingdom", Mol. Biol. vol., 26(1):123-129, (2009).
U.S. Appl. No. 15/460,895; Non-Final Office Action, dated Dec. 19, 2017; 17 pages.
Vachon, C. et al., "Mammographic Breast Density Response to Aromatase Inhibition", Clin. Cancer Res., 19 (8):2144-2153, (2013).
Viacava, P. et al., "Spectrum of GCDFP-15 Expression in Human Fetal and Adult Normal Tissues", Virchows Arch, 132:255-260, (1998).

(56) References Cited

OTHER PUBLICATIONS

Wanders, J. et al., "The Effect of Weight Change on Changes in Breast Density Measures Over Menopause in a Breast Cancer Screening Cohort", Breast Cancer Res., 8 pages, (2015).
Warwick, J. et al., "Mammographic Breast Density Refines Tyrer-Cuzick Estimates of Breast Cancer Risk in High-Risk Women: Findings from the Placebo Arm of the International Breast Cancer Intervention Study I", Breast Cancer Res., 16:451, 6 pages, (2014).
Wasaff, Barbara, "Current Status of Hormonal Treatments for Metastatic Breast Cancer in Postmenopausal Nomen," Oncol. Nurs. Forum, 24(9), 1515-1520 (1997).
Wu, S. et al., "Quantitative Assessment of Background Parenchymal Enhancement in Breast MRI Predicts Response to Risk-Reducing Salpingo-Oophorectomy: Preliminary Evaluation in a Cohort of BRCA 1/2 Mutation Carriers", Breast Cancer Res., 11 pages, (2015).
Yang, Y. et al., "Influence of Factors on Mammographic Density in Premenopausal Chinese Women", Eur. J. Cancer Prev., 6 pages, (2015).
Youk, J. et al., "Quantitative Lesion-to-Fat Elasticity Ratio Measured by Shear-Wave Elastography for Breast Mass: Which Area Should Be Selected as the Fat Reference?", PLOS One, 10(9):e0138074, 11 pages, (2015).
Zhong, A. et al., "Stromal-Epithelial Cell Interactions and Alteration of Branching Morphogenesis in Macromastic Mammary Glands", J. Cell Mol. Med., 18(7):1257-1266, (2014).
Zhou, J. et al., "Testosterone Inhibits Estrogen-Induced Mammary Epithelial Proliferation and Suppresses Estrogen Receptor Expression", FASEB J., 14:1725-1730 (2000).
Zimmerman, Y. et al., "The Effect of Combined Oral Contraception on Testosterone Levels in Healthy Women: A Systematic Review and Meta-Analysis," Hum. Reprod. Update, 20(1):76-105, (2014).
Atakpa, E. et al., "Mammographic density, endocrine therapy and breast cancer risk: a prognostic and predictive biomarker review", Cochrane Database Syst Rev., 10(10):CD013091, (2021).
Cigler, T. et al., "A randomized, placebo-controlled trial (NCIC CTG MAP1) examining the effects of letrozole on mammographic breast density and other end organs in postmenopausal women", Breast Cancer Res Treat., 120 (2):427-35, (2010).
De Gooyer, M. et al., "Tibolone is not converted by human aromatase to 7α-methyl-17α-ethynylestradiol (7α-MEE): analyses with sensitive bioassays for estrogens and androgens and with LC-MSMS", Steroids, 68(3):235-43, (2003).
Li, G. et al., "Effects of aromatizable and nonaromatizable androgens on the sex inversion of red-spotted grouper (*Epinephelus akaara*)", Fish Physiol Biochem., 32(1):25-33, (2006).
Mor, G. et al., "17α-Methyl testosterone is a competitive inhibitor of aromatase activity in Jar choriocarcinoma cells and macrophage-like THP-1 cells in culture", J Steroid Biochem Mol Biol., 79(1-5):239-46, (2001).
Mukawa, F., "Aromatase inhibitors", J Synth Org Chem., 46(8):742-52, (2008).
Pitot, H., "The molecular biology of carcinogenesis", Cancer, 72(S3):962-70, (1993).
Saria, M., "Overview of Cancer", Oncol Nursing Soc., pp. 1-11, (2018).
Shawky, M. et al., "Mammographic density: a potential monitoring biomarker for adjuvant and preventative breast cancer endocrine therapies", Oncotarget, 8(3):5578-91, (2017).
Simpson, E. et al., "Aromatase and its inhibitors: significance for breast cancer therapy", Recent Prog Horm Res., 57:317-38, (2002).
Smith, I. et al., "Comparative Efficacy and Safety of Adjuvant Letrozole Versus Anastrozole in Postmenopausal Patients With Hormone Receptor-Positive, Node-Positive Early Breast Cancer: Final Results of the Randomized Phase III Femara Versus Anastrozole Clinical Evaluation (FACE) Trial", J Clin Oncol., 35(10):1041-8, (2017).

\* cited by examiner

A) Estimation of radius (R1) from measure of breast volume

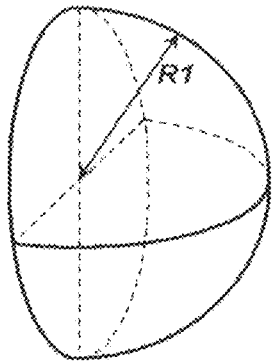

Volume – hemisphere $\longrightarrow R_{volume} = R1$ (cm)

$$\text{Volume} = \frac{1}{2}\left(\frac{4}{3}\pi R^3_{volume}\right)$$

FIG. 3A

B) Estimation of radius (R2) from measure of compressed breast area

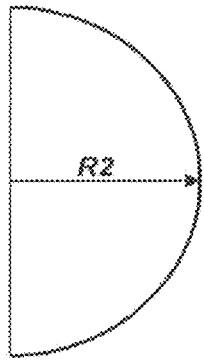

Area – semicircle $\longrightarrow R_{compressed\ area} = R2$ (cm)

$$\text{Area} = \frac{1}{2}\left(\pi R^2_{compressed\ area}\right)$$

FIG. 3B

C) Calculation of breast stiffness from R1, R2 and compression force

Compression force = $F$ (dN)

$$\text{Stiffness} \propto \frac{F}{R2-R1}\ (N/cm)$$

FIG. 3C

| N = 69,874 women | Sensitivity of double-reading digital mammography | False-positives (percentage of recalls that turn out to be negative for cancer) |
|---|---|---|
| VDG 1 | 85.0% | 11.4% |
| VDG 2 | 77.6% | 14.1% |
| VDG 3 | 69.0% | 18.3% |
| VDG 4 | 58.6% | 28.6% |

| Collected: | 30/12/2014, 08:10 | |
|---|---|---|
| LH | 6.0 | U/L |
| FSH | 7.9 | U/L |
| Oestradiol | 241 | pmol/L |
| SHBG | 88 | nmol/L |
| Testosterone | 6.8 | nmol/L |
| Free Androgen Index | 7.7 | % |

Figure 26A

| Collected: | 21/04/2015, 08:08 | |
|---|---|---|
| (Roche Method) | | |
| LH | 9.7 | U/L |
| FSH | 7.5 | U/L |
| Oestradiol | 448 | pmol/L |
| SHBG | 69 | nmol/L |
| Testosterone | 9.8 | nmol/L |
| Free Androgen Index | 14.2 | % |

Figure 26B

Before treatment 100mm pain score

No Pain 0mm          Worst pain 100mm

After treatment 100mm pain score

No Pain 0mm          Worst pain 100mm

METHODS OF REDUCING MAMMOGRAPHIC BREAST DENSITY AND/OR BREAST CANCER RISK

FIELD

The present disclosure is directed generally to methods for reducing mammographic breast density and/or breast stiffness in warm blooded animals, for example, in a woman, such as a pre-menopausal, a peri-menopausal, or a post-menopausal woman, comprising the administration of an effective amount of androgenic agent and an effective amount of an aromatase inhibitor. The present disclosure is also directed to reducing breast pain. The present disclosure is also directed to methods for reducing elasticity and/or decreasing mechano-transduction on the genome of breast cells. The present disclosure is also directed to providing an effective amount of an androgenic agent and an aromatase inhibitor to breast tissue resulting in stabilization and/or increase of the levels of androgen receptor expression. The present disclosure is also directed to reducing the risk of breast cancer in warm blooded animals by administering an effective amount of androgenic agent and an effective amount of an aromatase inhibitor to certain warm blooded animals with unacceptable breast density and/or breast stiffness.

RELATED REFERENCES

Boyd, et al., "Evidence that Breast Tissue Stiffness is Associated with Risk of Breast Cancer" PLoS One 2014 Jul. 10; 9(7):e100937

D'Orsi C J, Sickles E A, Mendelson E B, Morris E A et al. (2013). *ACR BI-RADS® Atlas, Breast Imaging Reporting and Data System*. Reston, Va.: American College of Radiology.

Jeremy Bercoff, "Sharewave Elastography—White Paper" SuperSonic Imagine, S.A. copyright 2008.

This application claims the benefit of US provisional patent application No. 62/067,297, entitled "Methods of Reducing Mammographic Breast Density and/or Breast Cancer Risk", filed Oct. 22, 2014.

These references and U.S. patent application No. 62/067,297 in their entirety, are incorporated herein by reference.

BACKGROUND

It has been estimated that 43% of women in the United States of America from 40 and 75 years of age have mammographic breast density (MBD) which is categorized as high, i.e. having a Breast Imaging-Reporting and Data System (BI-RADS®) score of 3 and 4 (or c and d). The American Cancer Foundation has suggested that this high breast density is a significant risk factor for the development of breast cancer. MBD may not be related to how a breast feels to palpation; but rather how it looks on the mammogram. Therefore a woman could be oblivious to how dense her breast tissue is and how high a risk-factor this is for developing breast cancer.

Traditionally, therapeutic intervention for the peri-menopausal transition is either a low dose combination oral contraceptive or continuous estradiol and a synthetic progestin delivery system to protect the uterus from both increased endometrial cancer risk and unwanted uterine bleeding. The present inventors believe that these are inappropriate treatments for women with high breast density and/or breast stiffness as they reduce an already precarious testosterone level and increase breast density and/or breast stiffness. However these are the current recommendations of the Menopause Society of North America and the Menopause Society of Australia.

While hormonal prevention strategy studies have demonstrated that anti-estrogens such as tamoxifen and aromatase inhibitors, as well as selective estrogen receptor modulators, may reduce the incidence of breast cancer, none of these have widespread use due to the side-effects associated with the menopausal symptoms induced by these therapies.

Although the mechanisms by which breast density and/or breast stiffness affects breast cancer risk are not well understood, it is estimated that a significant percentage of breast cancers are attributable to unacceptable levels of breast density and/or breast stiffness. To date there has been no successful prescribed method for the reduction of mammographic breast density and/or breast stiffness and therefore, the reduction in the instances of breast cancer associated with such conditions in certain women. For example, tamoxifen has been shown to reduce mammographic breast density but its use has been limited by poor compliance due to side effects. There is no known method for the reduction of breast stiffness.

Another problem in the prior art is breast pain and its treatment. Breast pain is a significant problem in female health. It has been estimated that 45% of woman in their thirties indicated that breast pain impinges on their quality of life and 10% indicated that they have experienced breast pain for at least half their life. There is little in the way of treatment; tamoxifen has been used as an off-label medication for this condition. However, tamoxifen is associated with significant side effects that impact on its compliance in patients. There is a need in the art for better treatments to reduce breast pain in women.

Another problem in the prior art is rapid breast enlargement known as macromastia that may occur at any stage of a woman's life and results in extreme discomfort and pain. Macromastia is known to have a substantial negative impact on health-related quality of life, self-esteem, physical symptoms and eating behaviors in adolescents with this condition. To date medical treatments have not been consistently effective. Medical treatments have included, for example, use of progesterone, tamoxifen and testosterone as well as surgical therapy (i.e. reduction mammoplasty and mastectomy). There is a need for more effective treatments for macromastia other then surgical breast reduction.

Tamoxifen has been used in pre-menopausal woman for reducing the risk of developing breast cancer. Part of the problem associated with the use of tamoxifen in pre-menopausal women is the effect it has on the pituitary gland. Tamoxifen significantly increases FSH and LH levels in pre-menopausal woman. This side effect of causing perturbations in the pituitary function may result in high levels of estradiol which among other things may lead to cardiovascular and/or central nervous system side effects. There is a need in art for better therapies in pre-menopausal and/or peri-menopausal women for reducing the risk of breast cancer and at the same time not causing perturbations in the hypothalamic-pituitary axis and/or other endocrine axis.

Elasticity of breast tissue is recognized as a factor in the formation of breast cancer. It has been demonstrated that increased elasticity in breast cells results in an increased mechano-transduction across the genome of a cell, which can result in greater malignant transformation. There is a need in the art for methods of decreasing mechano-transduction on the genome of a cell in order to reduce the risk of malignant transformation. The present disclosure is directed to methods for achieving such a result by reducing elasticity and/or decreasing mechano-transduction on the genome of breast cells.

Another problem in the prior art is the number of cysts found in certain patients' breasts. It is known that women that have breast cyst are at higher risk of high breast density and/or breast cancer. Accordingly, it is desirable to reduce the amount and/or size of breast cysts in a woman's breast. There is a need in art for better therapies in women for reducing the size and quantity of cysts found in the breasts.

The present disclosure is directed to overcome and/or ameliorate at least one or more of the disadvantages of the prior art, as will become apparent from the discussion herein. The present disclosure also provides other advantages and/or improvements as discussed herein.

Definitions

Terms are used herein as generally used in the art, unless otherwise defined in the following:

The term "absolute area of breast density" (AABD) is understood to mean the measurement of the surface area of fibro-glandular tissue in a subject's mammogram in square centimeters. For example, this may be measured using CUMULUS software algorithms or visual inspection of a mammogram. There are several other tests that may be used to measure AABD, including but not limited to, VOLPARA, QUANTRA, and methods taking into account the surface area of fibro-glandular tissue in a mammogram.

The term "adjuvant therapy" may include adjuvant, neo-adjuvant and/or palliative therapy.

The term "androgenic agent" is understood to mean a chemical that increases androgenic activity or synthesis. Typically, an androgenic agent is a steroid hormone or non-steroid hormone that binds with high affinity (in the pM or nM range) and specificity to its intracellular mediator, the androgen receptor, to stimulate transactivation activity and thus regulate the expression of target genes. Non-limiting examples are testosterone, isomers, metabolites, derivatives, precursors of testosterone or combinations thereof; synthetic hormones and/or non-synthetic hormones; and/or selective androgen receptor modulators (SARM). Other examples are provided herein.

The term "area breast density percentage" (ABD %) as used herein mean the proportion or percentage of fibro-glandular (dense) tissue relative to the total surface area of the breast on a mammogram. For example, this may be measure using CUMULUS software algorithms or visual inspection of a mammogram. There are several other tests that may be used to measure ABD %, including but not limited to, VOLPARA, QUANTRA, and methods taking into account the surface area of fibro-glandular tissue in a mammogram.

The term "aromatase inhibitor" is understood to mean a chemical compound, hormone or polypeptide that blocks and/or inhibits the activity of aromatase which is an enzyme that converts androgens to estrogens. Examples are provided herein.

The term "breast cancer" is understood to mean a malignant proliferation of epithelial cells lining the ducts or lobules of the breast.

The term "breast elasticity" is understood to mean a measurement of the pressure required to achieve a given fractional deformation of the breast or a part of the breast. For example, Elasticity=Pressure/Fractional change in radius of the breast, where pressure is measured in, for example, kilo-pascals and fractional change in radius of the breast=$(R1-R2)/R1$, where $R1$ is the uncompressed radius and $R2$ is the compressed radius. Another example is to measure the shear elasticity of breast tissue by applying shear waves though the breast tissue, for example, using the SuperSonic Imagine Aixplorer™ that uses SuperSonic Imagine's ShearWave™ Elastography.

The term "breast stiffness" is understood to mean, in its broadest sense, as the measurement of the resistance of a breast to deformation. Factors that may influence the degree of breast stiffness include, but is not limited to, physical forces generated by interactions between cells and between cells and the extracellular matrix, the number of cells and the extent of collagen present in the breast, the degree of fluid retention within the breast and the degree of proteoglycan expression. One example of measuring breast stiffness includes the use of the formula force/deformation (dN/cm), where dN denotes deca-Newtons and cm centimetres, wherein the deformation may be determined as the difference between the radius of the mammographic area semi-circle and the radius of the volumetric hemisphere, and the the compression force is recorded from the mammogram, such as a digital mammogram. For example, under Boyd, et al., the deformation may be determined as the difference $R1-R2$, where $R1$ is the un-compressed radius and $R2$ is the compressed radius. (Boyd, et al., "Evidence that Breast Tissue Stiffness is Associated with Risk of Breast Cancer" PLoS One 2014 Jul. 10; 9(7):e100937)

The term "breast tissue" is understood to mean the collection of epithelial cells, stromal cells, extracellular matrix, and/or migratory cells, located within and in the vicinity of the breast.

The term "effective amount" or "pharmaceutically effective amount" of an agent or compound as provided herein is understood to mean a sufficient amount of the agent or compound to provide the desired therapeutic effect and is nontoxic, has an acceptable nontoxic profile and/or an acceptable side effects profile. The amount required may vary from patient to patient, depending, for example, on age, general condition of the patient, the severity of the condition being treated, the particular agent or compound administered one or more combinations of these factors and the like. An appropriate "effective amount" typically in an individual case may be determined by one of ordinary skill in the art by reference to the pertinent texts and literature and/or using routine experimentation.

The term "mammographic breast density" or "MBD" is understood to mean a qualitative estimate of the proportion or percentage of radiopaque, or fibro-glandular ("dense") elements/tissue in the breast relative to total breast area (via 2-D determination) or volume (via 3-D determination). Mammographic Breast Density (MBD) is the qualitative or quantitative estimate of amount of the fibro-glandular tissue (FGT) within the breast. It may be either the absolute amount of FGT or the relative amount of FGT to the amount of non-FGT (mainly adipose or fat). The absolute amount of FGT can be either estimated as a function of surface area ($cm^2$) (i.e., AABD) or volume ($cm^3$) (i.e. AVBD). The relative amount of FGT is an estimate of surface area of FGT relative to non-FGT (as a percentage (i.e. ABD %)) or an estimate of volume of the FGT to volume of the breast (i.e. VBD %). Another way is to determine absolute volumetric breast density (i.e. AVBD) which is the measured volume of fibro-glandular tissue in a subject's breast in cubic centimeters. Mammographic breast density may be determined by various methods, including but not limited to, mammography, digital mammography, magnetic resonance imaging (MRI), ultrasound, digital breast tomosynthesis (DBT), virtual touch tissue imaging quantification (VTIQ), and combinations thereof. MBD may be qualitatively assessed, via 2-D determinations and/or using the BI-RADS® density categories, with 1 (or a) being least dense and 4 (or d) being the most dense. MBD may also be qualitatively and/or quantitatively assessed via 3-D determinations and/or using volumetric measurements of the breast, such as determining the volumetric breast density, which is the proportion of fibro-glandular (dense) tissue relative to the total volume of tissue in the breast (e.g., fibro-glandular (dense) tissue and fat in the breast). Another way is to determine absolute volumetric breast density (AVBD) which is the measured volume of fibro-glandular tissue in a subject's breast in cubic centimeters. Assessments of MBD via 3-D determinations can also account for heterogeneity of dense tissue within the breast. There are several tests that may be used to measure MBD, including but not limited to, VOLPARA, QUANTRA, CUMULUS, and methods taking into account the volume of fibro-glandular tissue ($cm^3$).

The term "patient" is an animal including the human species that is treatable with the compositions, methods and kits of the present disclosure. The term "patient" or "patients" is intended to refer to both the male and female gender unless one gender is specifically indicated or clear from the context. The term "patient" may also refer to a female to male transgender.

The term "peri-menopause" or "menopausal transition" is understood to mean the period of time around menopause during which a woman's body makes its natural transition toward permanent infertility (menopause). Women may start peri-menopause at different ages, and may notice signs of progression toward menopause, such as menstrual irregularity, during their 40's, or even as early as their mid-30's. During peri-menopause, estrogen levels may rise and fall unevenly, menstrual cycles may lengthen or shorten, and menstrual cycles may begin in which the ovaries do not release an egg (ovulate). During peri-menopause, other menopause-like symptoms may be experienced, including, but not limited to, hot flashes, sleep problems, and/or vaginal dryness.

The term "peri-menopausal symptoms" is understood to include, but is not limited to, menstrual irregularity: hot flashes and sleep problems; mood changes; mood swings; irritability; depression; vaginal dryness; urinary or vaginal infections; urinary incontinence; decreasing fertility; changes in sexual arousal or desire; bone loss; fragile bones; osteoporosis; or changing cholesterol levels, such as an increase in low-density lipoprotein (LDL) cholesterol, or a decrease in high-density lipoprotein (HDL) cholesterol and combinations thereof.

The term "pharmaceutically acceptable" is understood to mean those compounds, agents, materials, compositions, excipients, and/or dosage forms that are, within the scope of sound medical judgment, suitable for contact with the tissues of human beings and/or animals without excessive toxicity, irritation, allergic response, or other problems or complications commensurate with a reasonable benefit and/or risk ratio.

The term "post-menopausal woman" is understood to include not only a woman of advanced age who has passed through menopause, but also a woman who has had her ovaries removed or destroyed by other means or for some other reason has suppressed estrogen production, such as one who has undergone long-term administration of corticosteroids, suffer from Cushing's syndrome or has gonadal dysgenesis.

The term "selective androgen receptor modulator" or "SARM" is an androgenic agent and is understood to include an agonist, or partial agonist, of androgen receptor in the cell wall, cytoplasm or nucleus of a cellular element found within the breast (e.g., stromal, epithelial, adipocyte, or cellular element that may enter the breast as a migratory element, such as a macrophage or lymphocyte. As used herein the term SARM may also be defined as an androgenic agent that is tissue-selective for tissues other than breast tissue including but not limited to bone, muscle and/or central nervous system tissues.

The term "subject" is an animal including the human species that is treatable with the compositions, methods and kits of the present disclosure. The term "subject" or "subjects" is intended to refer to both the male and female gender unless one gender is specifically indicated or clear from the context. The term "subject" may also refer to a female to male transgender.

The term "treatment" or "therapy" as used herein includes preventative (e.g., prophylactic) treatment and/or palliative treatment and "treating" as used herein refers to the act of providing preventative and/or palliative treatment.

The term volumetric breast density percentage (VBD %) as used herein means the proportion or percentage of fibro-glandular (dense) tissue in volume relative to the total volume of tissue in the breast. For example, this may be measured using the Volpara Solution™ software algorithms. In the Volpara Solution™ software algorithms VBD % is referred to as volumetric breast density percentage. There are several other tests that may be used to measure VBD %, including but not limited to, QUANTRA, CUMULUS, and methods taking into account the volume of fibro-glandular tissue.

It will be apparent to one skilled in the art, in view of the following detailed description and the claims appended hereto, that various substitutions and/or modifications may be made to the present disclosure without departing from the scope of the inventions as claimed.

SUMMARY

Certain embodiments are directed to a method of treating mammographic breast density and/or breast stiffness in a patient in need thereof, comprising administering to the patient: i) an effective amount of androgenic agent; and ii) an effective amount of an aromatase inhibitor.

Certain embodiments are directed to a method of treating mammographic breast density as measured by AVBD and/or VBD % in a patient in need thereof, comprising administering to the patient: i) an effective amount of androgenic agent; and ii) an effective amount of an aromatase inhibitor.

Certain embodiments are directed to a method of reducing VBD % in a patient in need thereof, comprising administering to the patient: i) an effective amount of androgenic agent; and ii) an effective amount of an aromatase inhibitor.

Certain embodiments are directed to a method of reducing AVBD in a patient in need thereof, comprising administering to the patient: i) an effective amount of androgenic agent; and ii) an effective amount of an aromatase inhibitor.

Certain embodiments are directed to a method of reducing AVBD and VBD % in a patient in need thereof, comprising administering to the patient: i) an effective amount of androgenic agent; and ii) an effective amount of an aromatase inhibitor.

Certain embodiments are directed to a method of treating mammographic breast density as measured by AABD and/or ABD % in a patient in need thereof, comprising administering to the patient: i) an effective amount of androgenic agent; and ii) an effective amount of an aromatase inhibitor.

Certain embodiments are directed to a method of reducing ABD % in a patient in need thereof, comprising administering to the patient: i) an effective amount of androgenic agent; and ii) an effective amount of an aromatase inhibitor.

Certain embodiments are directed to a method of reducing AABD in a patient in need thereof, comprising administering to the patient: i) an effective amount of androgenic agent; and ii) an effective amount of an aromatase inhibitor.

Certain embodiments are directed to a method of reducing AABD and ABD % in a patient in need thereof, comprising administering to the patient: i) an effective amount of androgenic agent; and ii) an effective amount of an aromatase inhibitor.

Certain embodiments are directed to a method of reducing mammographic breast density in a patient having a breast with a mammographic breast density of 7.5% or greater, comprising administering to the patient: i) an effective amount of androgenic agent; and ii) an effective amount of an aromatase inhibitor.

Certain embodiments are directed to a method of reducing VBD % in a patient having a breast with a VBD % of 7.5% or greater, comprising administering to the patient: i) an effective amount of androgenic agent; and ii) an effective amount of an aromatase inhibitor.

Certain embodiments are directed to a method of reducing ABD % in a patient having a breast with an ABD % of 7.5% or greater, comprising administering to the patient: i) an effective amount of androgenic agent; and ii) an effective amount of an aromatase inhibitor.

Certain embodiments are directed to a method of treating mammographic breast density in a patient having a breast with a BI-RADS® score of 3 or 4 (or c or d), comprising administering to the patient: i) an effective amount of androgenic agent; and ii) an effective amount of an aromatase inhibitor.

Certain embodiments are directed to a method of reducing mammographic breast density in a patient having a breast with a BI-RADS® score of 3 or 4 (or c or d), comprising administering to the patient: i) an effective amount of androgenic agent; and ii) an effective amount of an aromatase inhibitor.

Certain embodiments are directed to a method of inducing breast involution in a patient in need thereof, comprising administering to the patient: i) an effective amount of androgenic agent; and ii) an effective amount of an aromatase inhibitor.

Certain embodiments are directed to a method of inducing net cell death over proliferation in a breast of a patient in need thereof, comprising administering to the patient: i) an effective amount of androgenic agent; and ii) an effective amount of an aromatase inhibitor.

Certain embodiments are directed to a method of inducing net extracellular matrix degradation over development of extracellular matrix in a breast of a patient in need thereof, comprising administering to the patient: i) an effective amount of androgenic agent; and ii) an effective amount of an aromatase inhibitor.

Certain embodiments are directed to a method of reversing cell number and mammographic breast density in a breast of a peri-menopausal patient, comprising administering to the patient: i) an effective amount of androgenic agent; and ii) an effective amount of an aromatase inhibitor.

Certain embodiments are directed to a method of reducing mammographic breast density and peri-menopausal symptoms in a patient in need thereof, comprising administering to the patient an effective amount of androgenic agent.

Certain embodiments are directed to a method of reducing mammographic breast density and peri-menopausal symptoms in a patient in need thereof, comprising administering to the patient: i) an effective amount of androgenic agent; and ii) an effective amount of an aromatase inhibitor.

Certain embodiments are directed to methods for the identification of women in the peri-menopause and/or pre-menopause who have mammographically dense breast tissue and breast stiffness. Breast stiffness may be measured using an appropriate mathematical algorithm produced from mammographic images (for example, Boyd). Breast stiffness may be measured using shear wave elastography (for example, shear-wave elastography by SuperSonic Imagine). These identified women may then be provided with a prophylactic and an effective amount of androgenic agent and/or an effective amount of an aromatase inhibitor. For example, in certain embodiments, the composition may be administered by subcutaneous application.

Certain embodiments are directed to methods that may be used in pre-menopausal and/or peri-menopausal women for reducing the risk of breast cancer and at the same time not causing perturbations in the hypothalamic-pituitary axis and/or other endocrine axis, for example adrenal gland and/or ovary gland.

Certain embodiments are directed to methods of reducing breast stiffness in a patient in need thereof, comprising administering to the patient: i) an effective amount of an androgenic agent; and ii) an effective amount of an aromatase inhibitor.

Certain embodiments are directed to methods of reducing breast pain in a patient in need thereof, comprising administering to the patient: i) an effective amount of an androgenic agent; and ii) an effective amount of an aromatase inhibitor.

Certain embodiments are directed to methods of decreasing breast elasticity in a patient in need thereof, comprising administering to the patient: i) an effective amount of an androgenic agent; and ii) an effective amount of an aromatase inhibitor.

Certain embodiments are directed to methods of decreasing mechano-transduction on the genome of a cell in order to reduce the risk of malignant transformation in a patient in need thereof, comprising administering to the patient: i) an effective amount of an androgenic agent; and ii) an effective amount of an aromatase inhibitor.

Certain embodiments are directed to methods of increasing the ratio of fibro-glandular and adipose tissue in a patient in need thereof, comprising administering to the patient: i) an effective amount of an androgenic agent; and ii) an effective amount of an aromatase inhibitor.

Certain embodiments are directed to methods of increasing CD36 in a patient in need thereof, comprising administering to the patient: i) an effective amount of an androgenic agent; and ii) an effective amount of an aromatase inhibitor.

Certain embodiments are directed to methods of stabilizing and/or an increase in levels of androgen receptor expression in breast tissue of a patient in need thereof, comprising administering to the patient: i) an effective amount of an androgenic agent; and ii) an effective amount of an aromatase inhibitor.

Certain embodiments are directed to methods of reducing and/or treating macromastia in a patient in need thereof, comprising administering to the patient: i) an effective amount of an androgenic agent; and ii) an effective amount of an aromatase inhibitor.

Certain embodiments are directed to methods of increasing GCDFP15 in a patient in need thereof, comprising administering to the patient: i) an effective amount of an androgenic agent; and ii) an effective amount of an aromatase inhibitor.

Certain embodiments are directed to methods of reducing breast pain associated with having a mammography image taken in a patient in need thereof, comprising administering to the patient: i) an effective amount of an androgenic agent; and ii) an effective amount of an aromatase inhibitor.

Certain embodiments are directed to methods of increasing mammographic sensitivity in a patient, comprising administering to the patient: i) an effective amount of an androgenic agent; and ii) an effective amount of an aromatase inhibitor.

Certain embodiments are directed to methods of reducing ABD % and/or AABD in a patient in need thereof, comprising administering to the patient: i) an effective amount of an androgenic agent; and ii) an effective amount of an aromatase inhibitor.

Certain embodiments are directed to methods of reducing BPE in an MRI image of a patient, comprising administering to the patient: i) an effective amount of an androgenic agent; and ii) an effective amount of an aromatase inhibitor.

Certain embodiments are directed to methods of reducing the size and/or quantity of cysts in a patient in need thereof, comprising administering to the patient: i) an effective amount of an androgenic agent; and ii) an effective amount of an aromatase inhibitor.

The embodiments disclosed herein may optionally include a pharmaceutically acceptable excipient and/or carrier.

This summary is not intended to be limiting as to the embodiments disclosed herein and other embodiments are disclosed in this specification. In addition, limitations of one embodiment may be combined with limitations of other embodiments to form additional embodiments.

DETAILED DESCRIPTION OF THE DRAWINGS

For a better understanding of the disclosure, and to show more clearly how it may be carried into effect according to one or more embodiments thereof, reference will now be made, by way of example, to the accompanying figures.

FIG. 3A is a graphical and formulaic expression to estimate the radius (R1) from the measure of breast volume.

FIG. 3B is a graphical and formulaic expression to estimate the radius (R2) from the measure of compressed breast area.

FIG. 3C is a calculation of breast stiffness from R1, R2, and compression force.

Figure 9:
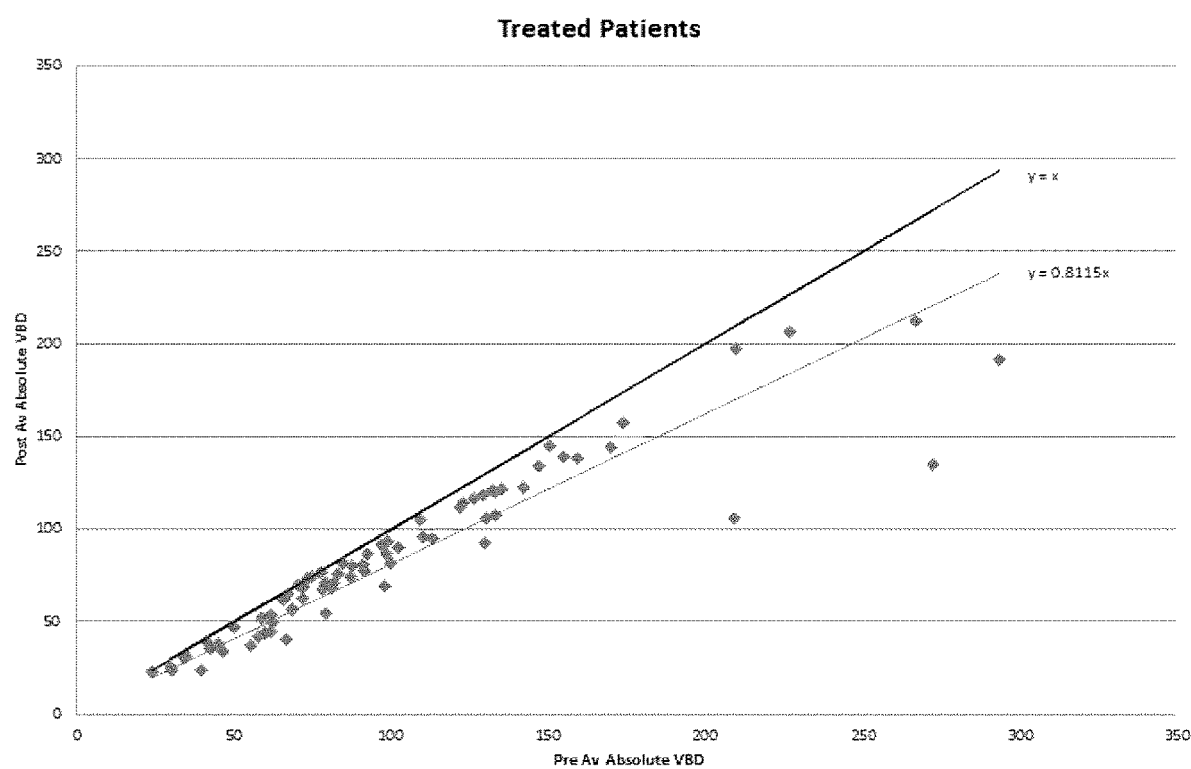

FIG. 9 provides a chart that plots for each patient treated with androgen agent and aromatase inhibitor a point having an x-coordinate equal to the pre-treatment AVBD in cubic centimeters and the y-coordinate being the post-treatment AVBD, according to an exemplary embodiment.

Figure 10:
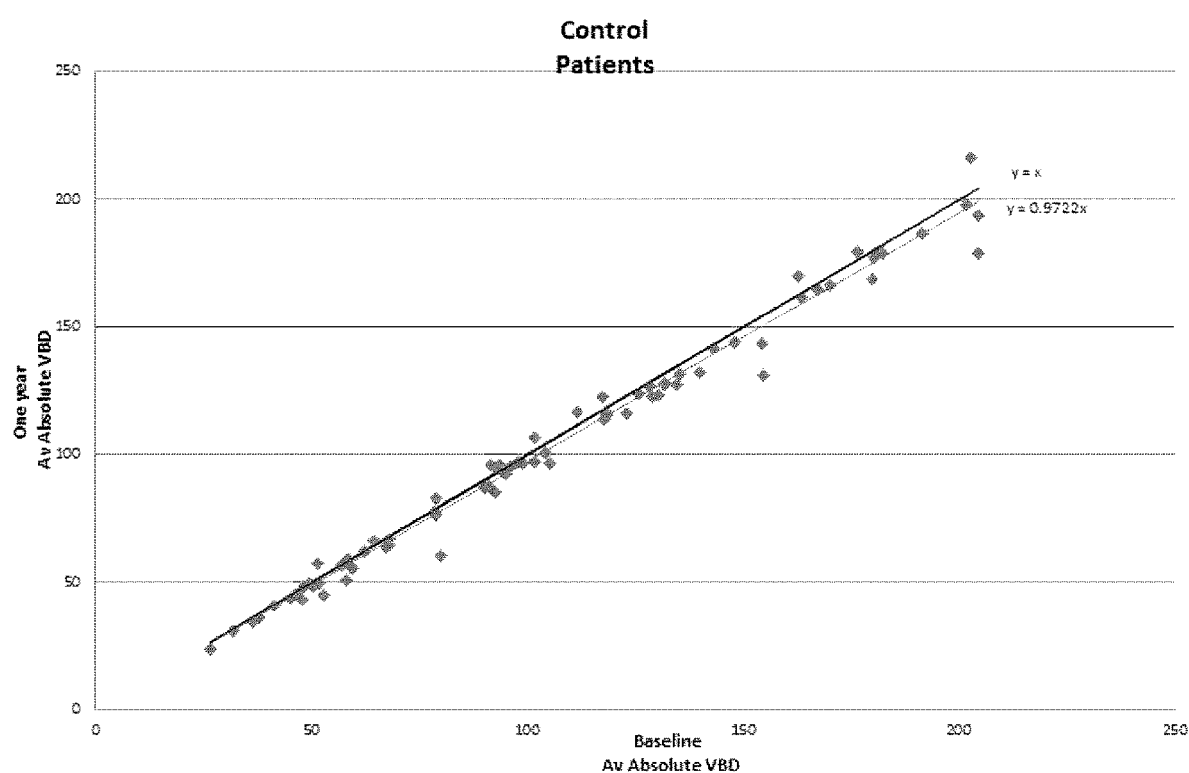

FIG. 10 is a chart that plots for each control group (untreated) patients a point having an x-coordinate equal to the baseline average AVBD in cubic centimeters and the y-coordinate being the AVBD one year from baseline, according to an exemplary embodiment.

Figure 11:
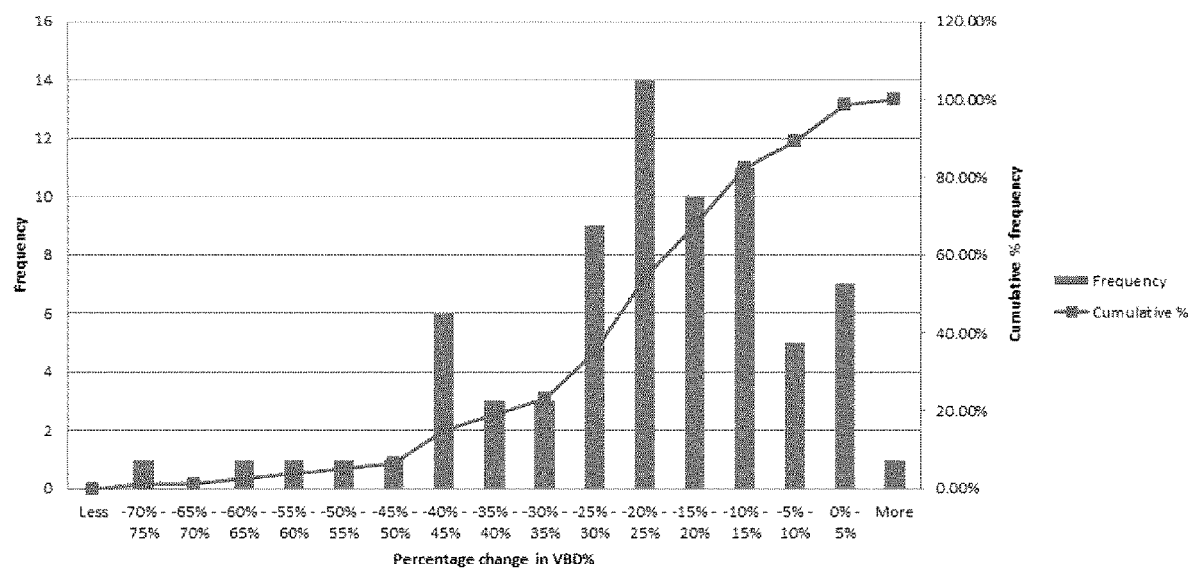

FIG. 11 is a histogram of the percent change of the mean of the VBD % of the treated patients, according to an exemplary embodiment.

Figure 12:
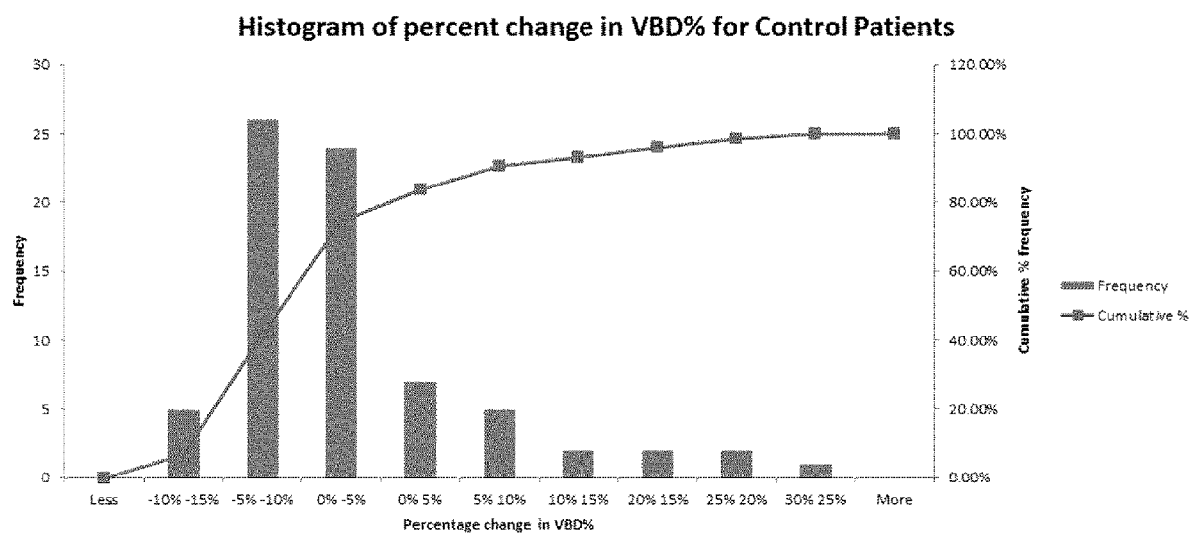

FIG. 12 is a histogram of the percent change of the mean VBD % of the control patients, according to an exemplary embodiment.

Figure 13:
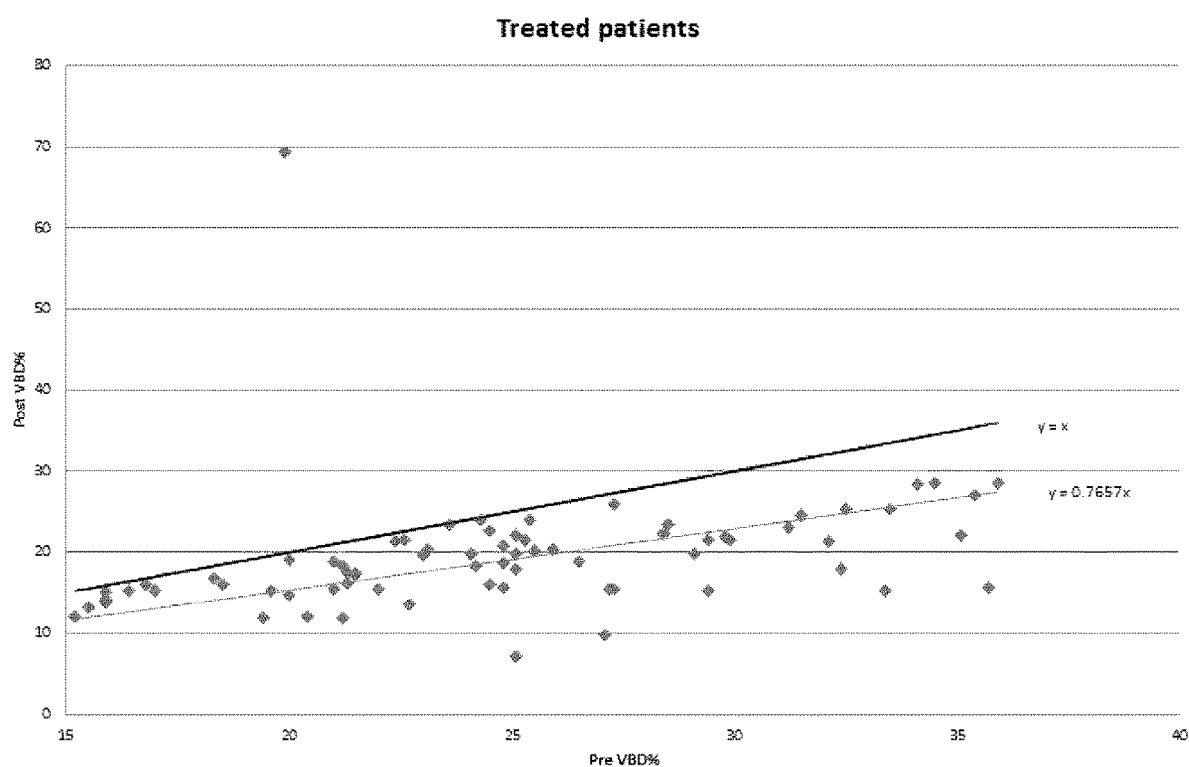

FIG. 13 is a chart that plots for each patient treated with an androgenic agent and an aromatase inhibitor a point having an x-coordinate representing the pre-treatment VBD % and a y-coordinate being the post-treatment VBD %, according to an exemplary embodiment.

Figure 14:
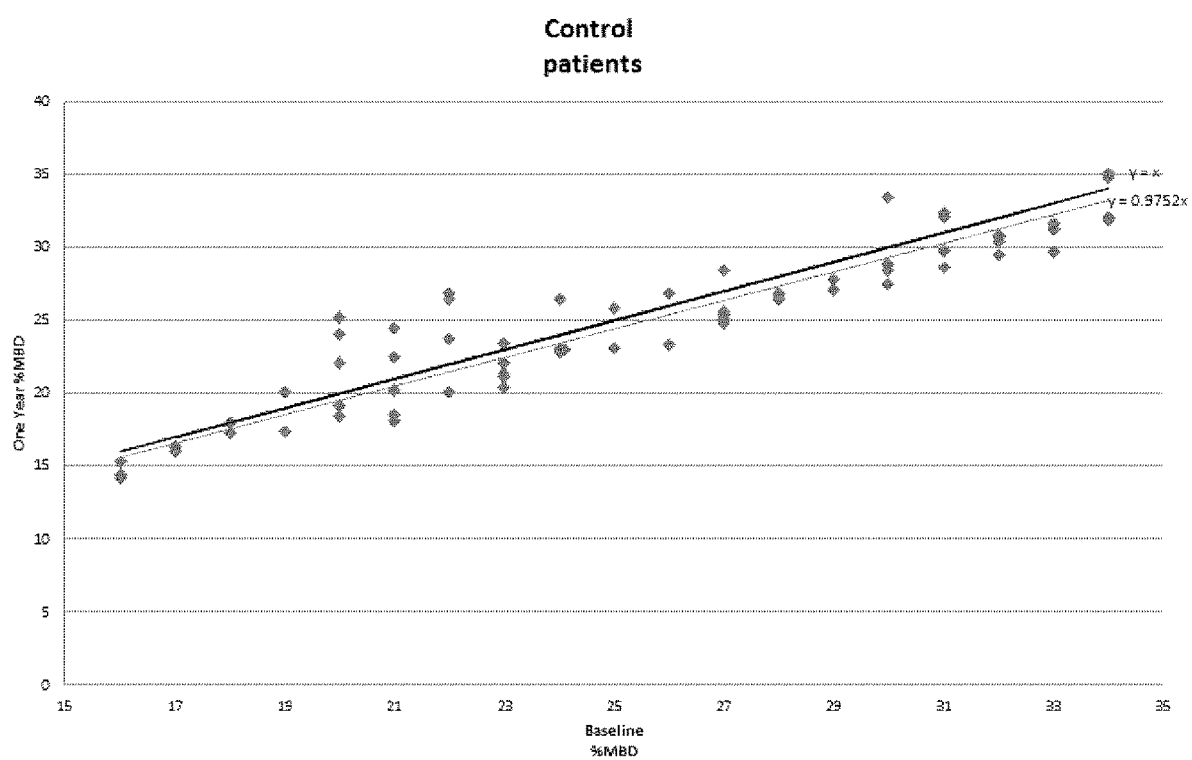

FIG. 14 is a plot that charts the control group having an x-coordinate equal to the base line VBD % and a y-coordinate being the VBD % after one year. Also plotted is the through-the-origin linear regression line which has the formula Post-treatment VBD %=0.975×Pre-treatment VBD %.

Figure 15A:
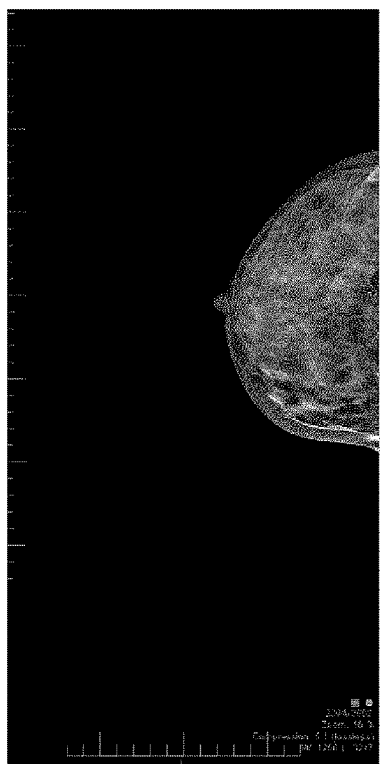

FIGS. 15A, B and C show mammographic images of a patient's breast: A after approximately 24 months of treatment (8 treatments in total); B after approximately 12 months (four treatments); and C pre-treatment, according to an exemplary embodiment.

Figure 16A:
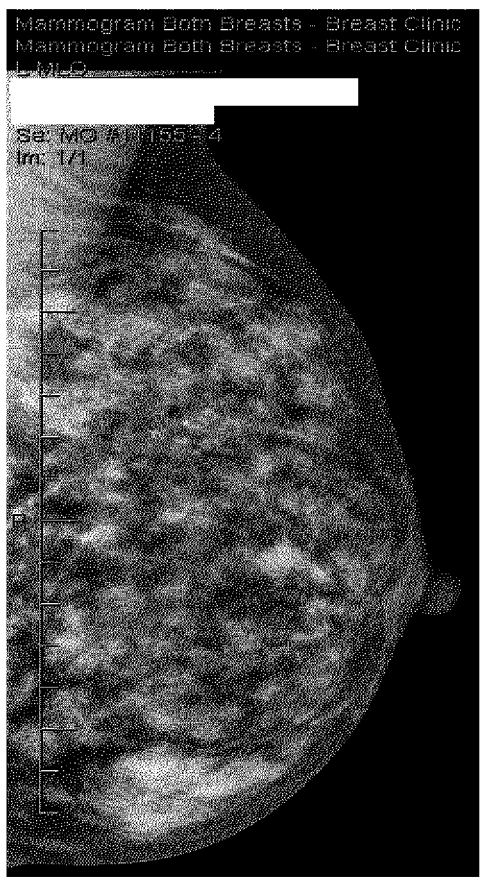

FIG. 16A shows a mammographic image of a 45-year woman who was peri-menopausal pre-treatment, according to an exemplary embodiment.

Figure 16B:
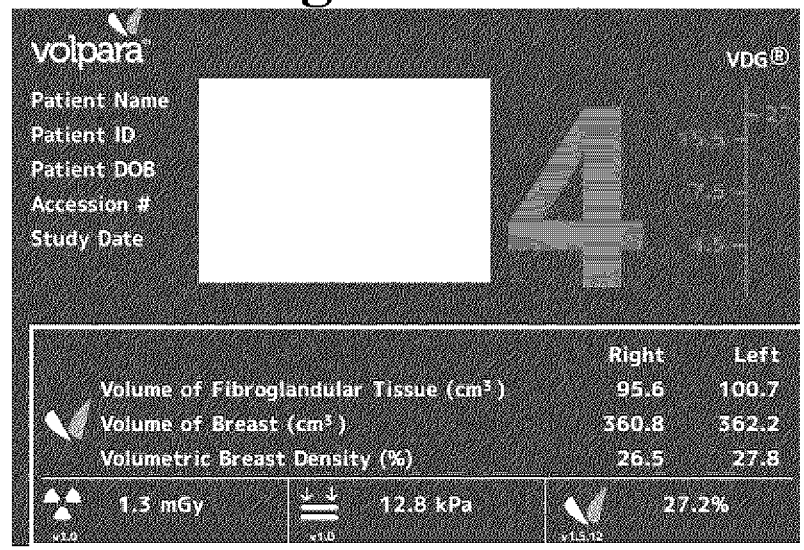

FIG. 16B shows the Volpara Solution™ analysis of the image in FIG. 16A.

Figure 17A:

FIG. 17A shows a mammographic image of the 45-year woman shown in FIG. 16A after approximately 1 year of treatment, according to an exemplary embodiment.

Figure 17B:
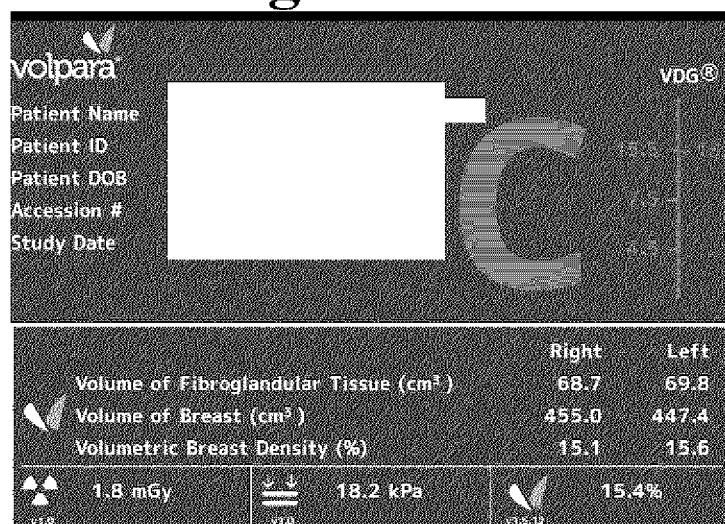

FIG. 17B shows the Volpara Solution™ analysis of the image in FIG. 17A.

Figure 18A:
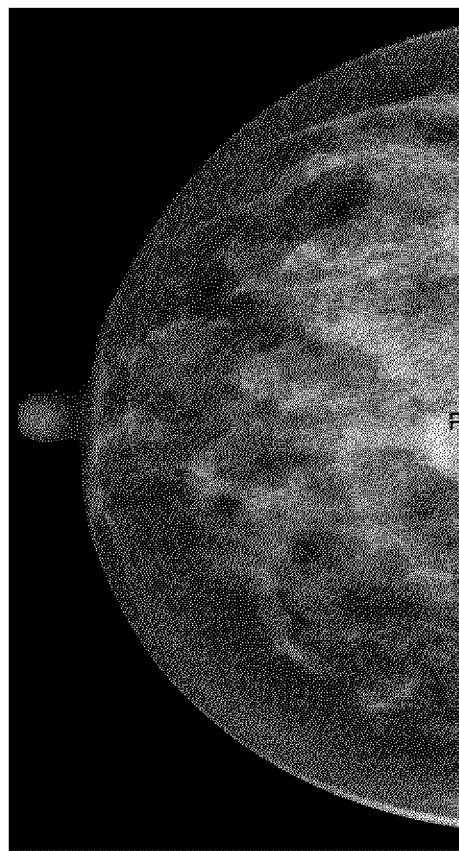

FIG. 18A shows the mammographic image of a 48-year woman who was peri-menopausal pre-treatment, according to an exemplary embodiment.

Figure 18B:
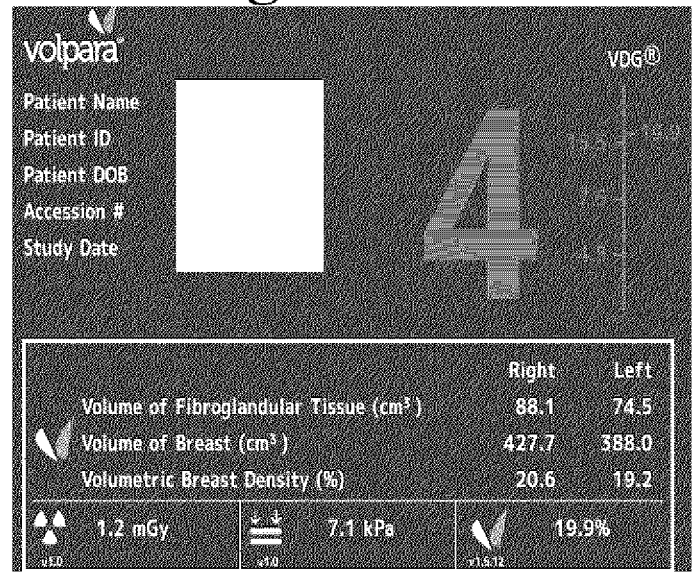

FIG. 18B shows the Volpara Solution™ analysis of the image in FIG. 18A.

Figure 19A:
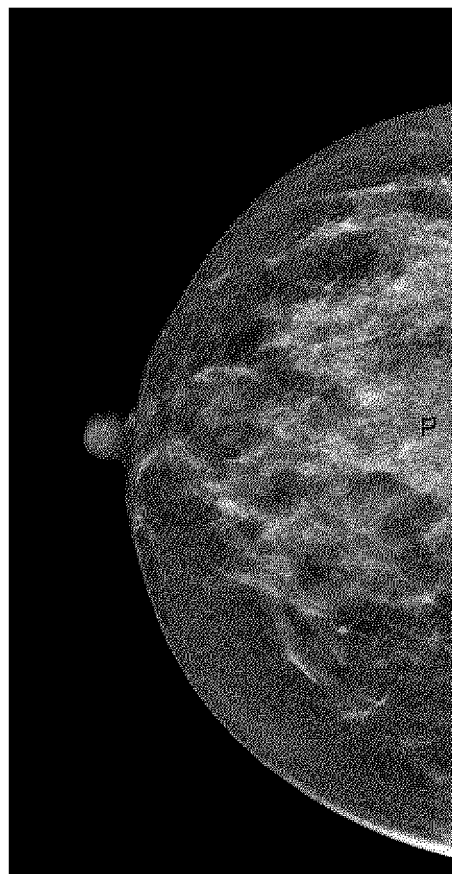

FIG. 19A shows a mammographic image of the 48-year woman shown in FIG. 18A after approximately 1 year of treatment, according to an exemplary embodiment.

Figure 19B:
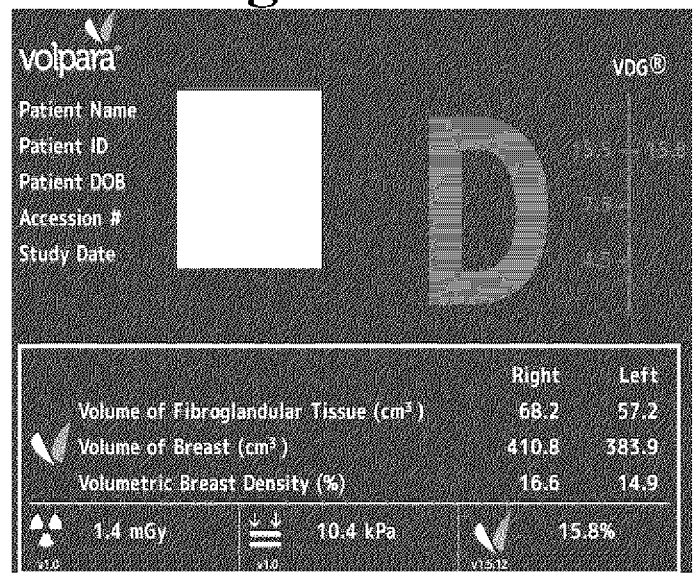

FIG. 19B shows the Volpara Solution™ analysis of the image in FIG. 19A.

Figure 20A:
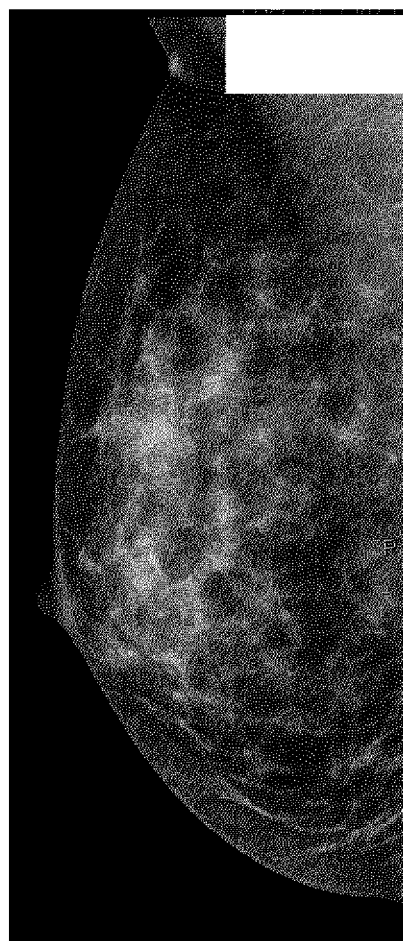

FIG. 20A shows a mammographic image of a 49-year woman who was peri-menopausal pre-treatment.

Figure 20B:
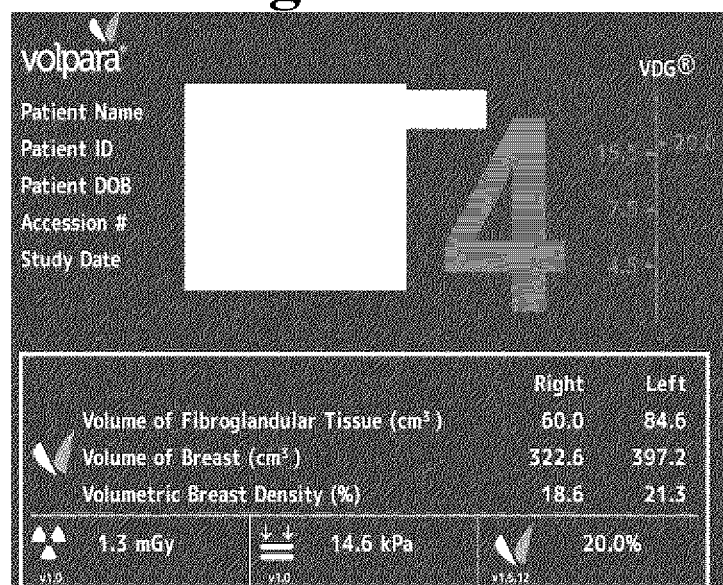

FIG. 20B shows the Volpara Solution™ analysis of the image in FIG. 20A.

Figure 21A:
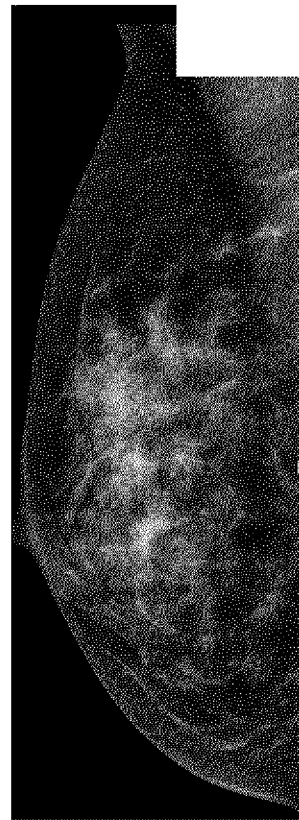

FIG. 21A shows a mammographic image of the 49-year woman shown in FIG. 20A after approximately 1 year of treatment, according to an exemplary embodiment.

Figure 21B:
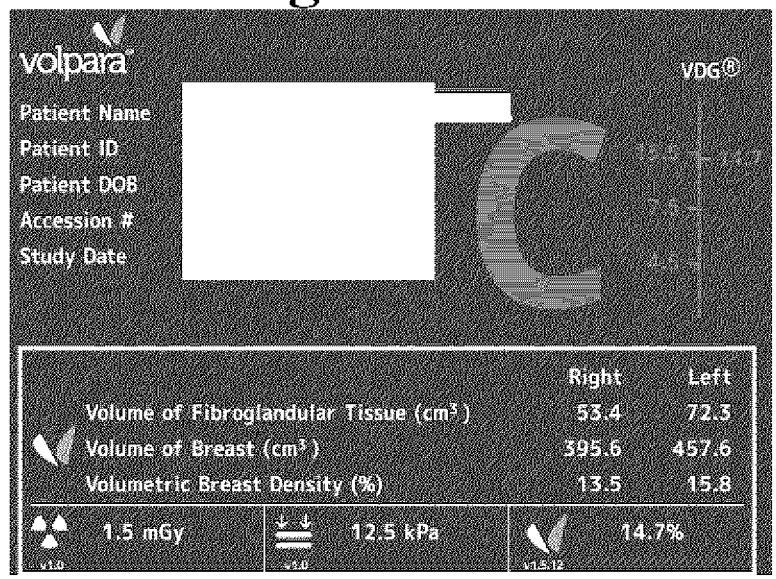

FIG. 21B shows the Volpara Solution™ analysis of the image in FIG. 21A.

Figure 22:
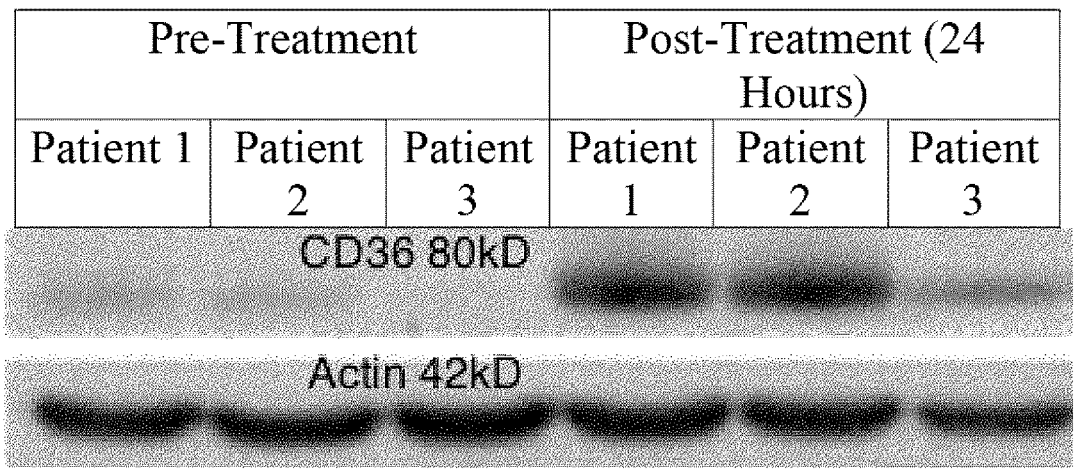

FIG. 22 shows the results of the western blot analysis CD36 protein in 3 explant samples at baseline and after 24 hours of cultivation, according to exemplary embodiments.

Figure 23A:
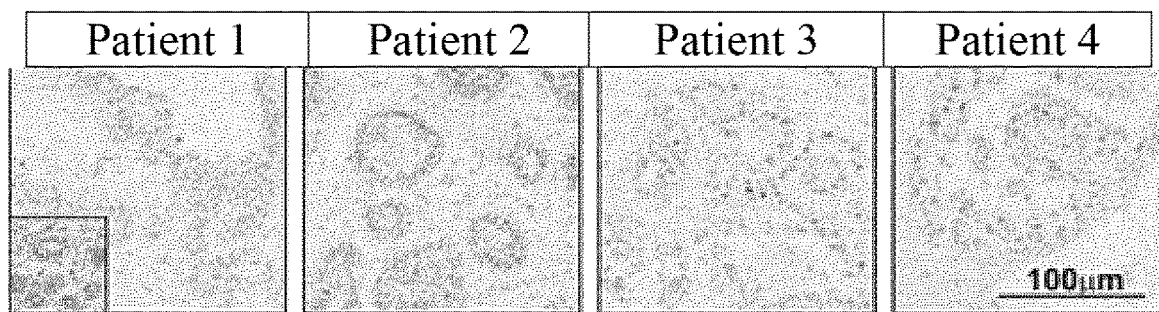

FIG. 23A shows pre-treatment slide samples with an untreated control being observed in the inner lower corner of Patient 1, according to exemplary embodiments.

Figure 23B:
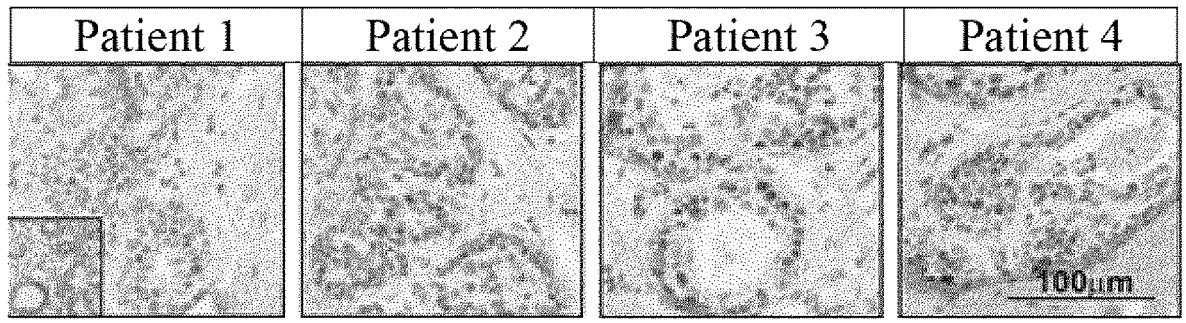

FIG. 23B shows post-treatment slide samples with an untreated control being observed in the inner lower corner of Patient 1, according to exemplary embodiments.

Figure 24A:

FIG. 24A shows the inflamed breast of a patient with macromastia after tamoxifen and oral contraceptive therapy failed to cease the breast growth, according to an exemplary embodiment.

Figure 24B:
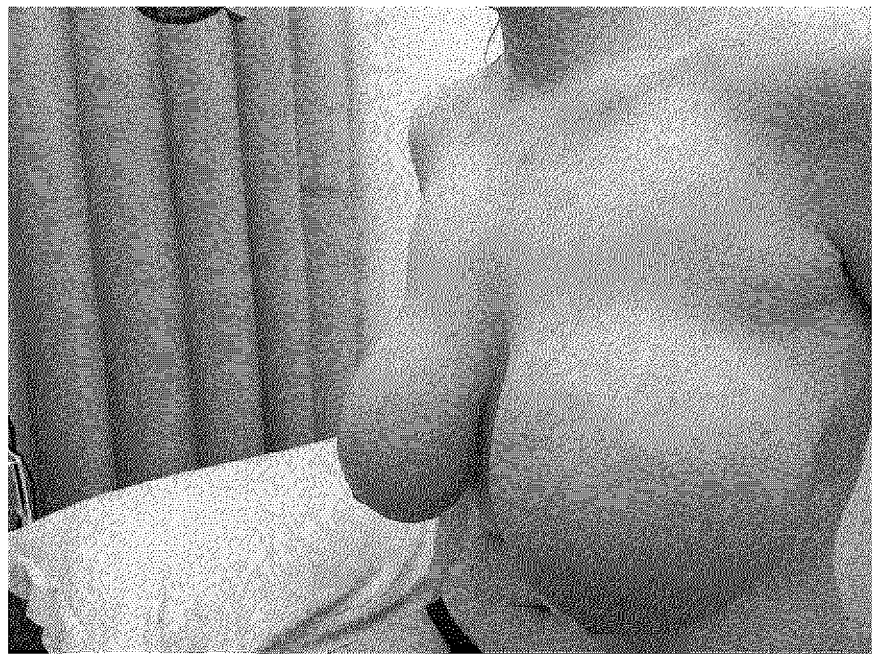

FIG. 24B shows the inflamed breasts after treatment

Figure 24C:

FIG. 24C shows the breast after a surgical reduction mammoplasty was performed.

Figure 25A:
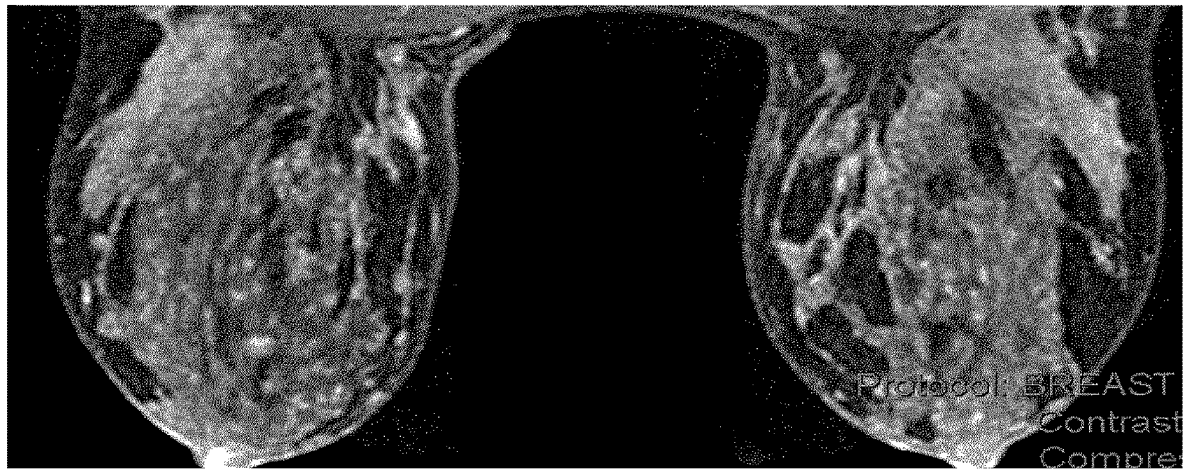

FIG. 25A is an MRI image of a 46 year old pre-menopausal woman's breasts pre-treatment.

Figure 25B:
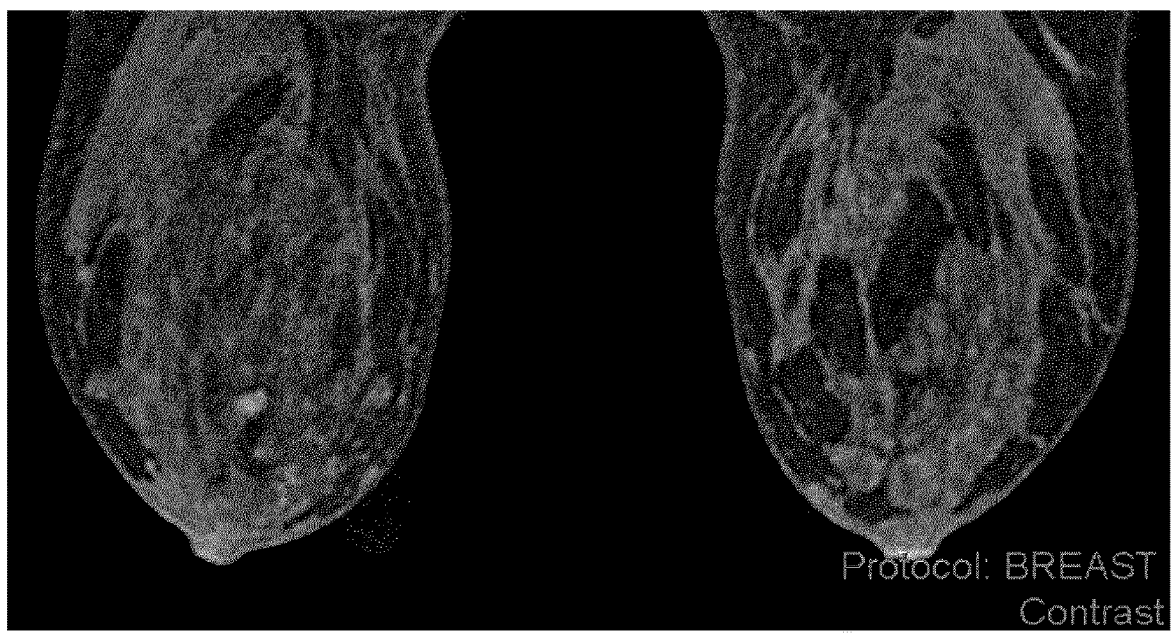

FIG. 25B is an MRI image of the 46 year old pre-menopausal woman's breasts in FIG. 25A after treatment commenced, according to certain embodiments FIG. 26A is a chart showing LH and FSH levels of the pre-menopausal woman, identified in FIGS. 25A and 25B, seven weeks post-treatment.

FIG. 26B is a chart showing LH and FSH levels of the pre-menopausal woman, identified in FIGS. 25A and 25B, twenty-four weeks post-treatment, according to certain embodiments.

Figure 27A:
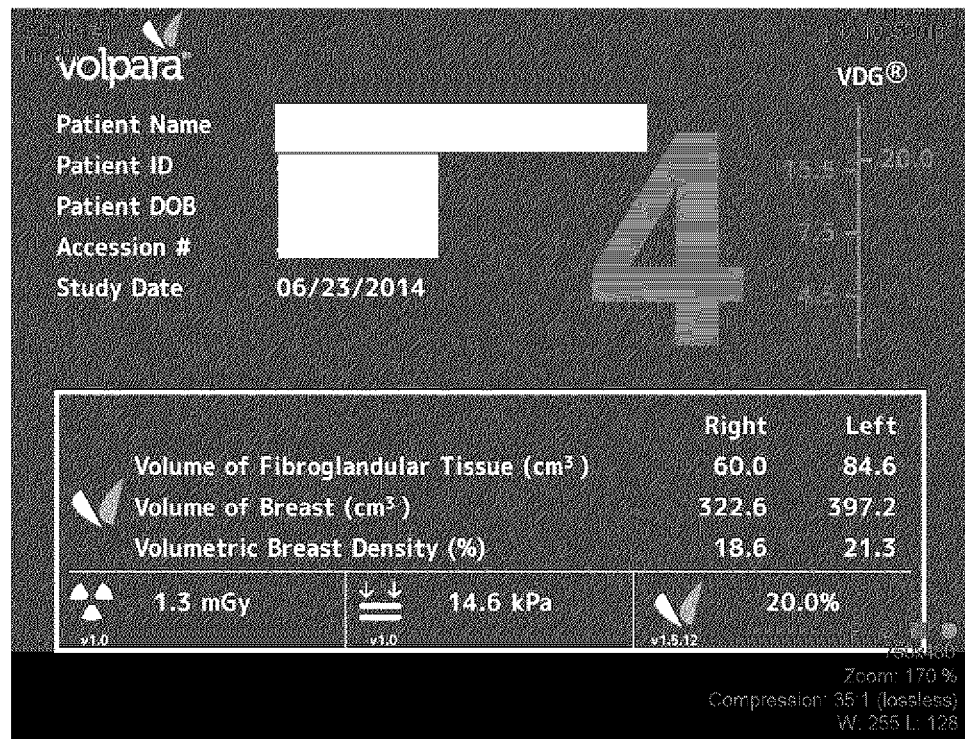

FIG. 27A shows the Volpara Solution™ analysis of the image shown in FIG. 25A.

Figure 27B:
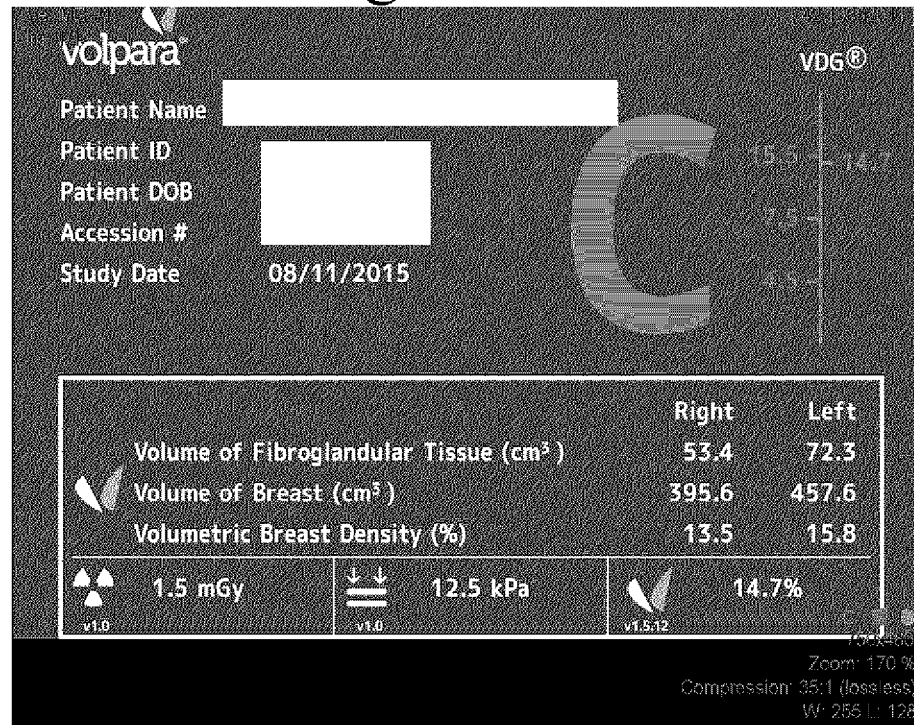

FIG. 27B shows the Volpara Solution™ analysis of the image shown in FIG. 25B.

Figure 28A:
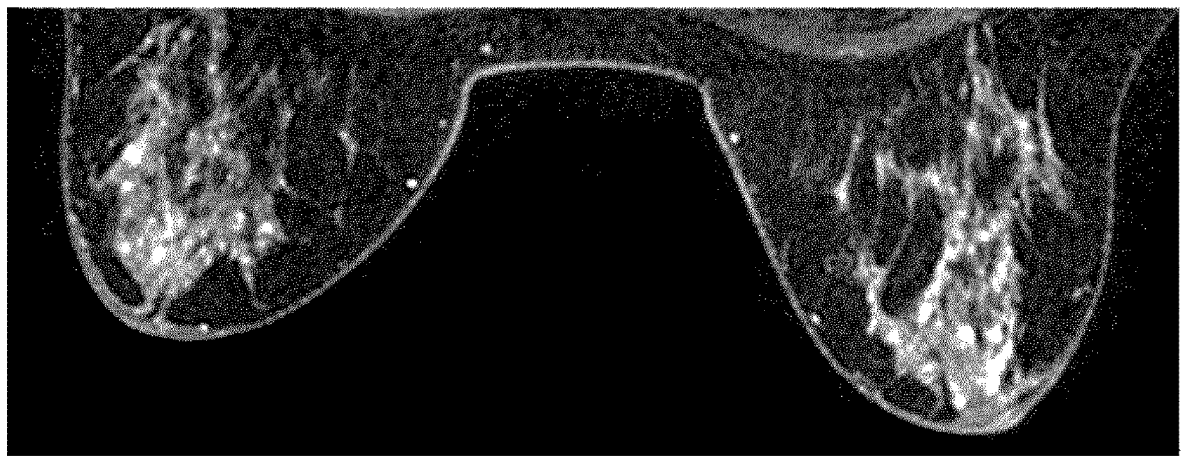

FIG. 28A is an MRI image of a pre-menopausal woman's breasts pre-treatment.

Figure 28B:
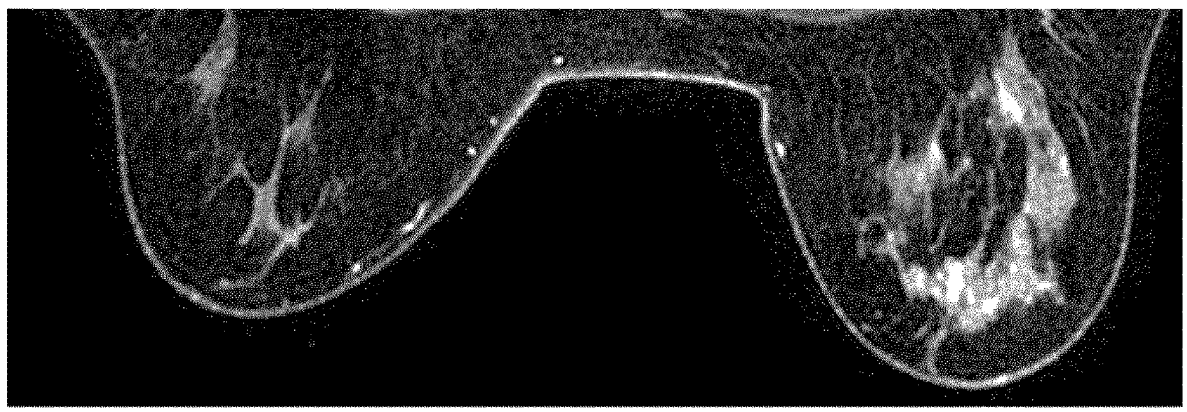

FIG. 28B is an MRI image of the pre-menopausal woman's breasts in FIG. 28A post-treatment, according to certain embodiments.

Figure 29A:
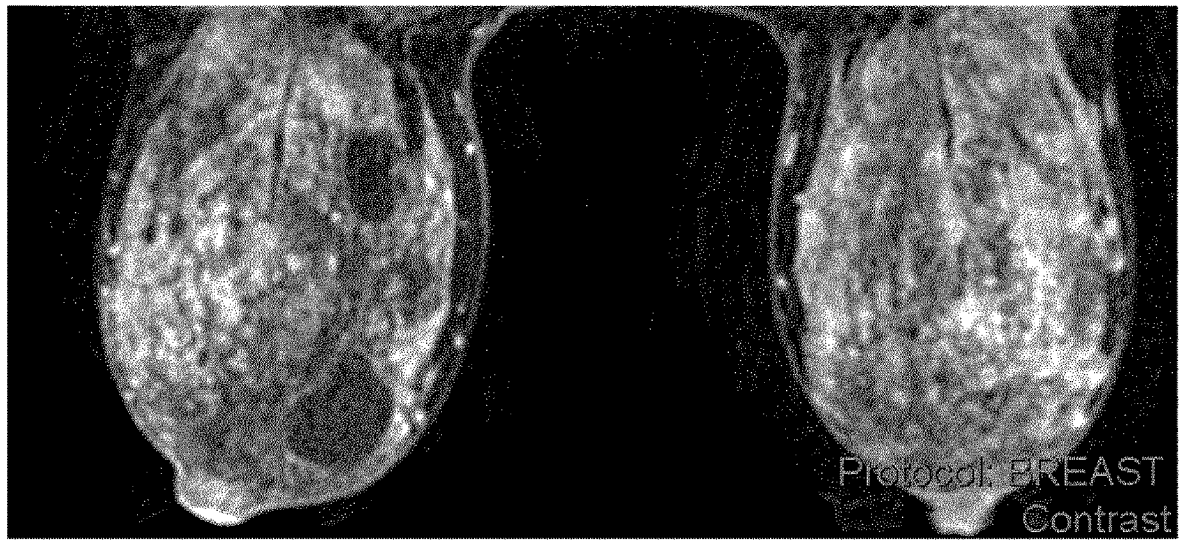

FIG. 29A is an MRI image of a pre-menopausal woman's breasts pre-treatment.

Figure 29B:
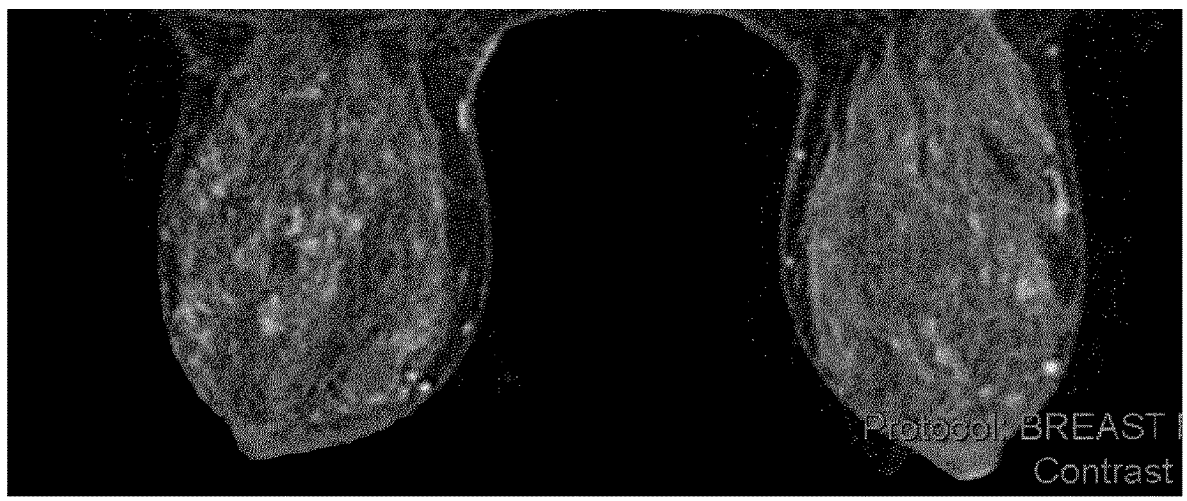

FIG. 29B is an MRI image of the pre-menopausal woman's breasts in FIG. 29A post-treatment, according to certain embodiments.

Figure 30A:

FIG. 30A is an MRI image of a pre-menopausal woman's breasts pre-treatment.

Figure 30B:
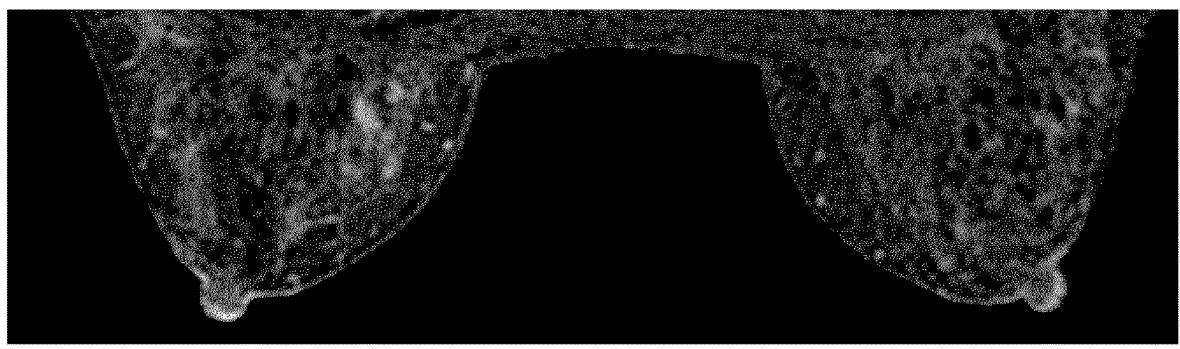

FIG. 30B is an MRI image of the pre-menopausal woman's breasts in FIG. 30A post-treatment, according to certain embodiments.

Figure 31A:

FIG. 31A is an MRI image of a pre-menopausal woman's breasts pre-treatment.

Figure 31B:
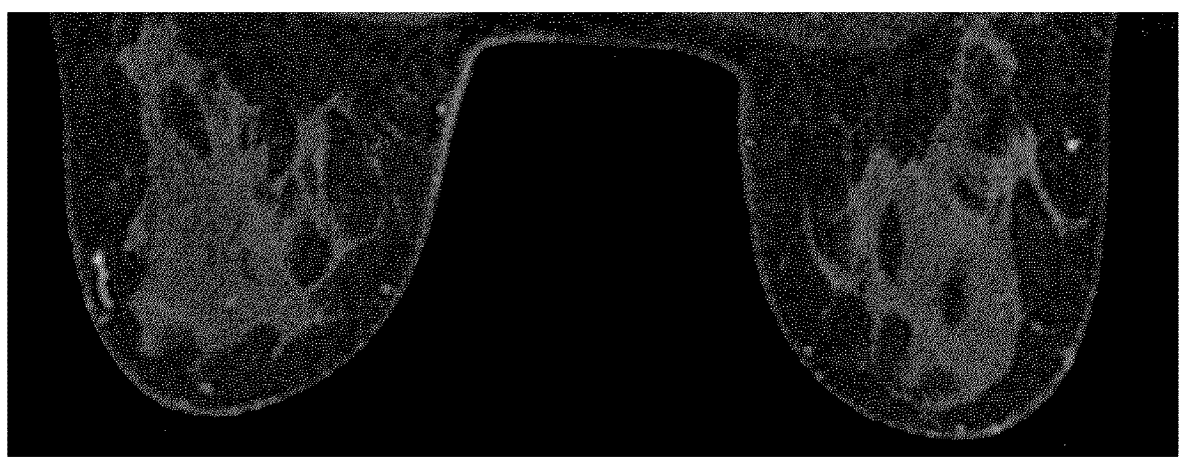

FIG. 31B is an MRI image of the pre-menopausal woman's breasts in FIG. 31A post-treatment, according to certain embodiments.

Figure 32A:
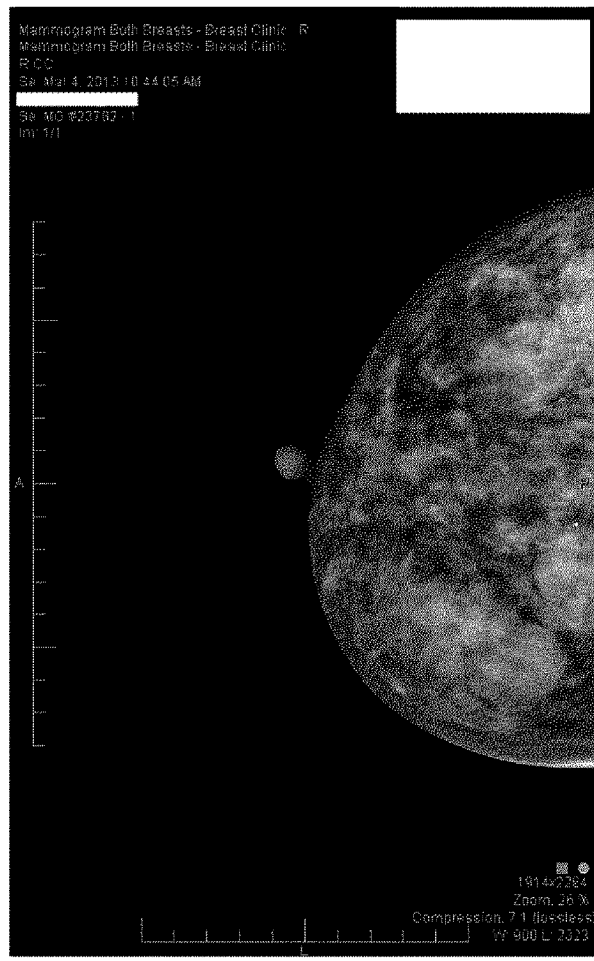

FIG. 32A is a mammogram image of a peri-menopausal woman's breast pre-treatment.

Figure 32B:
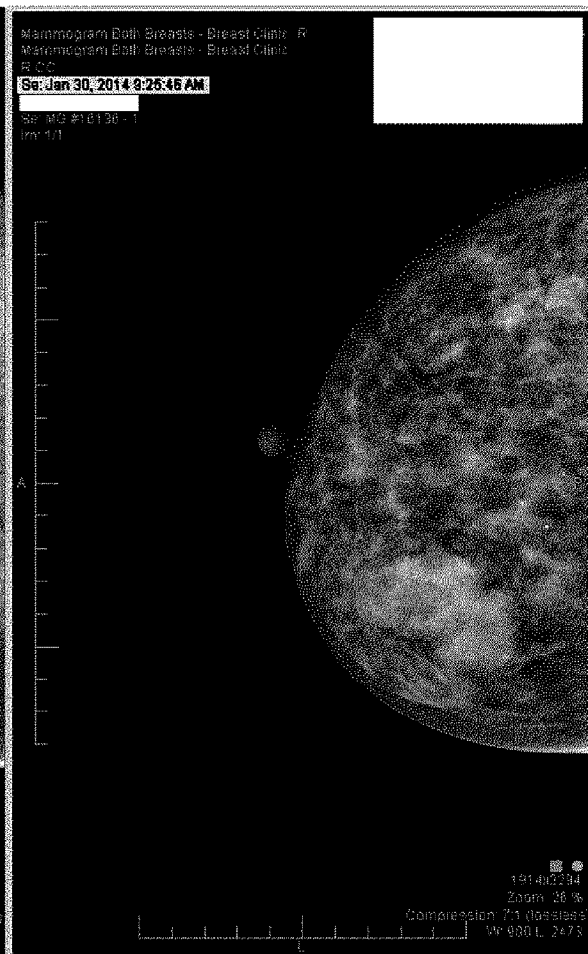

FIG. 32B is a mammogram image of the peri-menopausal woman's breast in FIG. 32A post-treatment, according to certain embodiments.

Figure 33A:

FIG. 33A is a scale used to measure the breast pain of the woman in FIG. 32A pre-treatment.

Figure 33B:

FIG. 33B is a scale used to measure the breast pain of the woman in FIG. 32A after one month of treatment, according to certain embodiments.

Figures 34A, 34B:

FIG. 34A is MRI image of a 45 year old woman with severe breast pain secondary to the inflammation associated with breast cysts pre-treatment.

FIG. 34B is an MRI image of the 45 year old woman in FIG. 34A post-treatment, according to certain embodiments.

Figures 35A, 35B:
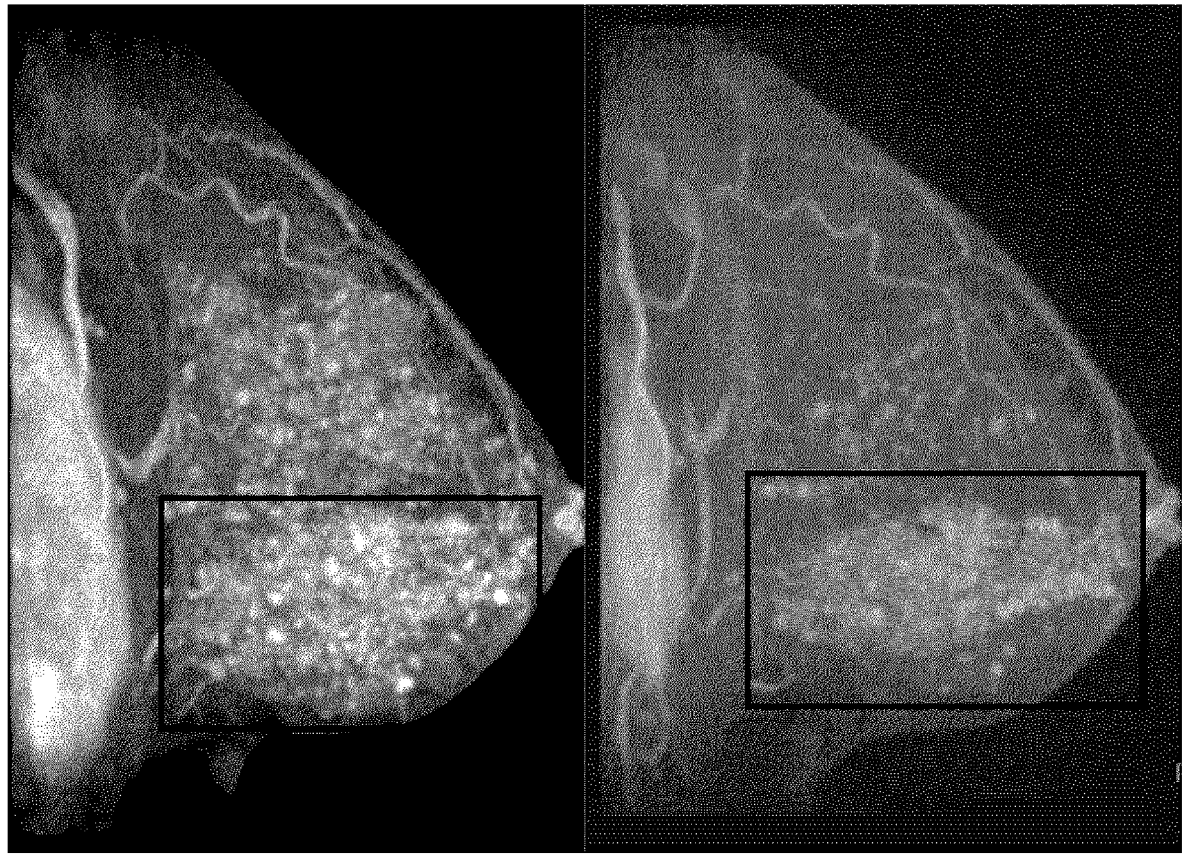

FIG. 35A is an MRI image that shows the BPE of a patient's breast pre-treatment.

FIG. 35B is an MRI image that shows the BPE of a patient's breast after approximately 12 months of treatment, according to certain embodiments.

Figure 36:
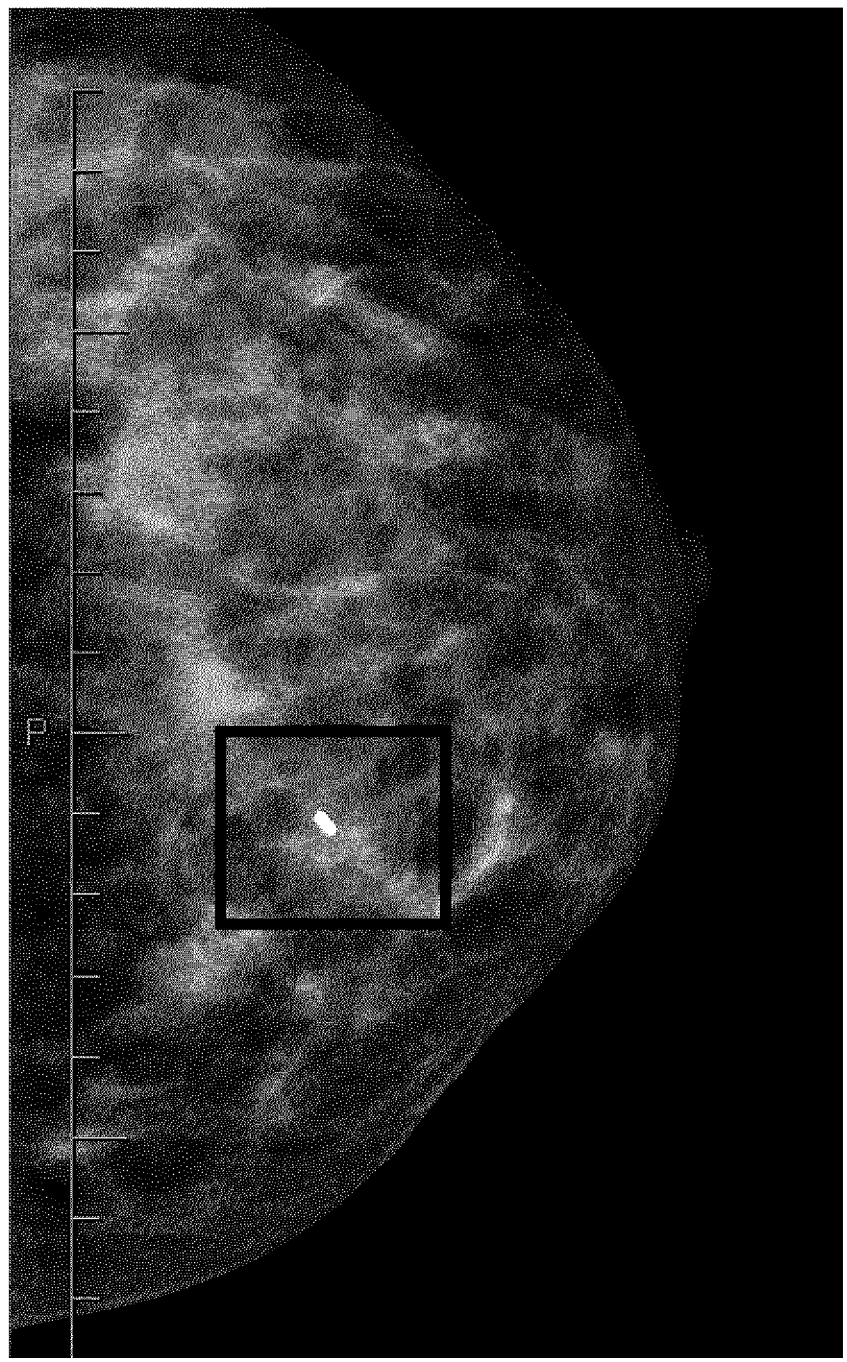

FIG. 36 is a mammogram image of a patient's breast, according to certain embodiments.

DETAILED DESCRIPTION

The following description is provided in relation to several embodiments that may share common characteristics and features. It is to be understood that one or more features of one embodiment may be combined with one or more features of other embodiments. In addition, a single feature or combination of features in certain of the embodiments may constitute additional embodiments. Specific structural and functional details disclosed herein are not to be interpreted as limiting, but merely as a representative basis for teaching one skilled in the art to variously employ the disclosed embodiments and variations of those embodiments.

The subject headings used in the detailed description are included only for the ease of reference of the reader and should not be used to limit the subject matter found throughout the disclosure or the claims. The subject headings should not be used in construing the scope of the claims or the claim limitations.

The present inventors have discovered high breast density and/or breast stiffness is not normal, rather it is pathological; and it is something which may be addressed by effective amounts of an androgenic agent and/or an effective amount of an aromatase inhibitor rather than being treated as a lifestyle modification (e.g. diet exercise) which has not proven to be successful in pre-menopausal, peri-menopausal and/or post-menopausal women. Certain embodiments are directed to methods for identification of mammographically dense breast tissue and/or breast stiffness in pre-menopausal, peri-menopausal and/or post-menopausal women, and methods of providing an intervention composition to reduce this mammographic density and/or breast stiffness.

The present disclosure is directed to a number of methods for affecting mammographic breast density and/or breast stiffness by use in warm blooded animals of an effective amount of androgenic agent and/or an effective amount of an aromatase inhibitor.

The present disclosure is directed to a number of methods for affecting VBD % and/or AVBD and/or breast stiffness by use in warm blooded animals of an effective amount of androgenic agent and/or an effective amount of an aromatase inhibitor.

The present disclosure is directed to a number of methods for affecting ABD % and/or AABD and/or breast stiffness by use in warm blooded animals of an effective amount of androgenic agent and/or an effective amount of an aromatase inhibitor.

Certain of the disclosed embodiments may be used, for example, in a pre-menopausal, peri-menopausal or post-menopausal woman.

The present disclosure is also directed to reducing the risk of breast cancer in warm blooded animals by administering an effective amount of androgenic agent and an effective amount of an aromatase inhibitor to certain warm blooded animals with unacceptable breast density and/or breast stiffness.

Certain embodiments are directed to methods for reducing and/or treating mammographic breast density and/or breast stiffness in a patient in need thereof, without inducing peri-menopausal side effects.

Certain embodiments are directed to methods for reducing and/or treating mammographic breast density (for example, as measured by VBD % and/or AVBD) and/or breast stiffness in a patient in need thereof, without inducing post-menopausal side effects.

Certain embodiments are directed to methods for reducing and/or treating mammographic breast density and/or breast stiffness in a patient in need thereof, wherein the method further decreases the virulence of a breast cancer that develops in the patient.

Certain embodiments are directed to methods for reducing and/or treating mammographic breast density and/or breast stiffness in a patient in need thereof, wherein the method further reduces the progression of a breast cancer that develops in the patient.

Certain embodiments are directed to methods for reducing and/or treating VBD % and/or AVBD and/or breast stiffness in a patient in need thereof, wherein the method further reduces the progression of abnormal proliferation of atypical ductal or lobular breast cells, ductal or lobular carcinoma in situ, invasive breast carcinoma or combinations thereof that develop in the patient.

Certain embodiments are directed to methods for reducing and/or treating ABD % and/or AABD and/or breast stiffness in a patient in need thereof, wherein the method further reduces the progression of abnormal proliferation of atypical ductal or lobular breast cells, ductal or lobular carcinoma in situ, invasive breast carcinoma or combinations thereof that develop in the patient.

Certain embodiments are directed to methods for reducing and/or treating mammographic breast density and/or breast stiffness in a patient in need thereof, wherein the breast density is reduced by at least 20% over a period of 1-5 years or the breast stiffness is reduced by at least 10% over a period of 1-5 years.

Certain embodiments are directed to methods for reducing VBD % and/or AVBD in a patient in need thereof, wherein the VBD % and/or AVBD is reduced by at least 20% over a period of 1-5 years.

Certain embodiments are directed to methods for reducing ABD % and/or AABD in a patient in need thereof, wherein the VBD % and/or AVBD is reduced by at least 20% over a period of 1-5 years.

Certain embodiments are directed to methods for reducing and/or treating mammographic breast stiffness in a patient in need thereof, wherein the breast stiffness is reduced by at least 20% over a period of 1-5 years or the breast stiffness is reduced by at least 10% over a period of 1-5 years.

Certain embodiments are directed to methods for reducing and/or treating mammographic breast density and/or breast stiffness in a patient in need thereof, wherein the breast density is reduced by at least 2%, 5%, 10%, 20%, 30%, 40% or 50% over a period of time.

Certain embodiments are directed to methods for reducing VBD % and/or AVBD in a patient in need thereof, wherein the VBD % and/or AVBD is reduced by at least 2%, 5%, 10%, 20%, 30%, 40% or 50% over a period of time.

Certain embodiments are directed to methods for reducing ABD % and/or AABD in a patient in need thereof, wherein the ABD % and/or AABD is reduced by at least 2%, 5%, 10%, 20%, 30%, 40% or 50% over a period of time.

Certain embodiments are directed to methods for reducing and/or treating mammographic breast stiffness in a patient in need thereof, wherein the breast stiffness is reduced by at least 2%, 5%, 10%, 20%, 30% 40% or 50% over a period of time.

Certain embodiments are directed to methods of reducing mammographic breast density in a patient having a breast with a mammographic breast density of 7.5% or greater.

Certain embodiments are directed to methods of reducing VBD % in a patient having a breast with a VBD % of 7.5% or greater as measured by Volpara Solution™ software.

Certain embodiments are directed to methods of reducing ABD % in a patient having a breast with a ABD % of 7.5% or greater as measured by Culumus Volpara Solution™ software.

Certain embodiments are directed to methods of reducing and/or treating mammographic breast density in a patient having a breast with a BI-RADS® score of 3 or 4 (or c or d).

Certain embodiments are directed to methods of inducing breast involution in a patient in need thereof.

Certain embodiments are directed to methods of inducing net cell death over proliferation in a breast of a patient in need thereof.

Certain embodiments are directed to methods of inducing net extracellular matrix degradation over development of extracellular matrix in a breast of a patient in need thereof.

Certain embodiments are directed to methods of reversing cell number and mammographic breast density in a breast of a peri-menopausal patient.

Certain embodiments are directed to methods of reducing mammographic breast density and peri-menopausal symptoms in a patient in need thereof.

Certain embodiments are directed to methods for reducing and/or treating mammographic breast density and/or breast stiffness in a patient in need thereof, wherein the method increases the visualization of the breast by mammography, digital mammography, magnetic resonance imaging (MRI), ultrasound, digital breast tomosynthesis (DBT), virtual touch tissue imaging quantification (VTIQ), or combinations thereof.

Certain embodiments are directed to methods for reducing VBD % and/or AVBD and/or breast stiffness in a patient in need thereof, wherein the method increases the visualization of the breast by mammography, digital mammography, magnetic resonance imaging (MRI), ultrasound, digital breast tomosynthesis (DBT), virtual touch tissue imaging quantification (VTIQ), or combinations thereof.

Previously it has been shown that increasing breast density results in a reduced ability to detect breast cancer with mammography. A recent presentation by the University of Utrecht at the European Congress of Radiology March 2015 looked at the breast density in the Dutch Screening service (see FIG. 4). Volumetric Density was used with Volpara Solution™ analysis of screening of 69.874 women. There was a large reduction of sensitivity of mammography and almost tripling of false positives recalls for invasive assessment in women with increasing breast density.

Figures 4, 5:
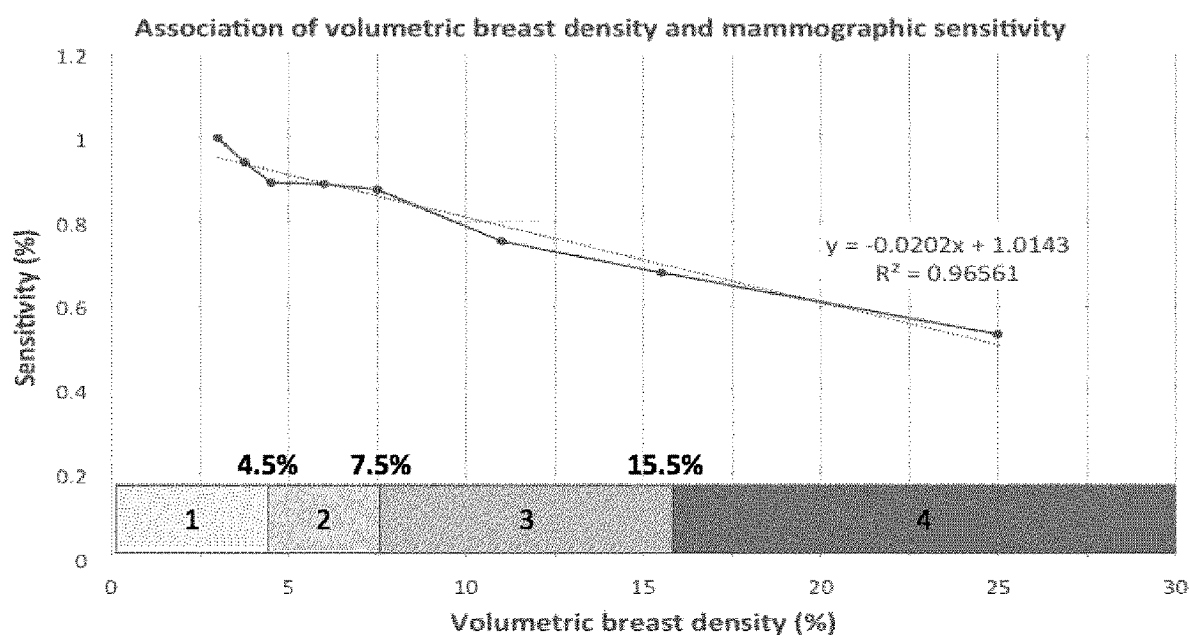
FIG. 4 is a table looking at breast density in a large number of women.
FIG. 5 is a graph showing a relationship between breast density and detection of breast lesions and reduction in false positives.

Certain embodiments reduce AVBD and/or VBD % and as a result increase the sensitivity of detecting breast lesions and reduce the need for unnecessary further work up and/or recall for breast lesions. In example 10, the VBD % reduction was 17%. Applying this 17% reduction to the graph in FIG. 5 shows a 29% improvement in mammographic sensitivity. FIG. 5 is from the recent presentation discussed above. This results in a substantial improvement in sensitivity in the detection of breast lesions and reduction in false positive recall, according to certain embodiments. In example 5, the mean VBD % was reduced from 24.7% to 19.4%. Applying this reduction to the graph in FIG. 5 shows approximately a 17% improvement in mammographic sensitivity. In practical terms, this means that approximately 1 in 6 mammograms have improved sensitivity. This results in a substantial improvement in sensitivity in the detection of breast lesions and reduction in false positive recall, according to certain embodiments.

Certain embodiments are directed to methods for providing an individualized reduction and/or treatment of mammographic breast density and/or breast stiffness in a patient in need thereof, comprising (i) determining the patient's MBD and/or breast stiffness; (ii) optionally, measuring the patient's free androgenic index and/or alterations in the patient's free androgenic index over a period of time of at least one month; (iii) determining adjusted doses of an androgenic agent and/or aromatase inhibitor taking into account the patient's body weight, total body fat, MBD, age, and free androgenic index; and (iv) administering the adjusted dose to said patient. In certain embodiments, the measuring the patient's free androgenic index and/or alterations in the patient's free androgenic index over a period of time of at least one month, may include taking a blood sample and measuring the amount of free androgenic agent (or testosterone) in the patient's serum.

Certain embodiments are directed to methods for providing an individualized reduction of VBD % and/or AVBD and/or breast stiffness in a patient in need thereof, comprising (i) determining the patient's VBD % and/or AVBD and/or breast stiffness; (ii) optionally, measuring the patient's free androgenic index and/or alterations in the patient's free androgenic index over a period of time of at least one month; (iii) determining adjusted doses of an androgenic agent and/or aromatase inhibitor taking into account the patient's body weight, total body fat, VBD % and/or AVBD, age, and free androgenic index; and (iv) administering the adjusted dose to said patient. In certain embodiments, the measuring the patient's free androgenic index and/or alterations in the patient's free androgenic index over a period of time of at least one month, may include taking a blood sample and measuring the amount of free androgenic agent (or testosterone) in the patient's serum.

Certain embodiments are directed to methods for providing an individualized reduction of ABD % and/or AABD and/or breast stiffness in a patient in need thereof, comprising (i) determining the patient's VBD % and/or AVBD and/or breast stiffness; (ii) optionally, measuring the patient's free androgenic index and/or alterations in the patient's free androgenic index over a period of time of at least one month; (iii) determining adjusted doses of an androgenic agent and/or aromatase inhibitor taking into account the patient's body weight, total body fat, ABD % and/or AABD, age, and free androgenic index; and (iv) administering the adjusted dose to said patient. In certain embodiments, the measuring the patient's free androgenic index and/or alterations in the patient's free androgenic index over a period of time of at least one month, may include taking a blood sample and measuring the amount of free androgenic agent (or testosterone) in the patient's serum.

Certain embodiments are directed to methods for reducing and/or treating mammographic breast density and/or breast stiffness in a patient in need thereof, wherein the method increases sensitivity of breast imaging detections by mammography, digital mammography, magnetic resonance imaging (MRI), ultrasound, digital breast tomosynthesis (DBT), virtual touch tissue imaging quantification (VTIQ), or combinations thereof.

Certain embodiments are directed to methods for reducing and/or treating mammographic breast density and/or breast stiffness in a patient in need thereof, wherein the method increases detection of breast cancer developing in the patient.

Certain embodiments are directed to methods for reducing and/or treating VBD % and/or AVBD and/or breast stiffness in a patient in need thereof, wherein the method increases detection of breast cancer developing in the patient.

Certain embodiments are directed to methods for reducing and/or treating ABD % and/or AABD and/or breast stiffness in a patient in need thereof, wherein the method increases detection of breast cancer developing in the patient.

The methods disclosed herein may be used to effect one or more of the following in a patient: reducing mammographic breast density, treating mammographic breast density; reducing breast stiffness; treating breast stiffness; reducing mammographic breast density in a patient having a breast with a mammographic breast density of 7.5% or greater; reducing mammographic breast density in a patient having a breast with a BI-RADS® score of 3 or 4 (or c or d); inducing breast involution in a patient; inducing net cell death over proliferation in a breast of a patient; inducing net extracellular matrix degradation over development of extracellular matrix in a breast of a patient; methods of reversing cell number and mammographic breast density in a breast of a peri-menopausal patient; and reducing mammographic breast density and peri-menopausal symptoms in a patient. These methods may be useful in pre-menopausal and/or peri-menopausal woman. These methods may also be useful in post-menopausal woman.

For example, high breast density in peri-menopause woman is known as a risk for developing breast cancer. The dense tissue in peri-menopausal women is not consider normal and has pathological implications. This increase in breast density may be due to a lifelong exposure to high levels of estrogen and progesterone in the presence of a low testosterone environment. The present inventors have discovered, among other things, that pre-menopausal, peri-menopausal and/or post-menopausal woman who receive effective amounts of an androgenic agent such as testosterone and effective amounts of an aromatase inhibitor (such as anastrozole) may show a reduction in breast density and/or breast stiffness. The present inventors have also discovered that pre-menopausal, peri-menopausal and/or post-menopausal woman who receive effective amounts of testosterone and effective amounts of an aromatase inhibitor (such as anastrozole) may show an induction of breast involution and/or net cell death over proliferation. The present inventors have also discovered that an effective amount of an aromatase inhibitor in the breast tissue may be used to stop the conversion of testosterone to estrogen and thus allow testosterone to invoke an involution of the breast cells.

One or more of the following advantages is found in one or more of the disclosed methods.

A. Enhanced mammographic detection due to reduced breast density enabling the mammogram to visualize malignancy at an earlier and/or less aggressive stage.

B. Reduced risk of interval breast cancer, such as those that may occur between mammographic screening rounds. These cancers are common in breasts with high MBD.

C. Reduction in breast stiffness.

D. Reduced pain during mammographic breast compression.

E. Ability to achieve better mammographic compression due at least in part to reduced pain.

F. Because better mammographic compression is achieved and that the breast tissue is less dense the amount of energy required to expose the image on the mammogram is therefore reduced thus reducing the radiation of the breast tissue. Reducing the risk of radiation induced breast cancer.

G. Ability to achieve better patient compliance in having regular mammographic check-ups.

H. Ability to treat patient and at the same time not causing perturbations in the hypothalamic-pituitary axis and/or other endocrine axis.

I. Reduced breast pain in a patient.

J. Reduced breast elasticity in a patient.

K. Decreased mechano-transduction on the genome of a cell in order to reduce the risk of malignant transformation in a patient.

L. Increased ratio of fibro-glandular and adipose tissue in a patient.

M. Increased CD36 in a patient.

N. Stabilization and/or an increase in levels of androgen receptor expression in breast tissue of a patient.

O. Treatment of macromastia in a patient.

P. Increased GCDFP15 in a patient.

Q. Reduced BPE in an MRI image of a patient.

R. Reduction in the size and/or quantity of cysts in a patient.

S. Reduce the risk of breast cancer.

There are a number of categories used by diagnosticians and physicians to characterize the type and/or degree of mammographic breast density of a breast of a patient.

A diagnosing or treating physician may use one or more exams/tests to evaluate, characterize, and/or diagnose, a breast density, including but not limited to, mammography, digital mammography, magnetic resonance imagery (MRI), ultrasound, digital breast tomosynthesis (DBT), virtual touch tissue imaging quantification (VTIQ), or combinations thereof. The physician may also use other indicia, such as medical history or family history (to account for a genetic predisposition to breast density), and/or qualitative assessments of MBD, such as BI-RADS® (e.g., $5^{th}$ edition, using Breast Composition categories of "a" (the breasts are almost entirely fatty), "b" (there are scattered areas of fibro-glandular density), "c" (the breasts are heterogeneously dense, which may obscure small masses), and "d" (the breasts are extremely dense, which lowers the sensitivity of mammography) (D'Orsi C J, Sickles E A, Mendelson E B, Morris E A et al. (2013). *ACR BI-RADS® Atlas, Breast Imaging Reporting and Data System*. Reston, Va.: American College of Radiology).

Breast pain is a significant problem in female health. Breast pain is also associated with increases in VBD % and/or AVBD, breast stiffness, the risk of breast cancer or combinations thereof. Certain embodiments are directed to the use of an androgen agent and an aromatase inhibitor to reduce the breast pain in a patient.

Certain embodiments are directed to the use of androgenic agent combined with an aromatase inhibitor to reduce pain and/or breast size in macromastia patients.

Certain embodiments are directed to the use of an androgenic agent in combination with an aromatase inhibitor to increase the level of GCDFP15 in woman with at least 7.5% VBD % using Volpara Solution™ software. By increasing the level of GCDFP15 in such woman there is a beneficial immune-modulation of the breast tissue. This immune-modulation of breast tissue will reduce the risk of breast cancer in such woman. The treatment to increase the level of GCDFP15 and/or reduce the VBD % may be used in pre-menopausal, peri-menopausal, menopausal or post-menopausal woman with at least 7.5 VBD % using Volpara Solution™ software. The treatment to increase the level of GCDFP15 and/or reduce the VBD % may be used in pre-menopausal, peri-menopausal, menopausal or post-menopausal woman with at least moderate breast density using BI-RADS scoring system.

In exemplary embodiments, a patient is provided an aromatase inhibitor of 0.5-10 mg anastrozole (2,2'-[5-(1H-1,2,4-triazol-1-ylmethyl)-1,3-phenylene]bis(2-methylpropanenitrile)) orally as a tablet or other appropriate delivery system once a day in combination with at least one of the following amounts of an Arl propionamide androgenic agent such as (2S)-3-(4-cyanophenoxy)-N-[4-cyano-3-(trifluoromethyl)phenyl]-2-hydroxy-2-methylpropanamide (also known as Enobosarm, Ostarine, GTx-024, and MK-2866), 3, 6, 9, 12, 15 or 18 mg orally as a tablet or other appropriate delivery system once a day. In exemplary embodiments, the androgenic agent provided once a day may vary between 0.5 mg to 20 mg, between 3 mg to 9 mg, between 6 mg to 15 mg or between 6 mg to 12 mg. The duration of treatment for administration of the androgenic agent and the aromatase inhibitor, or a pharmaceutical composition or a combination of the same, may vary between about 2 weeks to about 4 weeks, 3 months to about 3 years, may vary between about 3 months to about 3 years, between about 6 months to about 2 years, between about 3 months to about 5 years, between about 1 year and about 5 years and between about 1 year to about 2 years. In certain embodiments, the duration of treatment may be about 2 weeks, about 3 months, about 6 months, about 9 months, about 1 year, about 1.5 years, about 2 years, about 2.5 years or about 3 years. In certain embodiments, the duration of treatment may be at least 2 weeks, 3 months, 6 months, 9 months, 1 year, 1.5 years, 2 years, 3 year or 4 years. The treatment may be applied to one or more of the following: a reduction in ABD %, a reduction in AABD, a reduction in VBD %; a reduction in AVBD; a reduction in breast pain; a reduction in breast stiffness; a reduction in breast elasticity; a reduction in macromastia; a reduction in breast cysts; an improvement in mammographic diagnostic sensitivity and a reduction in false positives; an increase in the ratio between fibro-glandular and adipose tissue; a stabilization and/or an increase in levels of androgen receptor expression; and an increase in GCDFP15.

In exemplary embodiments, a patient is provided an aromatase inhibitor of 0.5-20 mg letrozole (4,4'-((1H-1,2,4-triazol-1 yl)methylene)dibenzonitrile) orally as a tablets or other appropriate delivery system once a day, and in combination with at least one of the following amounts of an Arl propionamide androgenic agent such as (2S)-3-(4-cyanophenoxy)-N-[4-cyano-3-(trifluoromethyl)phenyl]-2-hydroxy-2-methylpropanamide (also known as Enobosarm, Ostarine, GTx-024, and MK-2866), 3, 6, 9, 12, 15 or 18 mg orally as a tablet or other appropriate delivery system once a day. In exemplary embodiments, the androgenic agent provided once a day may vary between 0.5 mg to 20 mg, between 3 mg to 9 mg, between 6 mg to 15 mg or between 6 mg to 12 mg. The duration of treatment for administration of the androgenic agent and the aromatase inhibitor, or a pharmaceutical composition a combination of the same, may vary between about 2 weeks to about 4 weeks, may vary between about 3 months to about 3 years, between about 6 months to about 2 years, between about 3 months to about 5 years, between about 1 year and about 5 years and between about 1 year to about 2 years. In certain embodiments, the duration of treatment may be about 2 weeks, 3 months, 6 months, about 9 months, about 1 year, about 1.5 years, about 2 years, about 2.5 years or about 3 years. In certain embodiments, the duration of treatment may be at least 2 weeks, 3 months, 6 months, 9 months, 1 year, 1.5 years, 2 years, 3 year or 4 years. The treatment may be applied to one or more of the following: a reduction in ABD %, a reduction in AABD, a reduction in VBD %; a reduction in AVBD; a reduction in breast pain; a reduction in breast stiffness; a reduction in breast elasticity; a reduction in macromastia; a reduction in breast cysts; an improvement in mammographic diagnostic sensitivity and a reduction in false positives; an increase in the ratio between fibro-glandular and adipose tissue; a stabilization and/or an increase in levels of androgen receptor expression; and an increase in GCDFP15.

In exemplary embodiments, a patient is provided an aromatase inhibitor of exemestane 10-75 mg 6-Methylideneandrosta-1,4-diene-3,17-dione orally as a tablet or other appropriate delivery system once a day, and in combination with at least one of the following amounts of an Arl propionamide androgenic agent such as (2S)-3-(4-cyanophenoxy)-N-[4-cyano-3-(trifluoromethyl)phenyl]-2-hydroxy-2-methylpropanamide (also known as Enobosarm, Ostarine, GTx-024, and MK-2866), 3, 6, 9, 12, 15 or 18 mg orally as a tablet or other appropriate delivery system once a day. In exemplary embodiments, the androgenic agent provided once a day may vary between 0.5 mg to 20 mg, between 3 mg to 9 mg, between 6 mg to 15 mg or between 6 mg to 12 mg. The duration of treatment for administration of the androgenic agent and the aromatase inhibitor, or a pharmaceutical composition or a combination of the same, may vary between about 2 weeks to about 4 weeks, may vary between about 3 months to about 3 years, between about 6 months to about 2 years, between about 3 months to about 5 years, between about 1 year and about 5 years and between about 1 year to about 2 years. In certain embodiments, the duration of treatment may be about 2 weeks, about 3 months, about 6 months, about 9 months, about 1 year, about 1.5 years, about 2 years, about 2.5 years or about 3 years. In certain embodiments, the duration of treatment may be at least 2 weeks, 3 months, 6 months, 9 months, 1 year, 1.5 years, 2 years, 3 year or 4 years. The treatment may be applied to one or more of the following: a reduction in ABD %, a reduction in AABD, a reduction in VBD %; a reduction in AVBD; a reduction in breast pain; a reduction in breast stiffness; a reduction in breast elasticity; a reduction in macromastia; a reduction in breast cysts; an improvement in mammographic diagnostic sensitivity and a reduction in false positives; an increase in the ratio between fibro-glandular and adipose tissue; a stabilization and/or an increase in levels of androgen receptor expression; and an increase in GCDFP15.

In exemplary embodiments, a patient is provided an aromatase inhibitor of 1 mg anastrozole (2,2'-[5-(1H-1,2,4-triazol-1-ylmethyl)-1,3-phenylene]bis(2-methylpropanenitrile)) orally as a tablet or other appropriate delivery system once a day in combination with at least one of the following amounts of a Quinolinone androgenic agent such as (4-((R)-2-((R)-2,2,2-trifluoro-1-hydroxyethyl)pyrrolidin-1-yl)-2-trifluoromethyl)benzonitrile (also known as LGD-4033, or Ligandrol), 0.1, 0.3, 0.5, 0.75 or 1 mg orally as a tablet or other appropriate delivery system once a day. In exemplary embodiments, the androgenic agent provided once a day may vary between 0.05 mg to 2 mg, between 0.3 mg to 0.9 mg, between 0.2 mg to 0.75 mg or between 0.3 mg to 1 mg. The duration of treatment for administration of the androgenic agent and the aromatase inhibitor, or a pharmaceutical composition a combination of the same, may vary between about 2 weeks to about 4 weeks may vary between about 3 months to about 3 years, between about 6 months to about 2 years, between about 3 months to about 5 years, between about 1 year and about 5 years and between about 1 year to about 2 years. In certain embodiments, the duration of treatment may be about 2 weeks, about 3 months, 6 about months, about 9 months, about 1 year, about 1.5 years, about 2 years, about 2.5 years or about 3 years. In certain embodiments, the duration of treatment may be at least 2 weeks, 3 months, 6 months, 9 months, 1 year, 1.5 years, 2 years, 3 year or 4 years. The treatment may be applied to one or more of the following; a reduction in VBD %; a reduction in AVBD; a reduction in breast pain; a reduction in breast stiffness; a reduction in breast elasticity; a reduction in macromastia; a reduction in breast cysts; an improvement in mammographic diagnostic sensitivity and a reduction in false positives; an increase in the ratio between fibro-glandular and adipose tissue; a stabilization and/or an increase in levels of androgen receptor expression; and an increase in GCDFP15.

In exemplary embodiments, a patient is provided an aromatase inhibitor of 2.5 mg letrozole (4,4'-((1H-1,2,4-triazol-1 yl)methylene)dibenzonitrile) orally as a tablet or other appropriate delivery system once a day in combination with at least one of the following amounts of a Quinolinone androgenic agent such as (4-((R)-2-((R)-2,2,2-trifluoro-1-hydroxyethyl)pyrrolidin-1-yl)-2-trifluoromethyl)benzonitrile (also known as LGD-4033, or Ligandrol), 0.1, 0.3, 0.5, 0.75 or 1 mg orally as a tablet or other appropriate delivery system once a day. In exemplary embodiments, the androgenic agent provided once a day may vary between 0.05 mg to 2 mg, between 0.3 mg to 0.9 mg, between 0.2 mg to 0.75 mg or between 0.3 mg to 1 mg. The duration of treatment for administration of the androgenic agent and the aromatase inhibitor, or a pharmaceutical composition or a combination of the same, may vary between about 2 weeks to about 4 weeks, between about 6 months to about 2 years, between about 3 months to about 5 years, between about 1 year and about 5 years and between about 1 year to about 2 years. In certain embodiments, the duration of treatment may be about 2 weeks, 3 about months, 6 about months, about 9 months, about 1 year, about 1.5 years, about 2 years, about 2.5 years or about 3 years. In certain embodiments, the duration of treatment may be at least 2 weeks, 3 months, 6 months, 9 months, 1 year, 1.5 years, 2 years, 3 year or 4 years. The treatment may be applied to one or more of the following: a reduction in ABD %, a reduction in AABD, a reduction in VBD %; a reduction in AVBD; a reduction in breast pain; a reduction in breast stiffness; a reduction in breast elasticity; a reduction in macromastia; a reduction in breast cysts; an improvement in mammographic diagnostic sensitivity and a reduction in false positives; an increase in the ratio between fibro-glandular and adipose tissue; a stabilization and/or an increase in levels of androgen receptor expression; and an increase in GCDFP15.

In exemplary embodiments, a patient is provided an aromatase inhibitor of exemestane 25 mg 6-Methylideneandrosta-1,4-diene-3,17-dione orally as a tablet or other appropriate delivery system once a day in combination with at least one of the following amounts of a Quinolinone androgenic agent such as (4-((R)-2-((R)-2,2,2-trifluoro-1-hydroxyethyl)pyrrolidin-1-yl)-2-trifluoromethyl)benzonitrile (also known as LGD-4033, or Ligandrol), 0.1, 0.3, 0.5, 0.75 or 1 mg orally as a tablet or other appropriate delivery system once a day. In exemplary embodiments, the androgenic agent provided once a day may vary between 0.05 mg to 2 mg, between 0.3 mg to 0.9 mg, between 0.2 mg to 0.75 mg or between 0.3 mg to 1 mg. The duration of treatment for administration of the androgenic agent and the aromatase inhibitor, or a pharmaceutical composition or a combination of the same, may vary between about 2 weeks to about 4 weeks, between about 6 months to about 2 years, between about 3 months to about 5 years, between about 1 year and about 5 years and between about 1 year to about 2 years. In certain embodiments, the duration of treatment may be about 2 weeks, 3 about months, about 6 months, about 9 months, about 1 year, about 1.5 years, about 2 years, about 2.5 years or about 3 years. In certain embodiments, the duration of treatment may be at least 2 weeks, 3 months, 6 months, 9 months, 1 year, 1.5 years, 2 years, 3 year or 4 years. The treatment may be applied to one or more of the following: a reduction in ABD %, a reduction in AABD, a reduction in VBD %; a reduction in AVBD; a reduction in breast pain; a reduction in breast stiffness; a reduction in breast elasticity; a reduction in macromastia; a reduction in breast cysts; an improvement in mammographic diagnostic sensitivity and a reduction in false positives; an increase in the ratio between fibro-glandular and adipose tissue; a stabilization and/or an increase in levels of androgen receptor expression; and an increase in GCDFP15.

In exemplary embodiments, a patient is provided an aromatase inhibitor of 1 mg anastrozole (2,2'-[5-(1H-1,2,4-triazol-1-ylmethyl)-1,3-phenylene]bis(2-methylpropanenitrile)) orally as a tablet or other appropriate delivery system once a day in combination with at least one of the following amounts of a Hydantoin androgenic agent such as (4-[(7R,7aS)-7-hydroxy-1,3-dioxo-5,6,7,7a-tetrahydropyrrolo[1,2-c]imidazol-2-yl]-2-chloro-3-methylbenzonitrile (also known BMS-564929), 5, 10, 15 or 20 mg orally as a tablet or other appropriate delivery system once a day. In exemplary embodiments, the androgenic agent provided once a day may vary between 0.5 mg to 20 mg, between 3 mg to 9 mg, between 6 mg to 15 mg or between 6 mg to 12 mg. The duration of treatment for administration of the androgenic agent and the aromatase inhibitor, or a pharmaceutical composition or a combination of the same, may vary between about 2 weeks to about 4 weeks, between about 6 months to about 2 years, between about 3 months to about 5 years, between about 1 year and about 5 years and between about 1 year to about 2 years. In certain embodiments, the duration of treatment may be about 2 weeks, about 3 months, about 6 months, about 9 months, about 1 year, about 1.5 years, about 2 years, about 2.5 years or about 3 years. In certain embodiments, the duration of treatment may be at least 2 weeks, 3 months, 6 months, 9 months, 1 year, 1.5 years, 2 years, 3 year or 4 years. The treatment may be applied to one or more of the following: a reduction in ABD %, a reduction in AABD, a reduction in VBD %; a reduction in AVBD; a reduction in breast pain; a reduction in breast stiffness; a reduction in breast elasticity; a reduction in macromastia; a reduction in breast cysts; an improvement in mammographic diagnostic sensitivity and a reduction in false positives; an increase in the ratio between fibro-glandular and adipose tissue; a stabilization and/or an increase in levels of androgen receptor expression; and an increase in GCDFP15.

In exemplary embodiments, a patient is provided an aromatase inhibitor of 2.5 mg letrozole (4,4'-((1H-1,2,4-triazol-1 yl)methylene)dibenzonitrile) orally as a tablet or other appropriate delivery system once a day in combination with at least one of the following amounts of a Hydantoin androgenic agent such as (4-[(7R,7aS)-7-hydroxy-1,3-dioxo-5,6,7,7a-tetrahydropyrrolo[1,2-c]imidazol-2-yl]-2-chloro-3-methylbenzonitrile (also known BMS-564929), 5, 10, 15 or 20 mg orally as a tablet or other appropriate delivery system once a day. In exemplary embodiments, the androgenic agent provided once a day may vary between 0.5 mg to 20 mg, between 3 mg to 9 mg, between 6 mg to 15 mg or between 6 mg to 12 mg. The duration of treatment for administration of the androgenic agent and the aromatase inhibitor, or a pharmaceutical composition or a combination of the same, may vary between about 2 weeks to about 4 weeks, between about 6 months to about 2 years, between about 3 months to about 5 years, between about 1 year and about 5 years and between about 1 year to about 2 years. In certain embodiments, the duration of treatment may be about 2 weeks, about 3 months, about 6 months, about 9 months, about 1 year, about 1.5 years, about 2 years, about 2.5 years or about 3 years. In certain embodiments, the duration of treatment may be at least 2 weeks, 3 months, 6 months, 9 months, 1 year, 1.5 years, 2 years, 3 year or 4 years. The treatment may be applied to one or more of the following, a reduction in ABD %, a reduction in AABD, a reduction in VBD %; a reduction in AVBD; a reduction in breast pain; a reduction in breast stiffness; a reduction in breast elasticity; a reduction in macromastia; a reduction in breast cysts; an improvement in mammographic diagnostic sensitivity and a reduction in false positives; an increase in the ratio between fibro-glandular and adipose tissue; a stabilization and/or an increase in levels of androgen receptor expression; and an increase in GCDFP15.

In exemplary embodiments, a patient is provided an aromatase inhibitor of exemestane 25 mg 6-Methylideneandrosta-1,4-diene-3,17-dione orally as a tablet or other appropriate delivery system once a day in combination with at least one of the following amounts of a Hydantoin androgenic agent such as (4-[(7R,7aS)-7-hydroxy-1,3-dioxo-5,6,7,7a-tetrahydropyrrolo[1,2-c]imidazol-2-yl]-2-chloro-3-methylbenzonitrile (also known BMS-564929), 5, 10, 15 or 20 mg orally as a tablet or other appropriate delivery system once a day. In exemplary embodiments, the androgenic agent provided once a day may vary between 0.5 mg to 20 mg, between 3 mg to 9 mg, between 6 mg to 15 mg or between 6 mg to 12 mg. The duration of treatment for administration of the androgenic agent and the aromatase inhibitor, or a pharmaceutical composition or a combination of the same, may vary between about 2 weeks to about 4 weeks, between about 6 months to about 2 years, between about 3 months to about 5 years, between about 1 year and about 5 years and between about 1 year to about 2 years. In certain embodiments, the duration of treatment may be about 2 weeks, about 3 months, about 6 months, about 9 months, about 1 year, about 1.5 years, about 2 years, about 2.5 years or about 3 years. In certain embodiments, the duration of treatment may be at least 2 weeks, 3 months, 6 months, 9 months, 1 year, 1.5 years, 2 years, 3 year or 4 years. The treatment may be applied to one or more of the following: a reduction in ABD %, a reduction in AABD, a reduction in VBD %; a reduction in AVBD; a reduction in breast pain; a reduction in breast stiffness; a reduction in breast elasticity; a reduction in macromastia; a reduction in breast cysts; an improvement in mammographic diagnostic sensitivity and a reduction in false positives; an increase in the ratio between fibro-glandular and adipose tissue; a stabilization and/or an increase in levels of androgen receptor expression; and an increase in GCDFP15.

In exemplary embodiments, a patient is provided an aromatase inhibitor of 1 mg anastrozole (2,2'-[5-(1H-1,2,4-triazol-1-ylmethyl)-1,3-phenylene]bis(2-methylpropanenitrile)) orally as a tablet or other appropriate delivery system once a day in combination with at least one of the following amounts of a Tetrahydroquinolone androgenic agent such as (3aS,4S,9bS)—N-[2-(8-Cyano-1-formyl-2,3,3a,4,5,9b-hexahydro-1H-pyrrolo[3,2-c]quinolin-4-yl)-2-methylpropyl]-4,6-difluorobenzofuran-2-carboxyamide (also known as S-101479)), 5, 10, 15 or 20 mg orally as a tablet or other appropriate delivery system once a day. In exemplary embodiments, the androgenic agent provided once a day may vary between 0.05 mg to 2 mg, between 0.3 mg to 0.9 mg, between 0.2 mg to 0.75 mg or between 0.3 mg to 1 mg. The duration of treatment for administration of the androgenic agent and the aromatase inhibitor, or a pharmaceutical composition or a combination of the same, may vary between about 2 weeks to about 4 weeks, between about 6 months to about 2 years, between about 3 months to about 5 years, between about 1 year and about 5 years and between about 1 year to about 2 years. In certain embodiments, the duration of treatment may be about 2 weeks, about 3 months, about 6 months, about 9 months, about 1 year, about 1.5 years, about 2 years, about 2.5 years or about 3 years. In certain embodiments, the duration of treatment may be at least 2 weeks, 3 months, 6 months, 9 months, 1 year, 1.5 years, 2 years, 3 year or 4 years. The treatment may be applied to one or more of the following a reduction in ABD %, a reduction in AABD, a reduction in VBD %; a reduction in AVBD; a reduction in breast pain; a reduction in breast stiffness; a reduction in breast elasticity; a reduction in macromastia; a reduction in breast cysts; an improvement in mammographic diagnostic sensitivity and a reduction in false positives; an increase in the ratio between fibroglandular and adipose tissue; a stabilization and/or an increase in levels of androgen receptor expression; and an increase in GCDFP15.

In exemplary embodiments, a patient is provided an an aromatase inhibitor of 2.5 mg letrozole (4,4'-((1H-1,2,4-triazol-1 yl)methylene)dibenzonitrile) orally as a tablet or other appropriate delivery system once a day in combination with at least one of the following amounts of a Tetrahydroquinolone androgenic agent such as (3aS,4S,9bS)—N-[2-(8-Cyano-1-formyl-2,3,3a,4,5,9b-hexahydro-1H-pyrrolo[3,2-c]quinolin-4-yl)-2-methylpropyl]-4,6-difluorobenzofuran-2-carboxyamide (also known as S-101479)), 5, 10, 15 or 20 mg orally as a tablet or other appropriate delivery system once a day. In exemplary embodiments, the androgenic agent provided once a day may vary between 0.5 mg to 20 mg, between 3 mg to 9 mg, between 6 mg to 15 mg or between 6 mg to 12 mg. The duration of treatment for administration of the androgenic agent and the aromatase inhibitor, or a pharmaceutical composition or a combination of the same, may vary between about 2 weeks to about 4 weeks, between about 6 months to about 2 years, between about 3 months to about 5 years, between about 1 year and about 5 years and between about 1 year to about 2 years. In certain embodiments, the duration of treatment may be about 2 weeks, about 3 months, about 6 months, about 9 months, about 1 year, about 1.5 years, about 2 years, about 2.5 years or about 3 years. In certain embodiments, the duration of treatment may be at least 2 weeks, 3 months, 6 months, 9 months, 1 year, 1.5 years, 2 years, 3 year or 4 years. The treatment may be applied to one or more of the following a reduction in ABD %, a reduction in AABD, a reduction in VBD %; a reduction in AVBD; a reduction in breast pain; a reduction in breast stiffness; a reduction in breast elasticity; a reduction in macromastia; a reduction in breast cysts; an improvement in mammographic diagnostic sensitivity and a reduction in false positives; an increase in the ratio between fibroglandular and adipose tissue; a stabilization and/or an increase in levels of androgen receptor expression; and an increase in GCDFP15.

In exemplary embodiments, a patient is provided an aromatase inhibitor of exemestane 25 mg 6-Methylideneandrosta-1,4-diene-3,17-dione orally as a tablet or other appropriate delivery system once a day in combination with at least one of the following amounts of a Tetrahydroquinolone androgenic agent such as (3aS,4S,9bS)—N-[2-(8-Cyano-1-formyl-2,3,3a,4,5,9b-hexahydro-1H-pyrrolo[3,2-c]quinolin-4-yl)-2-methylpropyl]-4,6-difluorobenzofuran-2-carboxyamide (also known as S-101479)), 5, 10, 15 or 20 mg orally as a tablet or other appropriate delivery system once a day. In exemplary embodiments, the androgenic agent provided once a day may vary between 0.5 mg to 20 mg, between 3 mg to 9 mg, between 6 mg to 15 mg or between 6 mg to 12 mg. The duration of treatment for administration of the androgenic agent and the aromatase inhibitor, or a pharmaceutical composition or a combination of the same, may vary between about 2 weeks to about 4 weeks, between about 6 months to about 2 years, between about 3 months to about 5 years, between about 1 year and about 5 years and between about 1 year to about 2 years. In certain embodiments, the duration of treatment may be about 2 weeks, about 3 months, about 6 months, about 9 months, about 1 year, about 1.5 years, about 2 years, about 2.5 years or about 3 years. In certain embodiments, the duration of treatment may be at least 2 weeks, 3 months, 6 months, 9 months, 1 year, 1.5 years, 2 years, 3 year or 4 years. The treatment may be applied to one or more of the following: a reduction in ABD %, a reduction in AABD, a reduction in VBD %; a reduction in AVBD; a reduction in breast pain; a reduction in breast stiffness; a reduction in breast elasticity; a reduction in macromastia; a reduction in breast cysts; an improvement in mammographic diagnostic sensitivity and a reduction in false positives; an increase in the ratio between fibroglandular and adipose tissue; a stabilization and/or an increase in levels of androgen receptor expression and an increase in GCDFP15.

In exemplary embodiments, a patient is provided an aromatase inhibitor of 1 mg anastrozole (2,2'-[5-(1H-1,2,4-triazol-1-ylmethyl)-1,3-phenylene]bis(2-methylpropanenitrile)) orally as a tablet or other appropriate delivery system once a day in combination with at least one of the following amounts of an aniline androgenic agent such as 2-Chloro-4-({1-[5-(4-cyanophenyl)-1,3,4-oxadiazol-2-yl]-2-hydroxypropyl}amino)-3-methylbenzonitrile (also known as RAD140) 20, 40, 60 or 80 mg orally as a tablet or other appropriate delivery system once a day. In exemplary embodiments, the androgenic agent provided once a day may vary between 10 mg to 100 mg, between 20 mg to 80 mg, between 20 mg to 60 mg or between 40 mg to 80 mg. The duration of treatment for administration of the androgenic agent and the aromatase inhibitor, or a pharmaceutical composition or a combination of the same, may vary between about 2 weeks to about 4 weeks, between about 6 months to about 2 years, between about 3 months to about 5 years, between about 1 year and about 5 years and between about 1 year to about 2 years. In certain embodiments, the duration of treatment may be about 2 weeks, about 3 months, about 6 months, about 9 months, about 1 year, about 1.5 years, about 2 years, about 2.5 years or about 3 years. In certain embodiments, the duration of treatment may be at least 2 weeks, 3 months, 6 months, 9 months, 1 year, 1.5 years, 2 years, 3 year or 4 years. The treatment may be applied to one or more of the following: a reduction in ABD %, a reduction in AABD, a reduction in VBD %; a reduction in AVBD; a reduction in breast pain; a reduction in breast stiffness; a reduction in breast elasticity; a reduction in macromastia; a reduction in breast cysts; an improvement in mammographic diagnostic sensitivity and a reduction in false positives; an increase in the ratio between fibroglandular and adipose tissue; a stabilization and/or an increase in levels of androgen receptor expression; and an increase in GCDFP15.

In exemplary embodiments, a patient is provided an aromatase inhibitor of 2.5 mg letrozole (4,4'-((1H-1,2,4-triazol-1 yl)methylene)dibenzonitrile) orally as a tablet or other appropriate delivery system once a day in combination with at least one of the following amounts of an aniline androgenic agent such as 2-Chloro-4-({1-[5-(4-cyanophenyl)-1,3,4-oxadiazol-2-yl]-2-hydroxypropyl}amino)-3-methylbenzonitrile (also known as RAD140) 20, 40, 60 or 80 mg orally as a tablet or other appropriate delivery system once a day. In exemplary embodiments, the androgenic agent provided once a day may vary between 10 mg to 100 mg, between 20 mg to 80 mg, between 20 mg to 60 mg or between 40 mg to 80 mg. The duration of treatment for administration of the androgenic agent and the aromatase inhibitor, or a pharmaceutical composition or a combination of the same, may vary between about 2 weeks to about 4 weeks, between about 6 months to about 2 years, between about 3 months to about 5 years, between about 1 year and about 5 years and between about 1 year to about 2 years. In certain embodiments, the duration of treatment may be about 2 weeks, about 3 months, about 6 months, about 9 months, about 1 year, about 1.5 years, about 2 years, about 2.5 years or about 3 years. In certain embodiments, the duration of treatment may be at least 2 weeks, 3 months, 6 months, 9 months, 1 year, 1.5 years, 2 years, 3 year or 4 years. The treatment may be applied to one or more of the following: a reduction in ABD %, a reduction in AABD, a reduction in VBD %; a reduction in AVBD; a reduction in breast pain; a reduction in breast stiffness; a reduction in breast elasticity; a reduction in macromastia; a reduction in breast cysts; an improvement in mammographic diagnostic sensitivity and a reduction in false positives; an increase in the ratio between fibro-glandular and adipose tissue; a stabilization and/or an increase in levels of androgen receptor expression; and an increase in GCDFP15.

In exemplary embodiments, a patient is provided an aromatase inhibitor of exemestane 25 mg 6-Methylideneandrosta-1,4-diene-3,17-dione orally as a tablet or other appropriate delivery system once a day in combination with at least one of the following amounts of an aniline androgenic agent such as 2-Chloro-4-({1-[5-(4-cyanophenyl)-1,3,4-oxadiazol-2-yl]-2-hydroxypropyl}amino)-3-methylbenzonitrile (also known as RAD140) 20, 40, 60 or 80 mg orally as a tablet or other appropriate delivery system once a day. In exemplary embodiments, the androgenic agent provided once a day may vary between 10 mg to 100 mg, between 20 mg to 80 mg, between 20 mg to 60 mg or between 40 mg to 80 mg. The duration of treatment for administration of the androgenic agent and the aromatase inhibitor, or a pharmaceutical composition or a combination of the same, may vary between about 2 weeks to about 4 weeks, between about 6 months to about 2 years, between about 3 months to about 5 years, between about 1 year and about 5 years and between about 1 year to about 2 years. In certain embodiments, the duration of treatment may be about 2 weeks, about 3 months, about 6 months, about 9 months, about 1 year, about 1.5 years, about 2 years, about 2.5 years or about 3 years. In certain embodiments, the duration of treatment may be at least 2 weeks, 3 months, 6 months, 9 months, 1 year, 1.5 years, 2 years, 3 year or 4 years. The treatment may be applied to one or more of the following: a reduction in ABD %, a reduction in AABD, a reduction in VBD %; a reduction in AVBD; a reduction in breast pain; a reduction in breast stiffness; a reduction in breast elasticity; a reduction in macromastia; a reduction in breast cysts; an improvement in mammographic diagnostic sensitivity and a reduction in false positives; an increase in the ratio between fibro-glandular and adipose tissue; a stabilization and/or an increase in levels of androgen receptor expression; and an increase in GCDFP15.

The androgenic agent may, for example, be selected from the group consisting of: testosterone, methyl testosterone, testosterone undecanoate, testosterone propionate dihydrotestosterone, 5α-dihydrotestosterone, or alternatively androstenediol androstenediol-3-acetate, androstenediol-17-acetate, androstenediol-3,17-diacetate, androstenediol-17-benzoate, androstenediol-3-acetate-17-benzoate, androstenedione, adrenosterone, androsterone acetate, androsterone propionate, androsterone benzoate, dehydroepiandrosterone, sodium dehydroepiandrosterone sulfate, oxymetholone, fluoxymesterone, methandrostenolone, testolactone, pregnenolone, 17α-methylnortestosterone, norethandrolone, dromostanolone, dromostanolone propionate, nandrolone, nandrolone phenpropionate, nandrolone decanoate, nandrolone furylpropionate, nandrolone cyclohexanepropionate, nandrolone benzoate, nandrolone cyclohexanecarboxylate, danazol, oxymetholone, androsterone, stanozolol, ethylestrenol, oxandrolone, bolasterone, mesterolone, testosterone cypionate, testosterone phenylacetate, testosterone enanthate, testosterone acetate, testosterone buciclate, testosterone heptanoate, testosterone decanoate, testosterone caprate, testosterone isocaprate, and isomers, metabolites, derivatives, precursors of the aforementioned compounds, or combinations thereof. In addition to the pharmaceutically acceptable esters of testosterone, esters of dihydrotestosterone, include, but are not limited to, the enanthate, propionate, cypionate, phenylacetate, acetate, isobutyrate, buciclate, heptanoate, decanoate, undecanoate, caprate and/or isocaprate esters.

The androgenic agent may, for example, be a selective androgen receptor modulator ("SARM") and may comprise (2S)-3-(4-cyanophenoxy)-N-[4-cyano-3-(trifluoromethyl) phenyl]-2-hydroxy-2-methylpropanamide (also known as Enobosarm, Ostarine, GTx-024, and MK-2866), (7R,7aS)-2-Chloro-4-(7-hydroxy-1,3-dioxotetrahydropyrrolo[1,2-c] imidazol-2-yl)-3-methylbenzonitrile (also known as BMS-564,929), 4-((R)-2-((R)-2,2,2-trifluoro-1-hydroxyethyl) pyrrolidin-1-yl)-2-trifluoromethyl)benzonitrile (also known as LGD-4033, or Ligandrol), 4-(3-Hydroxy-8-aza-bicyclo [3.2.1]octyl)-naphthalene-1-carbonitrile (also known as AC-262,356), JNJ-28330835, 6-(bis-(2,2,2-trifluoroethyl) amino)-4-trifluoromethyl-1H-quinolin-2-one (also known as LGD-2226), 9-chloro-2-ethyl-1-methyl-3-(2,2,2-trifluoroethyl)-3H-pyrrolo[3,2-f]quinolin-7(6H)-one (also known as LGD-3303), 2-[4-(dimethylamino)-6-nitro-1,2,3,4-tetrahydroquinolin-2-yl]-2-methylpropan-1-ol (also known as S-40503), or (2S)—N-(4-cyano-3-trifluoromethylphenyl)-3-(3-fluoro-4-chlorophenoxy)-2-hydroxy-2-methyl-propanamide (also known as S-23), or derivatives thereof. The aromatase inhibitor and androgenic agent combination may, for example, be one or more of the following: anastrozole (2,2'-[5-(1H-1,2,4-triazol-1-ylmethyl)-1,3-phenylene]bis(2-methylpropanenitrile)) orally as a tablet once a day in combination with (2S)-3-(4-cyanophenoxy)-N-[4-cyano-3-(trifluoromethyl)phenyl]-2-hydroxy-2-methylpropanamide (also known as Enobosarm, Ostarine, GTx-024, and MK-2866); letrozole (4,4'-((1H-1,2,4-triazol-1 yl)methylene)dibenzonitrile) orally as a tablet once a day in combination with (4-((R)-2-((R)-2,2,2-trifluoro-1-hydroxyethyl) pyrrolidin-1-yl)-2-trifluoromethyl)benzonitrile (also known as LGD-4033, or Ligandrol); exemestane, 6-Methylideneandrosta-1,4-diene-3,17-dione orally as a tablet once a day in combination with (4-[(7R,7aS)-7-hydroxy-1,3-dioxo-5,6,7,7a-tetrahydropyrrolo[1,2-c]imidazol-2-yl]-2-chloro-3-methylbenzonitrile (also known BMS-564929); anastrozole (2,2'-[5-(1H-1,2,4-triazol-1-ylmethyl)-1,3-phenylene]bis(2-methylpropanenitrile)) orally as a tablet once a day in combination with at least one of the following amounts of a Tetrahydroquinolone androgenic agent such as (3aS,4S,9bS)—N-[2-(8-Cyano-1-formyl-2,3,3a,4,5,9b-hexahydro-1H-pyrrolo[3,2-c]quinolin-4-yl)-2-methylpropyl]-4,6-difluorobenzofuran-2-carboxyamide (also known as S-101479).

The androgenic agent may be selected from the group consisting of testosterone, methyltestosterone, testosterone undecanoate, testosterone propionate, a selective androgen receptor modulator or combinations thereof.

The androgenic agents may be selected from the group consisting of naturally occurring androgens, synthetic androgens, selective androgen receptor modulators, metabolites, precursors, derivatives thereof or combinations thereof. The agents may be incorporated into the present dosage units and thus administered in the form of a pharmaceutically acceptable derivative, metabolite, precursor, analog, ester, salt, or amide, or the agents may be modified by appending one or more appropriate functionalities to enhance selected biological properties such as penetration through mucosal tissue. In general, with regard to androgenic agents, the use of esters is desirable.

Preparation of esters, as noted herein, involves functionalization of hydroxyl and/or carboxyl groups that may be present, as will be appreciated by those skilled in the arts of pharmaceutical chemistry and drug delivery. For example, to prepare testosterone esters, the 17-hydroxyl group of the testosterone molecule is generally caused to react with a suitable organic acid under esterifying conditions, such conditions typically involving the use of a strong acid such as sulfuric acid, hydrochloric acid, or the like, and a temperature sufficient to allow the reaction to proceed at reflux. Esters can be reconverted to the free acids, if desired, by using conventional hydrogenolysis or hydrolysis procedures.

The androgenic agent may be, for example, testosterone, methyltestosterone, testosterone undecanoate, testosterone propionate, dehydroepiandrosterone, or sodium dehydroepiandrosterone sulfate, or a metabolic precursor, metabolite, or derivative thereof. In certain embodiments, the androgenic agent may be provided in the form of testosterone undecanoate, an orally active testosterone preparation that is a fatty acid ester of the natural androgen testosterone. Unlike other oral testosterone preparations, testosterone undecanoate is able to by-pass the liver via the lymphatic system and is therefore orally bioavailable. In certain embodiments, the androgenic agent may be a SARM.

Additionally, testosterone is difficult to deliver orally, as 80-90% is broken down in the liver as it is absorbed from the gut. As such, alternative delivery mechanisms have been explored, e.g. the testosterone patch (Intrinsa®) by Proctor & Gamble used to improve sexual libido in post-menopausal women.

An effective amount of an androgenic agent may vary among androgenic agents. In addition, the effective amount per day of testosterone may also vary. In certain aspects, an effective amount of testosterone may be delivered by a buccal system, in the form of a 1 wt % gel, in the form of a subcutaneous implant, in the form of an injection, in the form of a transdermal system, or by intramuscular administration. In certain embodiments, an effective amount of testosterone may be between 2 to 300 mg, such as, between 2 to 250 mg, between 2 to 200 mg, between 2 to 150 mg, between 2 to 100 mg, between 2 to 90 mg, between 200 to 300 mg, between 150 to 250 mg, between 100 to 200 mg, between 50 to 150 mg, between 40 to 120 mg, between 50 to 100 mg, between 100 to 300 mg, between 40 to 100 mg, between 30 to 80 mg, between 5 to 75 mg, between 10 to 70 mg, between 20 to 60 mg, between 30 to 50 mg or between 35 to 45 mg. For example, in certain embodiments, the effective amount of testosterone may be between 40 to 120 mg, for example, about 20 mg, about 40 mg, about 60 mg about 80 mg, about 100 mg or about 120 mg.

In certain embodiments, an effective amount of testosterone may be delivered by a buccal system, and may be between 2 to 100 mg, such as between 5 to 90 mg, between 5 to 80 mg, between 10 to 70 mg, between 20 to 60 mg, between 30 to 50 mg, between 2 to 50 mg, between 40 to 100 mg, between 60 to 100 mg, between 25 to 75 mg or between 35 to 45 mg.

In certain embodiments, an effective amount of testosterone may be delivered in the form of a 1 wt. % gel containing be between 2 to 100 mg testosterone, such as between 5 to 90 mg, between 5 to 80 mg, between 10 to 70 mg, between 20 to 60 mg, between 30 to 50 mg, between 2 to 50 mg, between 40 to 100 mg, between 60 to 100 mg, between 25 to 75 mg or between 35 to 45 mg testosterone.

In certain embodiments, an effective amount of testosterone may be delivered in the form of a subcutaneous implant, such as a subcutaneous pellet, containing between 2 to 200 mg testosterone, such as between 2 to 150 mg, between 2 to 100 mg, between 100 to 200 mg, between 50 to 150 mg, between 50 to 100 mg, between 40 to 100 mg, between 30 to 80 mg, between 2 to 90 mg, between 5 to 90 mg, between 5 to 80 mg, between 10 to 70 mg, between 20 to 60 mg, between 30 to 50 mg, between 2 to 50 mg, between 40 to 100 mg, between 60 to 100 mg, between 25 to 75 mg or between 35 to 45 mg testosterone.

In certain embodiments, an effective amount of testosterone may be delivered in the form of an injection, such as an injection of an aqueous suspension containing a concentration of testosterone of between 10 mg/mL to 150 mg/mL, such as between 20 mg/mL to 130 mg/mL, between 50 mg/mL to 125 mg/mL, between 75 mg/mL to 110 mg/mL, between 90 mg/mL to 150 mg/mL, between 100 mg/mL to 150 mg/mL, between 50 mg/mL to 100 mg/mL or between 10 mg/mL to 50 mg/mL.

In certain embodiments, an effective amount of testosterone may be delivered in the form of a transdermal system providing testosterone at a rate of between 0.1-10 mg/24 hours, such as at a rate of between 0.1-8 mg/24 hours, between 0.1-6 mg/24 hours, between 0.1-5 mg/24 hours, between 0.15-10 mg/24 hours, between 0.3-10 mg/24 hours, between 0.5-10 mg/24 hours, between 0.6-10 mg/24 hours, between 0.8-10 mg/24 hours, between 1-10 mg/24 hours, between 0.5-7.5 mg/24 hours, between 0.4-7 mg/24 hours, between 2-8 mg/24 hours, between 1.5-6 mg/24 hours, between 0.25-4 mg/24 hours, between 3-7 mg/24 hours, between 4-10 mg/24 hours, between 5-10 mg/24 hours or between 1-5 mg/24 hours.

In certain embodiments, an effective amount of testosterone may be by intramuscular administration, for example between about 5 to about 25 mg of testosterone at a rate of once every 2-3 weeks, or once every 24 weeks.

An effective amount per day of methyltestosterone may vary. In exemplary embodiments, the effective amount of methyltestosterone may be between 0.1 mg to 10 mg, such as between 0.5 mg to 9 mg, between 2 mg to 8 mg, between 3 mg to 7 mg, or between 4 mg to 5 mg. For example, the effective amount of methyltestosterone may be about 0.5 mg, about 1.25 mg or about 2.5 mg.

An effective amount per day of testosterone undecanoate may vary. In exemplary embodiments, the effective amount of testosterone undecanoate may be between 10 to 120 mg, such as between 20 to 110 mg, between 30 to 100 mg, between 40 to 90 mg, between 50 to 80 mg or between 60 to 70 mg. For example, the effective amount of testosterone undecanoate may be about 20 mg, about 40 mg or about 80 mg.

An effective amount per day of testosterone propionate may vary. In certain embodiments, the effective amount of testosterone propionate may be between 10 to 120 mg, such as between 20 to 110 mg, between 30 to 100 mg, between 40 to 90 mg, between 50 to 80 mg or between 60 to 70 mg. For example, the effective amount of testosterone propionate may be about 20 mg, about 40 mg or about 80 mg.

An effective amount per day of testosterone cypionate may vary. In certain embodiments, an effective amount of testosterone cypionate may be delivered by a buccal system, in the form of a 1 wt. % gel, a subcutaneous implant, an injection, a transdermal system, by intramuscular administration or combinations thereof. In certain embodiments, the effective amount of testosterone cypionate may be between 2 to 450 mg, such as between 2 to 400 mg, between 2 to 350 mg, between 2 to 300 mg, between 2 to 250 mg, between 2 to 200 mg, between 2 to 150 mg, between 2 to 100 mg, between 2 to 90 mg, between 200 to 450 mg, between 200 to 400 mg, between 350 to 450 mg, between 300 to 400 mg, between 200 to 300 mg, between 150 to 250 mg, between 100 to 200 mg, between 50 to 150 mg, between 50 to 100 mg, between 100 to 300 mg, between 40 to 100 mg, between 30 to 80 mg, between 5 to 75 mg, between 10 to 70 mg, between 20 to 60 mg, between 30 to 50 mg or between 35 to 45 mg.

For example, an effective amount of testosterone cypionate may be delivered in the form of an injection, such as an injection of an aqueous suspension containing a concentration of testosterone cypionate of between 2 mg/mL to 200 mg/mL, such as between 2 mg/mL to 150 mg/mL, between 2 mg/mL to 100 mg/mL, between 5 mg/mL to 200 mg/mL, between 5 mg/mL to 150 mg/mL, between 10 mg/mL to 150 mg/mL, between 20 mg/mL to 130 mg/mL, between 50 mg/mL to 125 mg/mL, between 75 mg/mL to 110 mg/mL, between 90 mg/mL to 150 mg/mL, between 100 mg/mL to 150 mg/mL, between 50 mg/mL to 100 mg/mL, between 100 mg/mL to 200 mg/mL, between 150 mg/mL to 200 mg/mL, between 75 mg/mL to 150 mg/mL, between 125 mg/mL to 175 mg/mL or between 10 mg/mL to 50 mg/mL.

In certain embodiments, an effective amount of testosterone cypionate may be by intramuscular administration, for example between 5 to 25 mg of testosterone cypionate at a rate of once every 2-3 weeks, or once every 24 weeks.

An effective amount per day of testosterone enanthate may vary. In certain embodiments, an effective amount of testosterone enanthate may be delivered by a buccal system, in the form of a 1 wt. % gel, a subcutaneous implant, an injection, a transdermal system, by intramuscular administration or combinations thereof. In certain embodiments, the effective amount of testosterone enanthate may be between 2 to 500 mg, such as between 2 to 400 mg, between 200 to 500 mg, between 200 to 400 mg, between 200 to 350 mg, between 300 to 500 mg, between 350 to 450 mg, between 400 to 500 mg, between 2 to 275 mg, between 2 to 225 mg, between 2 to 175 mg, between 2 to 125 mg, between 2 to 90 mg, between 200 to 300 mg, between 150 to 250 mg, between 100 to 200 mg, between 50 to 450 mg, between 50 to 350 mg, between 50 to 200 mg, between 50 to 100 mg, between 100 to 300 mg, between 40 to 100 mg, between 30 to 80 mg, between 5 to 75 mg, between 10 to 70 mg, between 20 to 60 mg, between 30 to 50 mg, or between 35 to 45 mg.

In certain embodiments, an effective amount of testosterone enanthate may be delivered by a buccal system, and may be between 2 to 100 mg for 1-3 times per day, such as between 5 to 80 mg, between 10 to 70 mg, between 20 to 60 mg, between 30 to 50 mg, between 60 to 100 mg, between 25 to 75 mg, between 25 to 35 mg, between 20 to 30 mg, or between 35 to 45 mg for 1-3 times per day.

In certain embodiments, an effective amount of testosterone enanthate may be delivered in the form of a subcutaneous implant, such as a subcutaneous pellet, containing between 2 to 500 mg testosterone enanthate, such as between 2 to 400 mg, between 200 to 500 mg, between 200 to 400 mg, between about 200 to about 350 mg, between 300 to 500 mg, between 2 to 250 mg, between 2 to 200 mg, between 2 to 150 mg, between 2 to 100 mg, between 200 to 300 mg, between 150 to 250 mg, between 50 to 400 mg, between 50 to 300 mg, between 50 to 150 mg, between 50 to 100 mg, between 40 to 100 mg, between 30 to 80 mg, between 10 to 70 mg, between 30 to 50 mg or between 35 to 45 mg testosterone enanthate.

In certain embodiments, an effective amount of testosterone enanthate may be delivered in the form of an injection, such as an injection of an oil formulation containing a concentration of testosterone enanthate of between 2 mg/mL to 250 mg/mL, such as between 2 mg/mL to 200 mg/mL, between 150 mg/mL to 200 mg/mL, between 150 mg/mL to 250 mg/mL, between 10 mg/mL to 150 mg/mL, between 50 mg/mL to 125 mg/mL, between 75 mg/mL to 110 mg/mL, between 90 mg/mL to 150 mg/mL, between 50 mg/mL to 100 mg/mL or between 10 mg/mL to 50 mg/mL.

In certain aspects, an effective amount of testosterone enanthate may be delivered in the form of a transdermal system providing testosterone enanthate at a rate of between 0.1-10 mg/24 hours, such as at a rate of between 0.1-8 mg/24 hours, between 0.1-6 mg/24 hours, between 0.1-5 mg/24 hours, between 0.2-10 mg/24 hours, between 0.4-10 mg/24 hours, between 0.5-10 mg/24 hours, between 0.7-10 mg/24 hours, between 0.8-10 mg/24 hours, between 1-10 mg/24 hours, between 0.5-7.5 mg/24 hours, between 1.5-6 mg/24 hours, between 0.25-6 mg/24 hours, between 3-7 mg/24 hours, between 4-10 mg/24 hours, between 5-10 mg/24 hours or at a rate of between 1-5 mg/24 hours.

In certain embodiments, an effective amount of testosterone enanthate may be by intramuscular administration, for example, between 50 to 400 mg of testosterone enanthate at a rate of once every 2-3 weeks, or once every 24 weeks, for example, between 60 to 200 mg of testosterone enanthate at a rate of once every 2-3 weeks, or once every 2-4 weeks.

An effective amount per day of a SARM may vary. In certain embodiments, an effective amount of the selective androgen receptor modulator may be between 10 to 120 mg, between 30 to 100 mg, between 50 to 80 mg or between 60 to 70 mg. For example, in certain aspects, the effective amount of the selective androgen receptor modulator may be about 20 mg, about 40 mg, or about 80 mg.

In exemplary embodiments, an effective amount per day of an Quinolinone androgenic agent such as (4-((R)-2-((R)-2,2,2-trifluoro-1-hydroxyethyl)pyrrolidin-1-yl)-2-trifluoromethyl)benzonitrile (also known as LGD-4033, or Ligandrol) may vary. An effective amount may be between 0.1 to 3 mg, such as between 0.5 to 2.5 mg, or between 1 to 1.5 mg.

For example, the effective amount may be about 0.1 mg, about 0.5 mg, about 1 mg or about 2 mg.

In exemplary embodiments, an effective amount per day of a Tetrahydroquinolone androgenic agent such as (3aS,4S,9bS)—N-[2-(8-Cyano-1-formyl-2,3,3a,4,5,9b-hexahydro-1H-pyrrolo[3,2-c]quinolin-4-yl)-2-methylpropyl]4,6-difluorobenzofuran-2-carboxyamide (also known as S-101479)) may vary. An effective amount may be between 1 to 30 mg, such as between 5 to 25 mg, or between 10 to 15 mg. For example, the effective amount may be about 2 mg, about 5 mg, about 10 mg, about 15 mg or about 20 mg.

In exemplary embodiments, an effective amount per day of a Hydantoin androgenic agent such as (4-[(7R,7aS)-7-hydroxy-1,3-dioxo-5,6,7,7a-tetrahydropyrrolo[1,2-c]imidazol-2-yl]-2-chloro-3-methylbenzonitrile (also known BMS-564929), may vary. An effective amount may be between 1 to 30 mg, such as between 5 to 25 mg, or between 10 to 15 mg. For example, the effective amount may be about 2 mg, about 5 mg, about 10 mg, about 15 mg or about 20 mg.

The effective amount of androgenic agent used in conjunction with an aromatase inhibitor may be relatively lower than a standard dose because of low levels of sex hormone binding globulin in the patient's serum which may be caused by the aromatase inhibitor.

Sex hormone binding globulin binds an androgenic agent (e.g., testosterone) and transports it around the body. Its production is regulated by several mechanisms, but one of the effectors of its level is the amount of estrogen in the serum: the higher the estrogen, the higher the sex hormone binding globulin and the lower the free androgenic agent. Conversely, the lower the estrogen, the lower the sex hormone binding globulin, and the higher the free androgenic agent, which means the androgenic agent has higher bioavailability. Thus after menopause, as the estrogen level falls, the sex hormone binding globulin level falls and the free androgenic agent such as testosterone rises. This free androgenic agent has multiple functions, as the androgen receptor is expressed in all cells of the body.

In certain embodiments, the dosage levels below the lower limit of the aforesaid range of the androgenic agent may be more than adequate, while in other cases still larger doses above the upper limit of the aforesaid range may be employed without causing any harmful side effects.

In certain embodiments, the aromatase inhibitor may be, for example, a steroidal aromatase inhibitor, a nonsteroidal aromatase inhibitor, and/or isomers thereof. Steroidal aromatase inhibitors developed to date build upon the basic androstenedione nucleus and incorporate chemical substituents at varying positions on the steroid. Examples of steroidal aromatase inhibitors include, but are not limited to, exemestane (Aromasin®) and formestane. Additional examples include mechanism-based steroidal aromatase inhibitors that mimic the substrate, are converted by the enzyme to a reactive intermediate, and result in the inactivation of aromatase. In certain embodiments, the aromatase inhibitor is exemestane. Nonsteroidal aromatase inhibitors may be divided into three classes: aminoglutethimide-like molecules, imidazole/triazole derivatives, and flavonoid analogs. Examples of non-steroidal aromatase inhibitors include, but are not limited to, anastrozole (Arimidex®), letrozole (Femara®), vorozole and fadrozole. In certain embodiments, the aromatase inhibitor is either anastrozole or letrozole. In certain embodiments, the aromatase inhibitor is anastrozole.

Aromatase inhibitors often include third-generation aromatase inhibitors, such as anastrozole (Arimidex®), exemestane (Aromasin®), and letrozole (Femara®). These third generation aromatase inhibitors have brought a change in the therapeutic approach to patients with hormone-sensitive breast cancer. Such aromatase inhibitors are specific in their action in that they virtually ablate estrogen in the serum and thus lower sex hormone binding globulin, which enables the achievement of a synergistic effect.

In certain embodiments, the aromatase inhibitor may be selected from the group consisting of anastrozole, exemestane, or letrozole. In certain embodiments, the aromatase inhibitor is either anastrozole or letrozole. In certain embodiments, the aromatase inhibitor is anastrozole.

The effective amount of an aromatase inhibitor may vary among aromatase inhibitors. In certain embodiments, an effective amount of an aromatase inhibitor may be delivered orally, in the form of a subcutaneous implant or a transdermal system or combinations thereof. The effective amount per day for anastrozole (Aromasin®) may vary. For example, the effective amount of Aromasin® may be between 0.1 to 150 mg, such as between 0.1 to 50 mg, between 0.1 to 10 mg, between 0.1 to 8 mg, between 0.1 to 6 mg, between 0.1 to 5 mg, between 0.1 to 4 mg, between 0.1 to 2 mg, between 0.1 to 1 mg, between 0.5 to 5 mg, between 1 to 10 mg, between 5 to 100 mg, between 10 to 80 mg, between 25 to 150 mg, between 30 to 60 mg, between 80 to 150 mg, or between 40 to 50 mg. For example, in certain aspects, the effective amount of Aromasin® may be about 25 mg, about 10 mg, about 5 mg, about 3 mg, about 2 mg, about 1 mg or about 0.5 mg.

The effective amount per day of Arimidex®, may vary. For example, the effective amount for exemestane (Arimidex®) may be between 0.1 mg to 200 mg, such as between 5 mg to 200 mg, between 20 mg to 200 mg, between 50 mg to 200 mg, between 80 mg to 200 mg, between 100 mg to 200 mg, between 150 mg to 200 mg, between 1 mg to 100 mg, between 50 mg to 100 mg, between 80 mg to 100 mg, between 50 mg to 80 mg, between 0.1 mg to 20 mg, between 0.1 mg to 10 mg, between 0.1 mg to 5 mg, between 0.5 mg to 1.5 mg, between 1.5 mg to 2.5 mg, between 1.5 mg to 5 mg, between 1 mg to 7.5 mg, or between 1 mg to 20 mg. For example, in certain embodiments, the effective amount for exemestane (Arimidex®) may be about 1 mg. In certain embodiments, the effective amount for exemestane (Arimidex®) may be about 100 mg, about 80 mg or about 60 mg.

The effective amount per day of Femara® may vary. For example, the effective amount of letrozole (Femara®) may be between 0.1 mg to 20 mg, such as between 0.1 mg to 10 mg, between 5 mg to 15 mg, between 1 mg to 5 mg, between 2.5 mg to 3 mg, between 2.5 mg to 5 mg, between 2.5 mg to 7.5 mg or between 2.5 mg to 10 mg. In certain embodiments, the effective amount of letrozole (Femara®) may be about 5 mg, about 2.5 mg or about 1 mg.

In certain embodiments, a method is provided for determining if the patient has a breast with a BI-RADS® score of 3 or 4 (or c or d); a breast with a mammographic breast density of 7.5% or greater; a mammographically dense breast; a breast with the same or more breast tissue than fat; a breast with more breast tissue than fat; breast cancer or combinations thereof.

In certain embodiments, the patient has, or is diagnosed with having, a breast with a BI-RADS® score (1-4 scale) in the range of between 2 and 4, for example between 2 and 3, or between 3 and 4. In certain embodiments, the patient has, or is diagnosed with having, a breast with a BI-RADS® score of 2 or more, for example, a BI-RADS® score of 3 or 4, or a BI-RADS® score of 4.

In certain embodiments, the patient has, or is diagnosed with having, a breast with a BI-RADS® score (a-d scale) in the range of between b and d, for example between b and c, or between c and d. In certain embodiments, the patient has, or is diagnosed with having, a breast with a BI-RADS® score of b or more, for example, a BI-RADS® score of c or d, or a BI-RADS® score of d.

In certain embodiments, the patient has, or is diagnosed with having, a breast with a mammographic breast density of 7.5% or greater, for example, a mammographic breast density of 10% or greater, 15% or greater, 20% or greater, 30% or greater, 50% or greater, 70% or greater, or 95% or greater.

In certain embodiments, the patient has, or is diagnosed with having, a breast with a VBD % of 7.5% or greater, for example, a VBD % of 10% or greater, 15% or greater, 20% or greater, 30% or greater, 50% or greater, 70% or greater, or 95% or greater.

In certain embodiments, the patient has, or is diagnosed with having, a breast with a ABD % of 7.5% or greater, for example, a ABD % of 10% or greater, 15% or greater, 20% or greater, 30% or greater, 50% or greater, 70% or greater, or 95% or greater.

In certain embodiments, the patient has, or is diagnosed with having, a breast with a BI-RADS®, score of 3 (or c) and a mammographic breast density of 7.5% or greater, for example, a mammographic breast density of 10% or greater, 15% or greater, 20% or greater, 30% or greater, 50% or greater, 70% or greater, or 95% or greater. In certain embodiments, the patient has, or is diagnosed with having, a breast with a BI-RADS® score of 4 (or d) and a mammographic breast density of 7.5% or greater, for example, a mammographic breast density of 10% or greater, 15% or greater, 20% or greater, 30% or greater, 50% or greater, or greater, or 95% or greater.

In certain embodiments, the patient has, or is diagnosed with having, a breast with a mammographic breast density in the range of between 1% to 100%, for example, a mammographic breast density of between 1% and 24%, between 5% to 100%, between 5% to 95%, between 5% to 90%, between 5% to 80%, between 5% to 70%, between 5% to 60%, between 5% to 50%, between 5% to 40%, between 5% to 30%, between 5% to 25%, between 5% to 20%, between 10% to 100%, between 10% to 95%, between 10% to 90%, between 10% to 80%, between 10% to 70%, between 10% to 60%, between 10% to 50%, between 10% to 40%, between 10% to 30%, between 10% to 25%, between 10% to 20%, between 25% to 100%, between 25% to 75%, between 25% to 50%, between 25% to 49%, between 30% to 100%, between 30% to 95%, between 30% to 90%, between 30% to 80%, between 30% to 70%, between 30% to 60%, between 30% to 50%, between 30% to 40%, between 40% to 100%, between 40% to 95%, between 40% to 90%, between 40% to 80%, between 40% to 70%, between 40% to 60%, between 40% to 50%, between 50% to 100%, between 50% to 95%, between 50% to 90%, between 50% to 80%, between 50% to 75%, between 50% to 74%, between 50% to 70%, between 50% to 60%, between 75% to 100%, between 75% to 95%, or a mammographic breast density of between 75% to 90%.

In certain embodiments, the patient has, or is diagnosed with having, a breast with a VBD % in the range of between 1% to 100%, for example, a VBD % of between 1% and 24%, between 5% to 100%, between 5% to 95%, between 5% to 90%, between 5% to 80%, between 5% to 70%, between 5% to 60%, between 5% to 50%, between 5% to 40%, between 5% to 30%, between 5% to 25%, between 5% to 20%, between 10% to 100%, between 10% to 95%, between 10% to 90%, between 10% to 80%, between 10% to 70%, between 10% to 60%, between 10% to 50%, between 10% to 40%, between 10% to 30%, between 10% to 25%, between 10% to 20%, between 25% to 100%, between 25% to 75%, between 25% to 50%, between 25% to 49%, between 30% to 100%, between 30% to 95%, between 30% to 90%, between 30% to 80%, between 30% to 70%, between 30% to 60%, between 30% to 50%, between 30% to 40%, between 40% to 100%, between 40% to 95%, between 40% to 90%, between 40% to 80%, between 40% to 70%, between 40% to 60%, between 40% to 50%, between 50% to 100%, between 50% to 95%, between 50% to 90%, between 50% to 80%, between 50% to 75%, between 50% to 74%, between 50% to 70%, between 50% to 60%, between 75% to 100%, between 75% to 95%, or a VBD % of between 75% to 90%.

In certain embodiments, the patient has, or is diagnosed with having, a breast with a ABD % in the range of between 1% to 100%, for example, a ABD % of between 1% and 24%, between 5% to 100%, between 5% to 95%, between 5% to 90%, between 5% to 80%, between 5% to 70%, between 5% to 60%, between 5% to 50%, between 5% to 40%, between 5% to 30%, between 5% to 25%, between 5% to 20%, between 10% to 100%, between 10% to 95%, between 10% to 90%, between 10% to 80%, between 10% to 70%, between 10% to 60%, between 10% to 50%, between 10% to 40%, between 10% to 30%, between 10% to 25%, between 10% to 20%, between 25% to 100%, between 25% to 75%, between 25% to 50%, between 25% to 49%, between 30% to 100%, between 30% to 95%, between 30% to 90%, between 30% to 80%, between 30% to 70%, between 30% to 60%, between 30% to 50%, between 30% to 40%, between 40% to 100%, between 40% to 95%, between 40% to 90%, between 40% to 80%, between 40% to 70%, between 40% to 60%, between 40% to 50%, between 50% to 100%, between 50% to 95%, between 50% to 90%, between 50% to 80%, between 50% to 75%, between 50% to 74%, between 50% to 70%, between 50% to 60%, between 75% to 100%, between 75% to 95%, or a ABD % of between 75% to 90%.

In certain embodiments, the patient has, or is diagnosed with having, a mammographically dense breast, for example, a breast having about the same or more breast tissue than fat.

In certain embodiments, the patient is a peri-menopausal woman or a post-menopausal woman. In certain embodiments, the patient is a perimenopausal woman.

In certain embodiments, the duration of treatment for administration of an androgenic agent, an aromatase inhibitor, or a pharmaceutical composition a combination of the same, may vary between about 1 week to about 20 years, for example, between about 1 month to about 20 years, between about 3 months to about 10 years, between about 4 months to about 5 years, and between about 6 months to about 4 years. In certain embodiments, the duration of treatment may be about 3 months, 6 months, about 9 months, about 1 year, 1.5 years, 2 years, 2.5 years, 3 years, 3.5 years, 4 years, 4.5 years, 5 years, 5.5 years, 6 years, 7 years, 10 years, 13 years, 15 years, or 20 years.

In certain embodiments, the method reduces or decreases the patient's BT-RADS® score between one or more annual intervening mammographic detections. For example, the method reduces or decreases the patient's BI-RADS® score by 1 or more points between one or more annual intervening mammographic detections, such as, by 2 or more, 3 or 4, or 4 points between one or more annual intervening mammographic detections. In certain embodiments, the method reduces or decreases the patient's BI-RADS® score by 1 point between one or more annual intervening mammographic detections, for example, by 2, 3, or 4 points between one or more annual intervening mammographic detections. In certain embodiments, the method maintains or stabilizes the patient's BI-RADS® score between one or more annual intervening mammographic detections.

The time period between the one or more annual intervening mammographic detections may be 1 to 20 years, for example, 1 year, 1.5 years, 2 years, 3 years, 4 years, 5 years, 6 years, 10 years, 15 years, or 20 years. The time period between the one or more annual intervening mammographic detections may be 1 year, 2 years, 4 years, 5 years, 7 years, 10 years, 15 years, or 20 years.

In certain embodiments, the method reduces or decreases the mammographic breast density of the patient's breast between one or more annual intervening mammographic detections. In certain embodiments, the method reduces or decreases the VBD % and/or AVBD of the patient's breast between one or more annual intervening mammographic detections. In certain embodiments, the method reduces or decreases the ABD % and/or AABD of the patient's breast between one or more annual intervening mammographic detections. For example, the method reduces or decreases the mammographic breast density of the patient's breast in the range of between 1% to 99% between one or more annual intervening mammographic detections, such as, in the range of between 1% to 80%, between 1% to 50%, between 1% to 30%, between 1% to 20%, between 1% to 10%, between 3% to 40%, between 3% to 20%, between 5% to 60%, between 5% to 25%, between 5% to 15%, between 5% to 10%, between 10% to 60%, between 10% to 40%, between 10% to 30%, between 10% to 20%, between 10% to 15%, between 20% to 60%, between 20% to 40%, between 20% to 30%, between 30% to 60%, between 30% to 50%, or between 30% to 40% between one or more annual intervening mammographic detections. For example, the method reduces or decreases the VBD % and/or AVBD of the patient's breast in the range of between 1% to 99% between one or more annual intervening mammographic detections, such as, in the range of between 1% to 80%, between 1% to 50%, between 1% to 30%, between 1% to 20%, between 1% to 10%, between 3% to 40%, between 3% to 20%, between 5% to 60%, between 5% to 25%, between 5% to 15%, between 5% to 10%, between 10% to 60%, between 10% to 40%, between 10% to 30%, between 10% to 20%, between 10% to 15%, between 20% to 60%, between 20% to 40%, between 20% to 30%, between 30% to 60%, between 30% to 50%, or between 30% to 40% between one or more annual intervening mammographic detections. For example, the method reduces or decreases the ABD % and/or AABD of the patient's breast in the range of between 1% to 99% between one or more annual intervening mammographic detections, such as, in the range of between 1% to 80%, between 1% to 50%, between 1% to 30%, between 1% to 20%, between 1% to 10%, between 3% to 40%, between 3% to 20%, between 5% to 60%, between 5% to 25%, between 5% to 15%, between 5% to 100, between 10% to 60%, between 10% to 40%, between 10% to 30%, between 10% to 20%, between 10% to 15%, between 20% to 60%, between 20% to 40%, between 20% to 30%, between 30% to 60%, between 30% to 50%, or between 30% to 40% between one or more annual intervening mammographic detections. For example, the method reduces or decreases the mammographic breast density of the patient's breast by at least 2% between one or more annual intervening mammographic detections, such as, by at least 5%, 10%, 20%, 30%, 40%, 50%, 75%, 85%, 95%, or 99% between one or more annual intervening mammographic detections. For example, the method reduces or decreases the VBD % and/or AVBD of the patient's breast by at least 2% between one or more annual intervening mammographic detections, such as, by at least 5%, 10%, 20%, 30%, 40%, 50%, 75%, 85%, 95%, or 99% between one or more annual intervening mammographic detections. For example, the method reduces or decreases the ABD % and/or AABD of the patient's breast by at least 2% between one or more annual intervening mammographic detections, such as, by at least 5%, 10%, 20%, 30%, 40%, 50%, 75%, 85%, 95%, or 99% between one or more annual intervening mammographic detections. In certain embodiments, the method maintains or stabilizes the mammographic breast density of the patient's breast between one or more annual intervening mammographic detections.

In certain embodiments, the method reduces or decreases the mammographic breast density of the patient's breast by at least 2%, such as 5%, 10%, 20%, or 30%, over a 4 hour period, such as over an 8 hour, 24 hour, 1 day, 3 days, 1 week, 2 weeks, 1 month, 2 month, 3 months, 6 months, 9 months, or 1 year period.

In certain embodiments, the method reduces or decreases the mammographic breast density VBD % and/or AVBD of the patient's breast by at least 20, such as 5%, 10%, 20%, or 30%, over a 4 hour period, such as over an 8 hour, 24 hour, 1 day, 3 days, 1 week, 2 weeks, 1 month, 2 month, 3 months, 6 months, 9 months, or 1 year period.

In certain embodiments, the method reduces or decreases the mammographic breast density ABD % and/or AABD of the patient's breast by at least 2%, such as 5%, 10%, 20%, or 30%, over a 4 hour period, such as over an 8 hour, 24 hour, 1 day, 3 days, 1 week, 2 weeks, 1 month, 2 month, 3 months, 6 months, 9 months, or 1 year period.

In certain embodiments, the method mitigates or reduces the patient's risk of developing breast cancer. For example, in certain embodiments, the method mitigates, reduces or the patient's risk of developing breast cancer between one or more annual intervening mammographic detections. In certain embodiments, the method mitigates, reduces or the patient's risk of developing breast cancer and avoids, mitigates, reduces or reverses one or more peri-menopausal symptoms between one or more annual intervening mammographic detections. For example, the one or more peri-menopausal symptoms that may be mitigated, reduced, or avoided may include, but is not limited to, menstrual irregularity; hot flashes and sleep problems; mood changes; mood swings; irritability; depression; vaginal dryness; urinary or vaginal infections; urinary incontinence; decreasing fertility; changes in sexual arousal or desire; bone loss; fragile bones; osteoporosis; or changing cholesterol levels, such as an increase in low-density lipoprotein (LDL) cholesterol, a decrease in high-density lipoprotein (HDL) cholesterol; or combinations thereof.

In certain embodiments, the method increases or improves the patient's fat to breast tissue ratio between one or more annual intervening mammographic detections. For example, the method increases or improves the patient's fat to breast tissue ratio from 1:19 to 19:1 between one or more annual intervening mammographic detections, such as increases or improves the treated patient's fat to breast tissue ratio from 1:15 to 19:1, from 1:10 to 19:1, from 1:5 to 19:1, from 1:2 to 19:1, from 2:3 to 19:1, from 2:1 to 19:1, from 4:1 to 19:1, from 6:1 to 19:1, from 8:1 to 19:1, from 10:1 to 19:1, from 1:19 to 10:1, from 1:10 to 10:1, from 1:4 to 10:1, from 1:2 to 10:1, from 3:2 to 10:1, from 3:1 to 10:1, from 5:1 to 10:1, from 7:1 to 10:1, from 9:1 to 10:1, from 15:1 to 10:1, from 1:15 to 5:1, from 1:5 to 5:1, from 1:3 to 5:1, from 3:2 to 5:1, from 3:1 to 5:1, from 6:1 to 5:1, 8:1 to 5:1, from 10:1 to 5:1, from 1:19 to 3:1, from 1:10 to 3:1, from 1:4 to 3:1, from 1:2 to 3:1, from 2:1 to 3:1, from 4:1 to 3:1, from 6:1 to 3:1, from 8:1 to 3:1, from 10:1 to 3:1, or from 15:1 to 3:1 between one or more annual intervening mammographic detections.

In certain embodiments, the method increases or improves the patient's fat to breast tissue ratio from 1:19 to 19:1, such as from 1:10 to 19:1, from 1:5 to 19:1, from 1:2 to 19:1, from 2:3 to 19:1, from 2:1 to 19:1, over a 4 hour period, over an 8 hour period, over a 24 hour period, over a 3 day period, over a 1 week period, over a 2 week period, over a 1 month period, over a 2 month period, over a 3 month period, over a 6 month period, over a 9 month period, over a 1 year period, or over a 5 year period.

In certain embodiments, the method increases the percentage of fat in the treated patient's breast between one or more annual intervening mammographic detections. For example, the method increases the percentage of fat in the treated patient's breast in the range of between 1% to 99% between one or more annual intervening mammographic detections, such as, in the range of between 1% to 99%, between 1% to 70%, between 1% to 50%, between 1% to 30%, between 1% to 20%, between 1% to 15%, between 1% to 10%, between 3% to 60%, between 3% to 20%, between 5% to 70%, between 5% to 50%, between 5% to 30%, between 5% to 20%, between 5% to 15%, between 5% to 10%, between 10% to 60%, between 10% to 40%, between 10% to 30%, between 10% to 20%, between 10% to 15%, between 20% to 50%, between 20% to 30%, between 30% to 60%, between 30% to 50%, or between 30% to 40% between one or more annual intervening mammographic detections.

In certain embodiments, the method increases the percentage of fat in the treated patient's breast by at least 2%, such as by at least 5%, by at least 10%, by at least 25%, by at least 40%, by at least 75%, by at least 95%, or by at least 99%, over a 4 hour period, such as over an 8 hour period, over a 24 hour period, over a 3 day period, over a 1 week period, over a 2 week period, over a 1 month period, over a 2 month period, over a 3 month period, over a 6 month period, over a 9 month period, over a 1 year period, or over a 5 year period.

In certain embodiments, the method enhances, increases, or improves, breast compression during mammographic visualization or detection of the breast between one or more annual intervening mammographic detections. For example, the method enhances, increases, or improves, breast compression during mammographic visualization or detection of the breast in the range of between 5% to 70%, between 5% to 50%, between 5% to 30%, between 5% to 20%, between 5% to 15%, between 5% to 10%, between 10% to 50%, between 10% to 30%, between 10% to 20%, between 10% to 15%, between 20% to 60%, between 20% to 40%, between 20% to 30%, between 30% to 70%, between 30% to 50%, or between 30% to 40% between one or more annual intervening mammographic detections. In certain embodiments, as a result of the enhanced, increased, or improved, breast compression during mammographic visualization or detection of the breast, the method further mitigates or reduces the patient's pain during the breast compression. For example, the method further mitigates, reduces or minimizes, the patient's pain during the breast compression in the range of between 5% to 80%, between 5% to 50%, between 5% to 30%, between 5% to 20%, between 5% to 15%, between 5% to 10%, between 10% to 80%, between 10% to 60%, between 10% to 40%, between 10% to 20%, between 10% to 15%, between 20% to 70%, between 20% to 50%, between 20% to 30%, between 30% to 70%, between 30% to 50%, or between 30% to 40% less pain as a result of the enhanced, increased, or improved, breast compression during mammographic visualization or detection of the breast.

In certain embodiments, the method mitigates or reduces the patient's pain during the breast compression. For example, the method mitigates or reduces the patient's pain during the breast compression in the range of between 5% to 80%, between 5% to 60%, between 5% to 30%, between 5% to 20%, between 5% to 15%, between 5% to 10%, between 10% to 80%, between 10% to 60%, between 10% to 40%, between 10% to 30%, between 10% to 20%, between 10% to 15%, between 20% to 70%, between 20% to 50%, between 20% to 30%, between 30% to 90%, between 30% to 50%, or between 30% to 40% between one or more annual intervening mammographic detections. In certain embodiments, as a result of the patient's mitigated, reduced or minimized pain during the breast compression, the method further enhances, increases, or improves, breast compression during mammographic visualization or detection of the breast between one or more annual intervening mammographic detections. For example, the method further enhances, increases, or improves, breast compression during mammographic visualization or detection of the breast between one or more annual intervening mammographic detections in the range of between 5% to 80%, between 5% to 60%, between 5% to 40%, between 5% to 30%, between 5% to 20%, between 5% to 15%, between 5% to 10%, between 10% to 80%, between 10%, to 60%, between 10% to 40%, between 10% to 20%, between 10% to 15%, between 20% to 80%, between 20% to 60%, between 20% to 30%, between 30% to 80%, between 30% to 50%, or between 30% to 40% between one or more annual intervening mammographic detections.

In certain embodiments, the method mitigates or reduces the patient's pain according to the visual analog scale (VAS) during the breast compression. For example, the method mitigates or reduces the patient's pain according to the VAS during the breast compression such that the patient does not suffer from significant pain between 50-100 mm, between 50-80 mm, between 50-70 mm, between 60-100 mm, between 70-100 mm, between 80-100 mm or between 90-100 mm during one or more mammographic detections or during one or more annual intervening mammographic detections.

In certain embodiments, the method enhances increases or improves the patient's compliance of having regular mammographic visualizations or detections, for example, compliance with mammographic visualizations or detections at every 6 months, annually, every 2 years, every 3 years, or every 5 years.

In certain embodiments, the method mitigates or reduces the amount of radiation exposure required to visualize or detect the patient's breast during one or more subsequent mammographies, such as during one or more subsequent annual mammographies. For example, the method mitigates or reduces the amount of radiation exposure required to visualize or detect the patient's breast in the range of between 5% to 99%, between 5% to 80%, between 5% to 70%, between 5% to 50%, between 5% to 30%, between 5% to 20%, between 5% to 15%, between 5% to 10%, between 10% to 80%, between 10% to 60%, between 10% to 40%, between 10% to 20%, between 10% to 15%, between 20% to 80%, between 20% to 60%, between 20% to 40%, between 20% to 30%, between 30% to 80%, between 30% to 60%, between 30% to 50% or between 30% to 40% during one or more subsequent mammographies, such as during one or more subsequent annual mammographies.

In certain embodiments, the method induces breast involution in the breast of the patient, for example in the breast of a peri-menopausal patient.

In certain embodiments, the method induces involution of breast cells in the breast of the patient, for example in the breast of a peri-menopausal patient.

In certain embodiments, the method induces net cell death over proliferation in the breast of the patient, for example in the breast of a peri-menopausal patient.

In certain embodiments, the method reverses cell number and mammographic breast density in the breast of the patient, for example in the breast of a peri-menopausal patient.

In certain embodiments, the method mitigates or reduces breast stiffness in the breast of the patient, for example in the breast of a peri-menopausal patient. For example, the method mitigates or reduces breast stiffness in the breast of the patient in the range of between 5% to 80%, between 5% to 60%, between 5% to 40%, between 5% to 20%, between 5% to 15%, between 5% to 10%, between 10% to 80%, between 10% to 60%, between 10% to 40%, between 10% to 30%, between 10% to 20%, between 10% to 15%, between 20% to 80%, between 20% to 60%, between 20% to 40%, between 20% to 30%, between 30% to 80%, between 30% to 60%, or between 30% to 40%, between one or more annual intervening mammographic detections. For example, the method mitigates or reduces breast stiffness in the breast of the patient by at least 5%, such as at least 8%, at least 10%, at least 15%, at least 20%, or at least 30%, per annum. In certain embodiments, the method mitigates or reduces breast stiffness in the breast of the patient by at least 5%, such as at least 8%, at least 10%, at least 15%, at least 20%, or at least 30%, over a 4 hour period, such as over an 8 hour period, a 24 hour period, a 3 day period, a 1 week period, a 2 week period, a 1 month period, a 2 month period, a 3 month period, a 6 month period, a 9 month period, a 1 year period, or a 5 year period.

In certain embodiments, the method enhances, increases, or improves mammographic visualization or detection of the breast of the patient, for example the breast of a peri-menopausal patient. For example, the method enhances, increases, or improves mammographic visualization or detection of the breast of the patient in the range of between 5% to 80%, between 5% to 50%, between 5% to 30%, between 5% to 20%, between 5% to 15%, between 5% to 10%, between 10% to 80%, between 10% to 60%, between 10% to 30%, between 10% to 20%, between 10% to 15%, between 20% to 80%, between 20% to 60%, between 20% to 30%, between 30% to 80%, between 30% to 60%, or between 30% to 40%, between one or more annual intervening mammographic detections. In certain embodiments, the method enhances, increases, or improves mammographic visualization or detection of the breast of the patient by at least 5%, such as at least 100, at least 15%, at least 25%, at least 40%, at least 50%, or at least 75%, over a 4 hour period, or over other time periods, such 8 hours, 24 hours, 3 days, 1 week, 2 weeks, 1 month, 2 month, 3 months, 6 months, 9 months, 1 year, or 5 years.

In certain embodiments, the method reduces mammographic breast density and avoids inducing masculinizing androgenic side-effects or inducing a hyper-androgenic state. For example, masculinizing androgenic side-effects may include male-type baldness, hirsutism, or increased hair in areas unwanted by said patient, voice deepening, acne, or combinations thereof. In certain embodiments, the method reduces mammographic breast density and is exclusive of inducing masculinizing androgenic side-effects or inducing a hyper-androgenic state. In certain embodiments, the method reduces mammographic breast density and minimizes induction of masculinizing androgenic side-effects or induction of a hyper-androgenic state.

In certain embodiments, the method substantially improves or improves the patient's physical functioning, such as physical functioning related to the patient's central nervous system, libido, musculoskeletal system, cardiovascular system, risk of contracting autoimmune diseases, severity of symptoms associated with autoimmune disease, or combinations thereof. For example, as related to the patient's central nervous system, the method may reduce depression, anxiety, general cognitive dysfunction including memory, or reduce the risk of dementia and Parkinsonism. For example, as related to the patient's libido, the method may provide a significant improvement in global libido, including speed to sexual arousal and ability to achieve orgasm. For example, as related to the patient's musculoskeletal system, the method may provide for a reduction in inflammatory and degenerative arthritis, an improvement in bone mineral density, or an improvement in muscle strength. For example, as related to the patient's cardiovascular system, the method may provide a reduction in foamy macrophage deposition in the arterial wall, a reduction in atherosclerosis, an increase in high density lipoprotein's leading to an improvement in cholesterol, or a high density lipoprotein ratio. For example, as related to the patient's risk of contracting autoimmune diseases, the method may substantially reduces or reduces the treated patient's risk of contracting autoimmune diseases, such as Sjogren's syndrome, lupus, and rheumatoid arthritis. For example, as related to the severity of symptoms associated with the patient's autoimmune disease, the method may substantially reduces or reduces the severity of symptoms associated with a treated patient's autoimmune disease, such as Sjogren's syndrome, lupus, and rheumatoid arthritis. In certain embodiments, the method substantially improves or improves the patient's physical functioning, such as cognitive function; reduction of a degenerative CNS disease, comprising dementia or parkinsonism; muscle strength; libido; energy; reduction of monoamine oxidase induced anxiety and depression; or combinations thereof.

In certain embodiments, the method further provides one or more of the following: i) reduces mammographic breast density; ii) increases involutionary effects on the patient's breast without conversion of testosterone to estrogen; iii) substantially reduces, reduces, or reverses peri-menopausal symptoms; or iv) substantially improves or improves the patient's physical functioning, comprising cognitive function; reduction of symptoms associated with a degenerative CNS disease, comprising dementia or parkinsonism; muscle strength; libido; energy: reduction of monoamine oxidase induced anxiety and depression; or combinations thereof. In certain embodiments, the method further provides one or more of the following: i) reduces mammographic breast density; ii) increases involutionary effects on hormonally affected end organs, comprising breast, without conversion of testosterone to estrogen; iii) substantially reduces, reduces, or reverses peri-menopausal symptoms related to fluctuating estrogen levels; or iv) substantially improves or improves the patient's physical functioning, comprising cognitive function, reduction of symptoms associated with a degenerative CNS disease, comprising dementia or parkinsonism; muscle strength; libido; energy; reduction of monoamine oxidase induced anxiety and depression; or combinations thereof.

In certain embodiments, the patient has a high free androgenic index level, for example 30% or greater, within their breast within four hours of the administration of the androgenic agent and the aromatase inhibitor. In certain embodiments, the patient has a supra-physiological free androgenic index level within their breast within four hours of the administration of the androgenic agent and the aromatase inhibitor.

In certain embodiments, the method further comprises: a) measuring free androgenic index levels and/or aromatase inhibitor levels in serum isolated from a blood sample taken from the patient after at least 1 month of treatment; b) determining a subsequent dose, comprising a subsequent effective amount of androgenic agent and a subsequent effective amount of an aromatase inhibitor; and c) administering to the patient the subsequent dose.

In certain embodiments, the method further comprises: a) measuring free androgenic index levels and/or aromatase inhibitor levels in serum isolated from a blood sample taken from the patient after at least 1 month of treatment, comprising centrifuging the patient's blood sample to isolate the serum; b) determining a subsequent dose, comprising a subsequent effective amount of androgenic agent and a subsequent effective amount of an aromatase inhibitor, and c) administering to the patient the subsequent dose.

In certain embodiments, the measured free androgenic index serum levels of a treated patient after 1 month may be between 10-25%, such as between 10-20%, between 10-15%, between 15-25%, between 15-20%, between 12-18%, between 8-15%, or between 11-14%.

In certain embodiments, the measured free androgenic index serum levels of a treated patient after 3 months may be between 2-10%, such as between 2-8%, between 2-6%, between 2-5%, between 2-4%, between 4-10%, between 5-8%, between 3-7%, between 4-6%, between 3-6%, between 4-7%, between 5-10% or between 2-5%.

In certain embodiments, the administration of the aromatase inhibitor reduces aromatization of testosterone to estrogen in the subcutaneous fat of the treated patient, for example reduces aromatization by 80-95%, or 100%. For example, the administered aromatase inhibitor may reduce aromatization of testosterone to estrogen in the subcutaneous fat of the patient's breast, the subcutaneous fat of the patient's pelvis, the subcutaneous fat of the patient's buttocks, the subcutaneous fat of the patient's abdomen or combinations thereof, for example reduces aromatization by 80-95%, or 100%.

In certain embodiments, the administration of the aromatase inhibitor reduces aromatization of adrenal androgens, for example androstenedione, to estrogen in the subcutaneous fat of the treated patient, for example reduces aromatization by 80-95%, or 100%. For example, the administered aromatase inhibitor may reduce aromatization of testosterone to estrogen in the subcutaneous fat of the patient's breast, the subcutaneous fat of the patient's pelvis, the subcutaneous fat of the patient's buttocks, the subcutaneous fat of the patient's abdomen or combinations thereof, for example reduces aromatization by 80-95%, or 100%.

In certain embodiments, the administration of the androgenic agent and the aromatase inhibitor is a co-administration. For example, the co-administration may be concurrently, simultaneously, substantially at the same time, or sequentially.

Dosing Algorithm

Certain embodiments involves the identification of women in the peri-menopause who have mammographically dense breast tissue as described by an appropriate mathematical algorithm produced from pre-presentation mammographic images, who are then treated with testosterone 1 mg to 200 mg combined with a third-generation Ai such as but not confined to anastrozole or letrozole (0.5-20 mg) and administered by subcutaneous application.

In certain embodiments, the anastrozole dose (AD) and the testosterone dose (TD), both measured in mg, are given as a function of the following formulas $$AD = F1(N,T,BW,TBF,MBD\ BS,AGE,FAI(T),AI(T),TD) \quad \text{Formula 1}$$

$$TD = F2(N,T,BW,TBF,MBD\ BS,AGE,SAL(T),AI(T)) \quad \text{Formula 2}$$

wherein:
N is the dose number (N=1 being the first dose);
T is time in months from the first dose;
BW is body weight measured in kg;
TBF is fraction of BW measured by bio-impedance;
MBD is mammographic breast density, being the percentage of breast fibro-glandular tissue relative to total breast volume where the MBD is the average of both breasts, e.g., measured by Volpara breast density software;
Age=years;
AI(T) is the Androgenicity Index as a function of time which is given by:

$$AI(T) = F3(H,A,VD,SHL) \quad \text{Formula 3}$$

wherein each of the parameters is measured at time T and
H is a measure of Hirutism;
A is a measure of Acne;
VD is measure of Voice Deepening;
SHL is a measure of Scalp Hair Loss;
FAI(T) is the Free Androgen Index measured at time T; in one embodiment, FAI is given by $$FAI(T) = 100 \times TT/SHBG \quad \text{Formula 4}$$

wherein the variables are measured at time T and
TT is the patient's Total Testosterone level and
SHBG is the patient's Sex Hormone Binding Globulin level;
TD is the dose of Androgenic Agent being administered at the same time as the AD dose.
BS is a measure of Breast Stiffness averaged across both breasts; and
SAL(T) is the Serum Aromatase Level of measured in ng/ml at time T; and
wherein each parameters is measured just prior to the dose number N, except for FAI(T), AI(T) and SAL(T), which are calculated at specified times T related to the dose number N.

In certain embodiments, H, A, VD and SHL are measured on a baseline visual analog scale of 0 to 100 mm. In certain embodiments, BS is measured in Newtons per centimetre using the algorithm of Boyd et al. (2014).

F1 is a drug specific function having the following characteristics: (1) F1 is non-increasing in the following parameters: BW, TBF, AGE (wherein non-increasing is understood to mean, for example, if the other parameters are held constant and BW is increased then the resulting AD calculated with F1 will either stay the same or decrease), and/or (2) F1 is non-decreasing in MBD, BS (wherein non-decreasing is understood to mean, for example, if the other parameters are held constant and BS is increased then the resulting AD calculated with F1 will either stay the same or decrease).

F2 is a drug specific function having the following characteristics: (1) F2 is a non-increasing function of AGE; and/or (2) F2 is a non-decreasing function of BW, TBF, MBD, BS.

F3 is an increasing function of H, A, VD and SHL.

In certain embodiments, one or more functional forms of F1, F2 and F3 may provide acceptable dosages when calibrated to the pharmacokinetic and other characteristics of the specifically chosen androgenic agent and aromatase inhibitor.

In one embodiment the following functional forms have been proven effective where the androgenic agent is testosterone (T) and the aromatase inhibitor (Ai) is anastrozole and doses are given at 4 monthly intervals:

F1:

$$AD=V1(N) \times (C1 \times 1/BW \times 1/TBF \times MBD + C2 \times (C3/AGE) + V2(N))$$ Formula 1A wherein MBD is the average for both breasts of the percentage of breast fibro-glandular tissue relative to total breast volume and C1, C2 and C3 are constants and V1(N) and V2(N) are defined below;

F2:

$$TD=V1(N) \times (C4 \times BW \times TBF \times MBD + C5 \times (C3-AGE) + V3(N))$$ Formula 2A wherein C4 and C5 are constants and V3(N) is described below; and

F3:

$$AI=(H+A+VD+SHL)/4$$ Formula 3A wherein H, A, VD and SHL are measured on a baseline visual analog scale of 0 to 100 mm and then reevaluated at the one year MBD measurement.

In some embodiments, the dosing algorithm provided above may also be used with VBD % averaged across both breasts. In other words, VBD % averaged across both breasts may be substituted for MBD in the above discussed dosing algorithm.

In certain embodiments, one or more of these parameters are optimised according to the individual patient to achieve the following optimal outcomes on average: FAI of 15% at one month after a dose and 5% at 3 months after a dose; and/or SAL of 35 mg/ml at 1 month after a dose and 25 mg/ml at 3 months after a dose.

In certain embodiments, one or more of these parameters are optimised according to the individual patient to achieve the following optimal outcomes on average: FAI of 15% at one month after a dose and 5% at 3 months after a dose; and/or SAL of 35 mg/ml at 1 month after a dose and 25 mg/ml at 3 months after a dose, wherein a reduction of MBD, of at least 2% per annum is constrained by the dose of the AI not increasing more than 10% in that year.

In certain embodiments, one or more of these parameters are optimised according to the individual patient to achieve the following optimal outcomes on average: FAI of 15% at one month after a dose and 5% at 3 months after a dose, and/or SAL of 35 mg/ml at 1 month after a dose and 25 mg/ml at 3 months after a dose; wherein a reduction of VBD %, of at least 2% per annum is constrained by the dose of the AI not increasing more than 10% in that year.

Using the above dosing functional forms as a starting point and known pharmacokinetic and activity profile differences, the constants in the functional forms or the functional forms may be adjusted to provide a starting point for adjusting constants to achieve the optimal outcomes specified above when using different aromatase inhibitors and androgenic agents.

The subsequent dosing is modified by reference to the following serum levels achieved:

TD increase or decrease (V3(N) in the above) in 4 month dosage is determined by achieving the optimal 1 month FAI of 15% and 3 months FAI of 5% such that the mg dosage of TD is +/−4 mg for each FAI % point above or below 10 (i.e. 1 month FAI-3 month FAI).

AD increase or decrease (V2(N) in the above) in 4 month dosage is determined by achieving an optimal serum anastrozole level of 35 mg/ml at 1 month and 25 mg/ml at 3 months such that AD is increased or decreased 0.1 mg for each ng/ml above or below the 10 (i.e. 1 month serum anastrozole level −3 month serum anastrozole level)

Annual mammographic screening of density may be undertaken to determine reduction in breast density utilizing an appropriate mammographic algorithm that measures the volume of fibro-glandular tissue as percentage of total breast volume (MBD). The objective is to achieve MBD of less than 10% when this is a function of the average of both breast densities. The rate of breast density reduction should be at least 2% per annum. An annual uplift factor (V1(N) in the above) may be introduced into TD and AD of 10% of dosing if 2% is not achieved in the first year. This annual uplift factor typically will only be introduced, on an annual basis, if there is less than 10% increase in androgenicity index (AI).

Annual mammographic screening of density may be undertaken to determine reduction in breast density utilizing an appropriate mammographic algorithm that measures the volume of fibro-glandular tissue as percentage of total breast volume (VBD %). The objective is to achieve VBD % of less than 10% when this is a function of the average of both breast densities. The rate of breast density reduction (VBD %) should be at least 2% per annum. An annual uplift factor (V1(N) in the above) may be introduced into TD and AD of 10% of dosing if 2% is not achieved in the first year. This annual uplift factor typically will only be introduced, on an annual basis, if there is less than 10% increase in androgenicity index (AI).

In certain embodiments, dosage levels below the lower limit of the aforesaid range of the aromatase inhibitor may be more than adequate, while in other cases still larger doses above the upper limit of the aforesaid range may be employed without causing harmful side effects. For example, dosages of an aromatase inhibitor above the upper limit may be used to improve the bioavailability of an androgenic agent, such as testosterone or dihydrotestosterone, as described herein.

Testosterone naturally is not highly absorbed because it is broken down approximately 85% in the intestines by aromatase and other metabolic pathways into by-products such as inactive testosterone and dihydrotestosterone. The administration of an aromatase inhibitor in combination with testosterone, however, results in an increased absorption, and subsequently greater bioavailability.

In certain embodiments, the administration of an aromatase inhibitor in combination with testosterone results in an improvement in the bioavailability of testosterone between 10% to 50%, between 20% to 40%, or between 25% to 35%. In certain embodiments, the amount of increase in bioavailability of testosterone is greater than 15%, greater than 25%, greater than 30% or greater than 35%.

In certain embodiments, the administration of aromatase inhibitor in combination with testosterone results in an improvement in the bioavailability of dihydrotestosterone between 25% to 75%, between 35% to 65% or between 45% to 55%. In certain embodiments, the amount of increase in bioavailability of dihydrotestosterone is greater than 25%, greater than 35%, greater than 45% or greater than 55%.

In certain embodiments, the method may include administering a pharmaceutical composition comprising an androgenic agent and an aromatase inhibitor. The androgenic agent, for example, may be selected from the group consisting of testosterone, methyltestosterone, testosterone undecanoate, testosterone propionate, or a selective androgen receptor modulator. In certain embodiments, the androgenic agent may be testosterone undecanoate, such as about 40 mg of testosterone undecanoate. The aromatase inhibitor, for example, may be selected from the group consisting of exemestane, formestane, anastrozole, letrozole, vorozole, or fadrozole. In certain aspects, the aromatase inhibitor may be anastrozole, such as about 1 mg of anastrozole. In certain embodiments, the method comprises administering a pharmaceutical composition comprising about 40 mg of testosterone undecanoate and about 1 mg of anastrozole.

In certain embodiments, the method may include administering a pharmaceutical composition comprising an androgenic agent linked to an aromatase inhibitor, e.g., via an ester linkage, or an androgenic agent/aromatase inhibitor complex, wherein the complex is created by methods in the art.

The route of administering an androgenic agent, an aromatase inhibitor, or a pharmaceutical composition comprising the androgenic agent and the aromatase inhibitor may be by one or more routes compatible with a desired outcome. For example, the routes of administration include orally (e.g., ingestion or inhalation), intraperitoneally, intradermally, transdermally, transmucosally, subcutaneously, sublingually, intravenously, intraarterially, intracavity, intracranially, intramuscularly, parenterally, or topically. In certain embodiments, the aromatase inhibitor and the androgenic agent are administered orally, transdermally, or subcutaneously.

The pharmaceutically acceptable agents are administered alone or in combination with pharmaceutically acceptable carriers, excipients, or diluents, and such administration may be carried out in single or multiple doses. The therapeutic agents may be administered in a wide variety of different dosage forms, i.e., they may be combined with various pharmaceutically acceptable inert carriers or excipients in the form of tablets, capsules, emulsions, lozenges, troches, hard candies, lollipops, powders, sprays, creams, salves, suppositories, jellies, gels, pastes, lotions, ointments, aqueous suspensions, injectable solutions, elixirs, syrups, injectable depots, implants, microencapsulated delivery systems, oil-based suspensions, and the like.

For example, androgenic agents may be administered by the aforementioned routes and dosage forms. In one embodiment, testosterone esters may be injected. These may include testosterone enanthate (Delatestryl) which is suspended in sesame oil, testosterone cypionate (Depo-Testosterone) which is suspended in cottonseed oil, testosterone propionate (Testovis; Virormone), testosterone phenylpropionate (Testolent), and a blend of four testosterone esters (Sustanon; Omnadren) which include testosterone propionate, testosterone phenylpropionate, testosterone isocaproate, and testosterone decanoate.

In another embodiment, testosterone may be injected as an aqueous suspension (Aquaviron). In another embodiment, testosterone may be administered via a transdermal patch (Androderm; Testoderm TTS). In another embodiment, testosterone may be administered by a gel (Androgel; Testim). In another embodiment, methyltestosterone may be administered orally, e.g., tablet (Metesto, Methitest, Testred, Oreton Methyl, and Android). In another embodiment, testosterone undecanoate may be administered orally, e.g., tablet (Androxon, Understor, Restandol, and Restinsol). In one embodiment, testosterone may be administered buccally (Striant). In another embodiment, testosterone may be administered subcutaneously, e.g., pellet (Testopel).

In certain embodiments, the pharmaceutical combinations comprising an aromatase inhibitor in combination with an androgenic agent include administration of a single pharmaceutical dosage formulation which contains both substances, as well as administration of each agent in its own separate pharmaceutical dosage formulation.

In certain embodiments, both the androgenic agent (e.g., testosterone, methyltestosterone, testosterone undecanoate, testosterone propionate, or a selective androgen receptor modulator), and the aromatase inhibitor (e.g., anastrozole, exemestane, or letrozole) are administered orally, e.g., tablet or capsule. For example, both testosterone and anastrozole are administered orally. For example anastrozole (2,2'-[5-(1H-1,2,4-triazol-1-ylmethyl)-1,3-phenylene]bis(2-methylpropanenitrile)) orally as a tablet once a day in combination with (2S)-3-(4-cyanophenoxy)-N-[4-cyano-3-(trifluoromethyl)phenyl]-2-hydroxy-2-methylpropanamide (also known as Enobosarm, Ostarine, GTx-024, and MK-2866). For example letrozole (4,4'-((1H-1,2,4-triazol-1 yl)methylene)dibenzonitrile) orally as a tablet once a day in combination with (4-((R)-2-((R)-2,2,2-trifluoro-1-hydroxyethyl) pyrrolidin-1-yl)-2-trifluoromethyl)benzonitrile (also known as LGD-4033, or Ligandrol). For example exemestane, 6-Methylideneandrosta-1,4-diene-3,17-dione orally as a tablet once a day in combination with (4-[(7R,7aS)-7-hydroxy-1,3-dioxo-5,6,7,7a-tetrahydropyrrolo[1,2-c]imidazol-2-yl]-2-chloro-3-methylbenzonitrile (also known BMS-564929). For example anastrozole (2,2'-[5-(1H-1,2,4-triazol-1-ylmethyl)-1,3-phenylene]bis(2-methylpropanenitrile)) orally as a tablet once a day in combination with at least one of the following amounts of a Tetrahydroquinolone androgenic agent such as (3aS,4S,9bS)—N-[2-(8-Cyano-1-formyl-2,3,3a,4,5,9b-hexahydro-1H-pyrrolo[3,2-c]quinolin-4-yl)-2-methylpropyl]-4,6-difluorobenzofuran-2-carboxyamide (also known as S-101479).

In some embodiments, both the androgenic agent (e.g., testosterone, methyltestosterone, testosterone undecanoate, testosterone propionate, or a selective androgen receptor modulator), and the aromatase inhibitor (e.g., anastrozole, exemestane, or letrozole) are administered transdermally, e.g., patch. For example, both testosterone and anastrozole are administered transdermally.

In some embodiments, both the androgenic agent (e.g., testosterone, methyltestosterone, testosterone undecanoate, testosterone propionate, or a selective androgen receptor modulator), and the aromatase inhibitor (e.g., anastrozole, exemestane, or letrozole) are administered subcutaneously, e.g., pellet. For example, both testosterone and anastrozole are administered subcutaneously.

Patient compliance is a factor in receiving a good result in medical treatment. Causes for poor compliance may include, but are not limited to, complicated regimen, unattractive and/or painful formulation such as needles, and physical difficulty in complying. Therefore, administration of two or even more different dosage forms to the patient may not be convenient or satisfactory to achieve the most optimal results. A pharmaceutical composition comprising an androgenic agent and aromatase inhibitor combined into a single dosage form may provide improved patient compliance.

Where separate dosage formulations are used, the aromatase inhibitor and the androgenic agent can be administered at essentially the same time (e.g., substantially at the same time, concurrently, or simultaneously) or at separately staggered times (e.g., sequentially). The pharmaceutical compositions disclosed herein are understood to include one or more of these regimens. Administration of the pharmaceutical composition by the routes mentioned herein using a suitable regimen may be used as long as the beneficial pharmaceutical effect of the aromatase inhibitor and androgenic agent are realized by the patient. In certain embodiments, the aromatase inhibitor and androgenic agent may be administered concurrently on a once-a-day dosing schedule; however, varying dosing schedules, such as the aromatase inhibitor once per day and the androgenic agent once, twice or more times per day, or the androgenic agent once per day and the aromatase inhibitor once, twice or more times per day, is also encompassed herein. In certain embodiments, a single oral daily dosage formulation may be administered, comprising both the aromatase inhibitor and androgenic agent. A single dosage formulation may provide convenience for the patient.

The appropriate dosing regimen utilizing the androgenic agent, the aromatase inhibitor, or pharmaceutical compositions comprising the androgenic agent and the aromatase inhibitor, the amount of each dose administered, and the intervals between doses of the compounds may depend on various factors such as the particular aromatase inhibitor and androgenic agent being used in combination, the type of pharmaceutical formulation being used, the type of physiological condition being treated, the characteristics of the subject being treated (e.g., species, age, weight, sex, medical condition, fed/fasted), the route of administration, and the severity of the disorder being treated or combinations thereof. A physician or diagnostician of ordinary skill can readily determine and prescribe the effective amount of the androgenic agent, the aromatase inhibitor, or pharmaceutical composition to prevent or to treat the specific physiological condition.

Such pharmaceutical compositions, or individual androgenic agent and/or aromatase inhibitor, may be administered in a single daily dose, or the total daily dosage may be administered in divided doses several times daily. Furthermore, the pharmaceutical compositions, or individual androgenic agent and/or aromatase inhibitor, may be administered as a single dose or over a period of time. Additionally, the pharmaceutical compositions, or individual androgenic agent and/or aromatase inhibitor, may be administered continuously or intermittently. The daily dosage may be varied over a wide range and can be such that the amount of the active compound selected from the androgenic agent and/or aromatase inhibitor is sufficient to cause its desired effects.

The pharmaceutical composition or formulation to be administered may contain a quantity of the compounds or pharmaceutically acceptable salts thereof in an amount effective to treat the condition of the subject being treated. Because two different compounds may be used together in a combination therapy, the potency of each of the compounds and the interactive effects achieved by combining them together typically will also be taken into account. A consideration of these factors is well within the purview of the ordinarily skilled clinician for the purpose of determining the therapeutically effective or prophylactically effective dosage amounts needed to improve side effects.

Administration of the androgenic agent, the aromatase inhibitor, or the pharmaceutical composition comprising a combination of the same, to the subject includes both self-administration and administration to the subject by another person (e.g., physician, nurse, health care worker, friend, etc.).

In certain embodiments, the pharmaceutical compositions may be formulated in a manner compatible with a desired outcome. The pharmaceutical compositions may be administered in a convenient formulation. The following formulation examples only are illustrative and are not intended to limit the scope of the present disclosure.

In certain embodiments, the pharmaceutical compositions may be formulated into tablets, such as those prepared by direct compression, by wet granulation, or by dry granulation. For example, the tablet formulations may incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders. A lubricant may be necessary in a tablet formulation to prevent the tablet and punches from sticking in the die. The lubricant is chosen from such slippery solids as talc, magnesium and calcium stearate, stearic acid and hydrogenated vegetable oils. Tablet disintegrators are substances which swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethylcellulose, for example, may be used, as well as sodium lauryl sulfate. Also, super disintegrants including, but not limited to, Ac-Di-Sol® (sodium croscarmellose cellulose), Explotab® (sodium starch glycolate), VivaStar® (sodium starch glycolate), and Polyplasdone disintegrants may be used.

Tablets are often coated with sugar as a flavor and sealant. The compounds may also be formulated as chewable tablets, by using large amounts of pleasant-tasting substances such as mannitol in the formulation, as is now well-established practice. Instantly dissolving tablet-like formulations are also now frequently used to assure that the patient consumes the dosage form, and to avoid the difficulty in swallowing solid objects that bothers some patients. The size and shape of the tablet may vary according to standard dimensions and shapes known in the art.

In certain embodiments, the pharmaceutical compositions may be formulated into capsules, such as those prepared by mixing the compound with a suitable diluents and filling the proper amount of the mixture in capsules. The usual diluents include inert powdered substances such as starch of many different kinds, powdered cellulose, especially crystalline and microcrystalline cellulose, sugars such as fructose, mannitol and sucrose, grain flours and similar edible powders. The size and shape of the capsule may vary according to standard dimensions and shapes known in the art.

Furthermore, the capsule may be liquid-filled or non-liquid-filled. The capsule may be a hard or soft capsule. Furthermore, it may be a gelatin capsule, a starch capsule, a hydroxypropylmethylcellulose (HPMC) capsule, or a cellulosic capsule. Although not limited to capsules, such dosage forms can further be coated with, for example, a seal coating, an enteric coating, an extended release coating, or a targeted delayed release coating. Additionally, liquid-filled capsules may be emulsions and/or may contain tocopherol as a carrier for poorly soluble compounds such as testosterone.

In certain embodiments, tocopherol may be used as the hydrophobic dispersed phase of an emulsion containing water insoluble, poorly water soluble therapeutic agents, water soluble ones which have been modified to be less water soluble, or mixtures thereof. In a preferred aspect alpha-tocopherol is employed. Alpha-tocopherol is secreted by the enterocytes into the lymphatics and is processed in a similar manner to other forms of vitamin E. Also called vitamin E, alpha-tocopherol is not a typical lipid oil. It has a higher polarity than most lipid oils, particularly triglycerides, and is not saponifiable. It has practically no solubility in water.

In certain embodiments, an alpha-tocopherol emulsion in the form of a self-emulsifying system may be used, where the system is to be used for the oral administration of water-insoluble (or poorly water-soluble or water-soluble agents modified to be less water soluble or mixtures thereof) drugs where that is desired. In such embodiments, an oil phase with surfactant and drug or drug mixture is encapsulated into a soft or hard gelatin capsule. Suitable solidification agents with melting points in the range of 40 to 60° C., such as high molecular weight polyethylene glycols (MW>1000), and glycerides, such as those available under the trade name Gelucire (Gattefose Corp., Saint Priest, France), can be added to allow filling of the formulation into a hard gelatin capsule at a high temperature. Semi-solid formulations are formed upon room temperature equilibration. Upon dissolution of the gelatin in the stomach and duodenum, the oil is released and forms a fine emulsion with a mean droplet diameter of between about 1 to about 15 microns, between about 2 to about 10 microns, or between about 2 to about 5 microns spontaneously. The emulsion is then taken up by the microvilli of the intestine and released into the bloodstream.

In certain embodiments, micro-emulsions containing tocopherol, preferably alpha-tocopherol, may be used. Micro-emulsions refer to a sub-class of emulsions where the emulsion suspension is essentially clear and indefinitely stable by virtue of the extremely small size of the oil/drug micro-aggregates dispersed therein.

In certain embodiments. PEGylated vitamin E (alpha-tocopheryl polyethylene glycol succinate, abbreviated TPGS) may be used as a primary surfactant in emulsions of vitamin E. TPGS is utilized as a primary surfactant, a stabilizer and also as a supplementary solvent in emulsions of vitamin E. TPGS is a water-soluble derivative of d-alpha-tocopheryl succinate. It is also used as an absorption and bioavailability enhancer for certain water-insoluble drugs (e.g. the HIV protease inhibitor amprenavir) and fat-soluble vitamins such as vitamin D. TPGS, because of its amphipathic nature (has both hydrophilic and lipophilic ends), forms its own micelles and thus does not require bile salts to do so. This makes it an excellent alpha-tocopherol substance for those who have problems secreting bile salts into the intestine (e.g., those with chronic childhood cholestasis).

TPGS may enhance the absorption of lipophilic drugs if formulated together with them. For this reason, the HIV protease inhibitor amprenavir is formulated with TPGS. Further, the enhancement of the oral bioavailability of some drugs when co-administered with TPGS may, in part, be due to inhibition of P-glycoprotein in the intestine. P-glycoprotein is the multidrug resistance transporter and is involved in the mediation of multidrug resistance.

In addition, polyethylene glycol (PEG) is also useful as a co-solvent in the emulsions disclosed herein. Of particular use is polyethylene glycol 200, 300, 400 or mixtures thereof.

The alpha-tocopherol concentration of the emulsions may be between about 1 to about 10% w/v, between about 2 to about 5% w/v, or between about 3 to about 4% w/v. The ratio of alpha-tocopherol to TPGS is optimally between about 1:1 to about 10:1 (w/w), between about 1:1 to about 5:1 (w/w), or between about 1:1 to about 15:1 (w/w).

The emulsions disclosed herein may further include surfactants such as ascorbyl-6 palmitate, stearylamine. PEGylated phospholipids, sucrose fatty acid esters and various vitamin E derivatives comprising Q-tocopherol nicotinate, tocopherol phosphate, and nonionic, synthetic surfactant mixtures, such as polyoxypropylene-polyoxyethylene glycol nonionic block copolymer.

The emulsions disclosed herein may comprise an aqueous medium. The aqueous phase generally has an osmolality of approximately 300 mOsm and may include sodium chloride, sorbitol, mannitol, polyethylene glycol, propylene glycol albumin, polypep and mixtures thereof. Osmolality may also range between about 100 to about 500 mOsm and between about 200 to about 400 mOsm. This medium can also contain various additives to assist in stabilizing the emulsion or in rendering the formulation biocompatible. Acceptable additives include acidifying agents, alkalizing agents, anti-microbial preservatives, antioxidants, buffering agents, chelating agents, suspending and/or viscosity-increasing agents, and tonicity agents. Preferably, agents to control the pH, tonicity, and increase viscosity are included. Optimally, a tonicity of at least 250 mOsm is achieved with an agent which also increases viscosity, such as sorbitol or sucrose. Tonicity may also be of at least 300 mOsm, at least 400 mOsm, or at least 500 mOsm.

The emulsions disclosed herein for intravenous injection have a particle size (mean droplet diameter) of about 10 to about 500 nm, preferably about 10 to about 200 nm and most preferably about 10 to about 100 nm. For intravenous emulsions, the spleen and liver typically will eliminate particles greater than 500 nm in size through the RES.

Also testosterone within a liquid-capsule emulsion system may be used.

Aqueous suspensions and/or elixirs are prepared by combining the active ingredient with various sweetening or flavoring agents, coloring matter or dyes, and, if so desired, emulsifying and/or suspending agents as well, together with such diluents as water, ethanol, propylene glycol, glycerin and various like combinations thereof. The amount of suspension may vary according to standard volumes known in the art.

Enteric formulations are often used to protect an active ingredient from the strongly acid contents of the stomach. Such formulations are created by coating a solid dosage form with a film of a polymer which is insoluble in acid environments, and soluble in basic environments. Exemplary films are cellulose acetate phthalate, polyvinyl acetate phthalate, hydroxypropyl methylcellulose phthalate and hydroxypropyl methylcellulose acetate succinate. For example, to formulate duloxetine and duloxetine-containing combinations as enteric compositions. Another example is to formulate them as enteric pellets. The size and shape of such formulations may vary according to standard dimensions and shapes known in the art.

Transdermal patches may also be used. Transdermal administration significantly enhances patient compliance by alleviating the discomfort of needles and other dosage forms by providing a convenient dosage form for once or twice weekly application. Such administration also provides the benefit of having sustained blood levels of the drug being adminstered. Typically patches comprise a resinous composition in which the drugs will dissolve, or partially dissolve, which is held in contact with the skin by a film which protects the composition. Other, more complicated patch compositions are also in use, particularly those having a membrane pierced with innumerable pores through which the drugs are pumped by osmotic action. The size of the patch may vary according to sizes known in the art.

When it is desired to administer the combination as a suppository, the usual bases may be used. Cocoa butter is a traditional suppository base, which may be modified by addition of waxes to raise its melting point slightly. Water-miscible suppository bases comprising, particularly, polyethylene glycols of various molecular weights are also in wide use.

For parenteral, intradermal, intramuscular, or subcutaneous administration, the pharmaceutical compositions may include one of the following, or any combination thereof: sterile diluents, such as water, saline solutions, fixed oils, polyethylene glycols, glycerine, propylene glycol or other synthetic solvents; surfactants such as polysorbate 80, sodium lauryl sulfate, sorbitan monopalmitate; alcohols; suspending agent such as agar, bentonite, microcrystalline cellulose, sodium carboxymethylcellulose, hydroxypropyl methylcellulose, tragacanth, veegum; antibacterial agents such as benzyl alcohol or methyl parabens; antioxidants such as ascorbic acid or sodium bisulfite; chelating agents such as ethylenediaminetetraacetic acid; and buffers such as acetates, citrates or phosphates and agents for the adjustment of tonicity such as sodium chloride or dextrose.

In certain embodiments, the pharmaceutical compositions administered may also include carriers to protect the composition against rapid degradation or elimination from the body, such as a controlled release or sustained release or extended release formulation, including implants and microencapsulated delivery systems. For example, a time delay material such as glyceryl monostearate or glyceryl stearate alone, or in combination with a wax, may be employed. Also, pharmaceutical compositions can include excipients that modify gut metabolism.

Additional methods of preparing various pharmaceutical compositions with a certain amount of each active ingredient are known, or will be apparent in light of this disclosure, to those skilled in this art.

In certain embodiments, the methods may also include administering to the patient the androgenic agent, the aromatase inhibitor, or pharmaceutical composition comprising a combination of the same, in the form of an article of manufacture, such as a kit, which includes the active ingredients disclosed herein, or the active ingredients in suitable pharmaceutical compositions, packaged for distribution. Kits may additionally include instructions for using the kit components in one or more of the disclosed methods. Instructions may include instructions for practicing one or more of the disclosed methods. Thus, for example, a kit can include an androgenic agent or an aromatase inhibitor in a pharmaceutical formulation in a container, pack, or dispenser together with instructions for administration to a human subject. Instructions may additionally include indications of a satisfactory clinical endpoint or any adverse symptoms that may occur, or any additional information required by the Food and Drug Administration for use in humans.

The instructions may be on "printed matter," e.g., on paper or cardboard within the kit, or on a label affixed to the kit or packaging material, or attached to a vial or tube containing a component of the kit. Instructions may additionally be included on a computer readable medium, such as a disk (floppy diskette or hard disk), optical CD such as CD- or DVD-ROM/RAM, magnetic tape, electrical storage media such as RAM and ROM, and hybrids of these such as magnetic/optical storage media.

Kits can additionally include a buffering agent, a preservative, or a stabilizing agent. Each component of the kit can be enclosed within an individual container and all of the various containers can be within a single package.

Since certain embodiments, relate to providing a combination of the two active ingredients which may be administered separately, the present disclosure also relates to combining separate pharmaceutical compositions in kit form. The kit includes two separate pharmaceutical compositions: an androgenic agent and an aromatase inhibitor. The kit includes a container for containing the separate compositions such as a divided bottle or a divided foil packet, however, the separate compositions may also be contained within a single, undivided container. Typically the kit includes directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of a kit is a so-called blister pack. Blister packs are well known in the packaging industry and are being widely used for the packaging of pharmaceutical unit dosage forms (e.g., tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on a card insert, e.g., in the form of numbers next to the tablets or capsules whereby the numbers correspond with the days of the regimen which the tablets or capsules so specified should be administered. Another example of such a memory aid is a calendar printed on the card. Other variations of memory aids will be readily apparent.

Packaging may be accomplished by a number of means utilized in the pharmaceutical industry. Examples of such packaging are: unit dose containers for dispensing liquid compositions enclosed in a box or container along with package inserts; plastic and/or foil wrappers holding solid ocular inserts which contain the active ingredients of the invention and which are enclosed in a box or container along with package inserts. Other modes of packaging would be readily apparent to one skilled in the pharmaceutical packaging arts.

While the present disclosure has been described in terms of certain exemplary embodiments in order to facilitate better understanding of the present disclosure, it should be appreciated that various modifications can be made without departing from the principles of the disclosed herein. Therefore, the inventions should be understood to include such modifications within its scope.

EXAMPLES

Example 1: Dosing Algorithm

Figure 1:
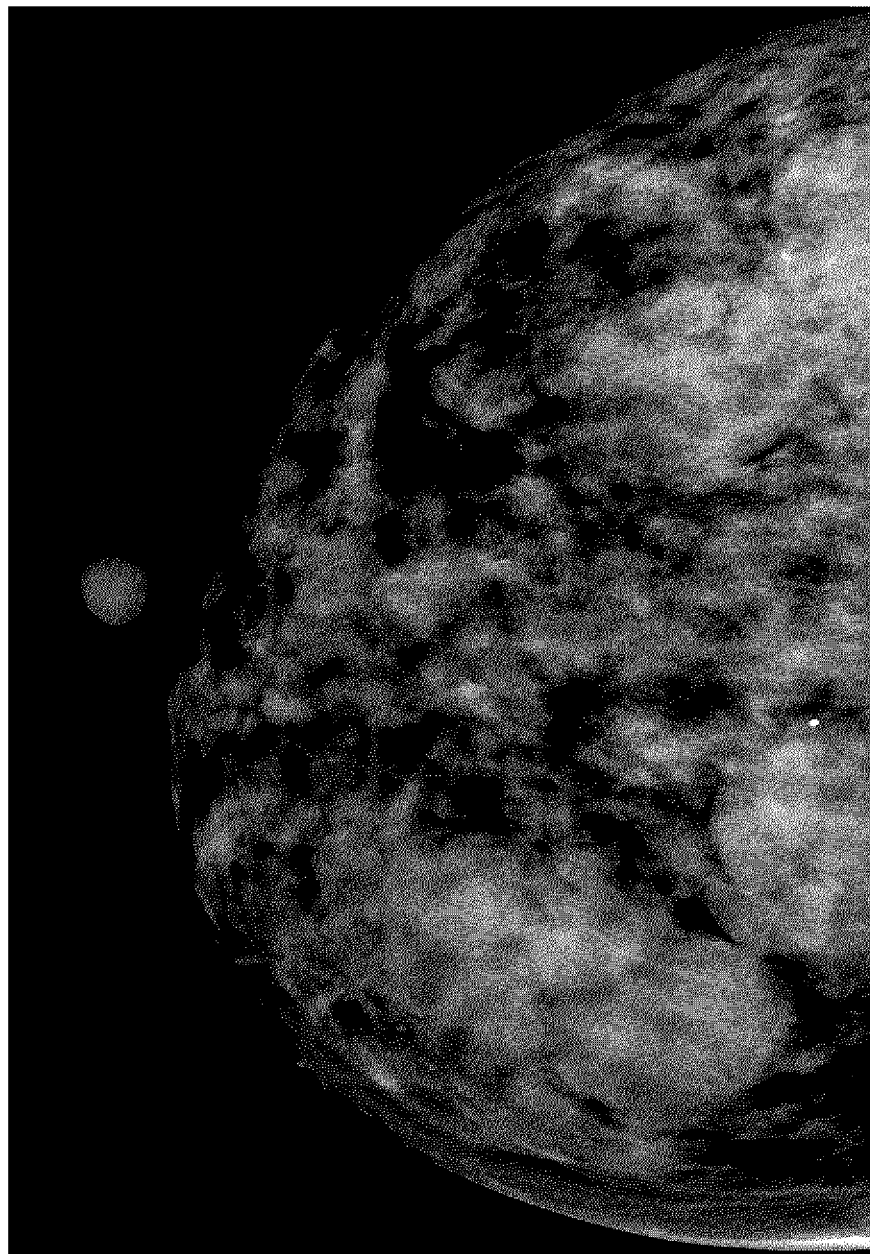
FIG. 1 is a mammogram of a patient's breast immediately before treatment (i.e., at presentation).
Figure 2:
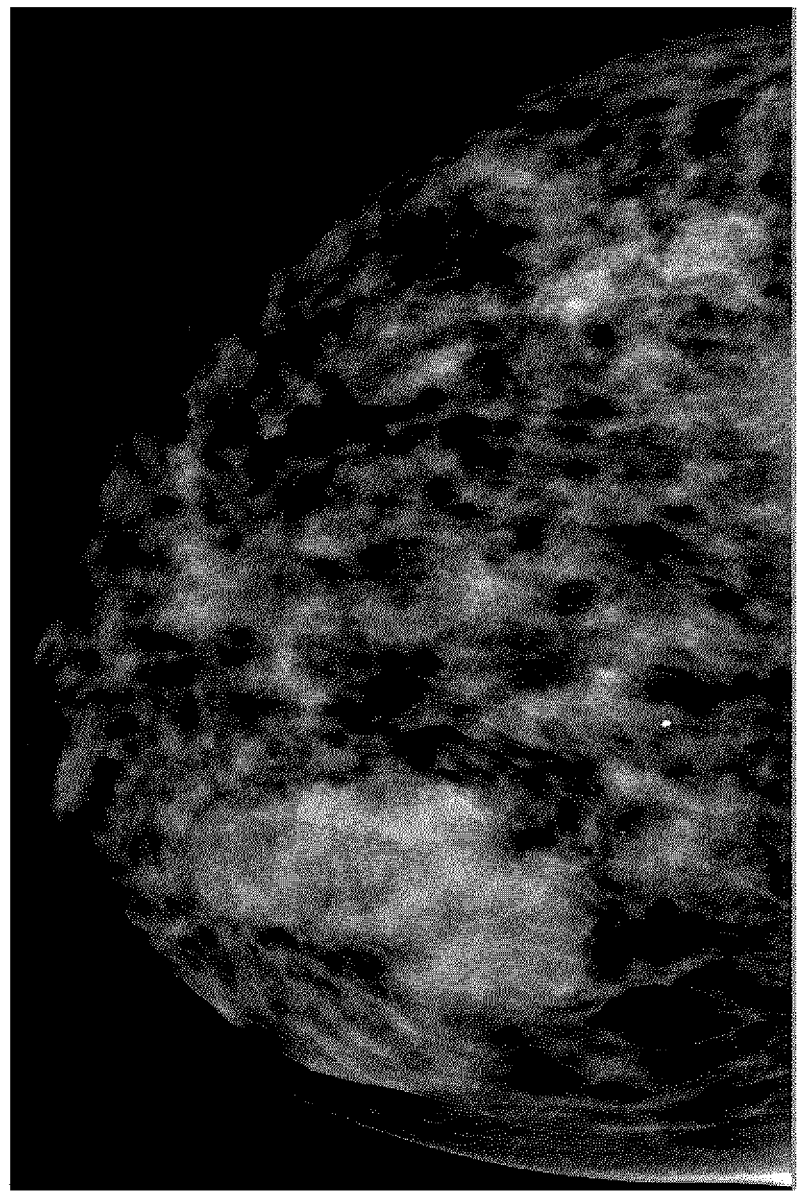
FIG. 2 is a mammogram of the patient's breast at 1 year, i.e., after 1 year of treatment), according to certain embodiments.

A 50 year old woman with high mammographic breast density was treated with a subcutaneous pellet containing the combination of a testosterone and anastrozole for menopausal symptoms including painful breast cysts using the following dosing algorithm. After 1 year of treatment, an improvement in MBD was observed by mammography (FIG. 1 was the mammogram of the patient's breast immediately before treatment, and FIG. 2 was the mammogram of the patient's breast at 1 year, i.e., after 1 year of treatment).

FAI is calculated from a formula where the serum measurement of total testosterone and sex hormone binding globulin are calculated by radio immunoassay. Aromatase inhibitor serum level is determined by liquid chromatography-tandem mass spectrometry.

Dose Schedule
Initial Dosing
Initial dosing (androgenic agent): TD=BW×TBF×MBD+(100−AGE)

Testosterone 59 mg=75×0.4×0.3+50

Initial dosing (aromatase inhibitor): AD=1/BW×1/TBF×MBD+(100/AGE)

anastrozole 2.75 mg=1/75×1/0.4×0.3+100/50

Pellet 1: FAI 15.5% 1 month
FAI 2.5% 3 months
Serum anastrozole 1 month 38 mg/ml
Serum anastrozole 3 month 28 mg/ml
Second Dosing at 4 months Testosterone 71 mg=(75×0.4×0.3+50)+((13−10)×4)

anastrozole 2.75 mg=1/75×1/0.4×0.3+100/50+((10−10)×4)

Pellet 2 FAI 16.5% 1 month
FAI 6.5% 3 months
Scrum anastrozole 1 month 35 mg/ml
Serum anastrozole 3 month 25 mg/ml
Third Dosing at 8 months Testosterone 71 mg=(75×0.4×0.3+50)+((10−10)×4)

anastrozole 2.75 mg=1/75×1/0.4×0.3+100/50+((10−10)×4)

Pellet 3 FAI 16.5% 1 month
FAI 6.5% 3 months
Serum anastrozole 1 month 38 mg/ml
Serum anastrozole 3 month 28 mg/ml
Fourth Dosing at 12 months with a 15% reduction in MBD (see below) and:

Baseline AI=(H+A+VD+SHL)/4(21+0+0+0)=5.2

1 Year AI=(H+A+VD+SHL)/4(20+0+0+0)=5

Therefore as the AI has not increased above 10% and the 15% reduction is well above the target of 2% no dosage alteration is required.

Testosterone 54.5 mg=(75×0.4×0.15+50)+((10−10)×4)

anastrozole 2.05 mg=1/75×1/0.4×0.15+100/50+((10−10)×4)

Example 2: Serum Anastrozole

Thirty women with high MDB have been treated over the past 18 months with 20 having had 2 mammograms for evaluations at baseline and 1 year (Table 1). Table 1 presents the median. All thirty having serum drawn at baseline and at 1 year for serum testosterone and sex hormone binding globulin so that free-androgen index could be calculated (FAI=the ratio of the total testosterone level divided by the sex hormone binding globulin level, and then multiplied by a 100 to give a percentage). Serum anastrazole was calculated by liquid chromatography-tandem mass spectrometry.

TABLE 1

|  | Baseline median (range) | One year median (range) |
| --- | --- | --- |
| Age (30 patients) | 48 (41-56) |  |
| MBD (%) (20 patients) | 35 (20-45) | 25 (13-32) |
|  | $1^{st}$ 3 month trough | End 1st year 3 month trough |
| FAI (%) (30 patients) | 4.8 (2-4.9) | 5.9 (2.1-6.5) |
| Serum anastrazole (ng/ml) (30 patients) | 27 (22-39) | 32 (22-39) |

This example illustrates that the combination of testosterone and Anastrozole given by subcutaneous administration at 4 months intervals resulted in an elevation of serum anastrozole in the therapeutic range and a trough level of testosterone (as measured by FAI) in the high physiological range (normal range typically 0.2-7%). In the 20 women in which mammography was performed there was a significant reduction in MBD as measured by two-tailed student t-test $p<0.001$.

Example 3: Evaluation of Breast Stiffness Reduction Using Mammography

Techniques have been developed which allow an estimate of breast tissue stiffness from the variables derived from mammography. For example the methodology set for in Boyd and in this disclosure. FIG. 3 shows how breast tissue stiffness was estimated from the measures of volume and area described above by making three assumptions. First the technique assumes that the measured breast volumes and the projected area of the compressed breast are substantially accurate measures of these entities. Also assumed is that the shape of the uncompressed breast could be represented by a hemisphere and that of the mammographic area by a semicircle. The measured volume of the breast remains substantially unchanged despite the shape it is assumed to occupy. The assumption that the shape of the uncompressed breast is a hemisphere allows one to calculate the radius of the hemisphere to compare with the radius of the compressed breast obtained from the mammogram. In the absence of compression the projected area of the breast in a mammogram is treated as about equal or substantially equal to the area of a section of the hemisphere and to have a similar or substantially the same radius.

The difference between the radius of the mammographic area semicircle and the radius of the volumetric hemisphere may be defined as deformation. With the compression force recorded with the mammogram the measure of deformation was used to calculate stiffness by the formula: Force/Deformation (N/cm), where N denotes deca-Newtons and cm centimetres.

In example 3, 8 peri-menopausal women have been evaluated for breast stiffness as well as its correlation to breast pain reduction. The 8 peri-menopausal women were treated with testosterone 80 mg and anastrazole 2 mg combined in a subcutaneous pellet and inserted into either the lower abdominal wall or the upper gluteal region and received insertions of the pellet at 0 months (baseline), 4 and 8 months with the repeat measurements taken at 1 year when visual analogue pain scale was undertaken as well as mammography for assessment of both VBD % and breast stiffness.

A 100 mm Visual Analogue Scale assessed breast pain at baseline and 1 year follow-up mammogram (Table 2 median and Table 3 mean). The formulas discussed in Example 1 were utilized to assess breast stiffness using the Boyd methodology and as set forth in this disclosure.

TABLE 2

|  | Baseline median (range) | One year median (range) |
| --- | --- | --- |
| Age | 44 (41-47) |  |
| MBD (%) | 36 (29-44) | 21 (13-30) |
| VAS breast pain (mm) | 75 (60-100) | 30 (0-50) |
| Breast Stiffness (N/cm) | 45 (38-48) | 25 (18-31) |

TABLE 3

|  | Baseline mean (SD) | One year mean (SD) |
| --- | --- | --- |
| Age | 44 years (1.7) |  |
| MBD (%) | 32 (12.8) | 20 (4.9) |
| VAS breast pain (mm) | 76 (13.1) | 29 (14.7) |
| Breast Stiffness (N/cm) | 44 (3.8) | 24 (3.9) |

The (MBD (%), VAS breast pain, and breast stiffness measured before and after have a significance of p<0.0001 on student two-tailed t-test. This example illustrates that the 8 peri-menopausal woman treated had a significant reduction in MBD % both in the median and the mean of the group tested. This example also shows a significant reduction in Breast Stiffness in the woman treated. Also a significant reduction in VAS breast pain was observed.

Example 4A Prophetic MBD %

A patient having a mammographic breast density of at least 7.5%, is given an initial dose of both an androgenic agent and an aromatase inhibitor in a subcutaneous pellet, wherein the initial doses are determined by the treating physician according to standard doses for each specific agent. The subsequent doses of the androgenic agent and aromatase inhibitor in subcutaneous pellets, each measured in mg, are provided every 3 months to the patient and are determined as a function of the following formulas:

$$AD = F1(N, T, BW, TBF\ MBD, BS, AGE, FAI(T), AI(T), TD) \quad \text{Formula 1}$$

$$TD = F2(N, T, BW, TBF, MBD, BS, AGE, SAL(T), AI(T)) \quad \text{Formula 2}$$

wherein:
N is the dose number (N=1 being the first dose);
T is time in months from the first dose;
BW is body weight measured in kg;
TBF is fraction of BW measured by bio-impedance;
MBD is mammographic breast density, being the percentage of breast fibro-glandular tissue relative to total breast volume where the MBD is the average of both breasts, e.g., measured by Volpara breast density software;
Age=years;
AI(T) is the Androgenicity Index as a function of time which is given by:

$$AI(T) = F3(H, A, VD, SHL) \quad \text{Formula 3}$$

wherein each of the parameters is measured at time T and
H is a measure of Hirutism;
A is a measure of Acne;
VD is measure of Voice Deepening;
SHL is a measure of Scalp Hair Loss;
FAI(T) is the Free Androgen Index measured at time T; In this embodiment, FAI is given by $$FAI(T) = 100 \times TT/SHBG \quad \text{Formula 4}$$

wherein the variables are measured at time T and
TT is the patient's Total Testosterone level and
SHBG is the patient's Sex Hormone Binding Globulin level;
TD is the dose of Androgenic Agent being administered at the same time as the AD dose.
BS is a measure of Breast Stiffness averaged across both breasts; and
SAL(T) is the Serum Aromatase Level measured in ng/ml at time T; and
wherein each parameter is measured just prior to the dose number N, except for FAI(T), AI(T) and SAL(T), which are calculated at specified times T related to the dose number N.

Accordingly, using Formulas 1A and 2A along with the data from Example 1, the following parameters include possible alternative values as determined by the individual patient:

$V1(N) = 1$ for $N = 1, 2, 3$ $V1(4 \times n) = (1 + R(n)) \times V1(4 \times n - 1)$ for $n = 1, 2, 3 \ldots$ $V1(4 \times n + m) = V1(4 \times n)$ for $m = 1, 2, 3$ and $n = 1, 2, 3 \ldots$ where $R(n) = 0$ if $AI(12 \times n) - AI(0) > C6$ $R(n) = 0$ if $MBD(4 \times n - 3) - MBD(4 \times n) > C12$ $R(n) = 0$ if $1 - BS(4 \times n)/BS(2 \times n - 3) > C13$ otherwise $R(n) = C7$.

$V2(1) = 0$ $V2(N) = C10 \times (SAL(4 \times (N-1) - 3) - SAL(4 \times (N-1) - 1) - C11)$ for $N > 1$ $V3(1) = 0$ $V3(N) = C8 \times (FAI(4 \times (N-1) - 3) - FAI(4 \times (N-1) - 1) - C9)$ for $N > 1$ C1 to C12 are constants and in one embodiment are given by:
C1=C2=C4=C5=1
C3=100 years
C6=10%

C7=0.1
C8=4 mg
C9=10
C10=0.1 mg
C11=10 mg/ml
C12=2%
C13=20%.

The above parameters are then optimised to achieve the following optimal outcomes on average:

FAI of 15% at one month after a dose and 5% at 3 months after a dose;

SAL of 35 ng/ml at 1 month after a dose and 25 ng/ml at 3 months after a dose;

A reduction of 2% per annum in the MBD constrained by the AI not increasing more than 10% in that year.

Example 4A Prophetic VBD %

A patient having a mammographic breast density of at least 7.5%, is given an initial dose of both an androgenic agent and an aromatase inhibitor in a subcutaneous pellet, wherein the initial doses are determined by the treating physician according to standard doses for each specific agent. The subsequent doses of the androgenic agent and aromatase inhibitor in subcutaneous pellets, each measured in mg, are provided every 3 months to the patient and are determined as a function of the formulas in Example 4A, however instead of MBD being used VBD % is used in the calculations.

Figure 6:
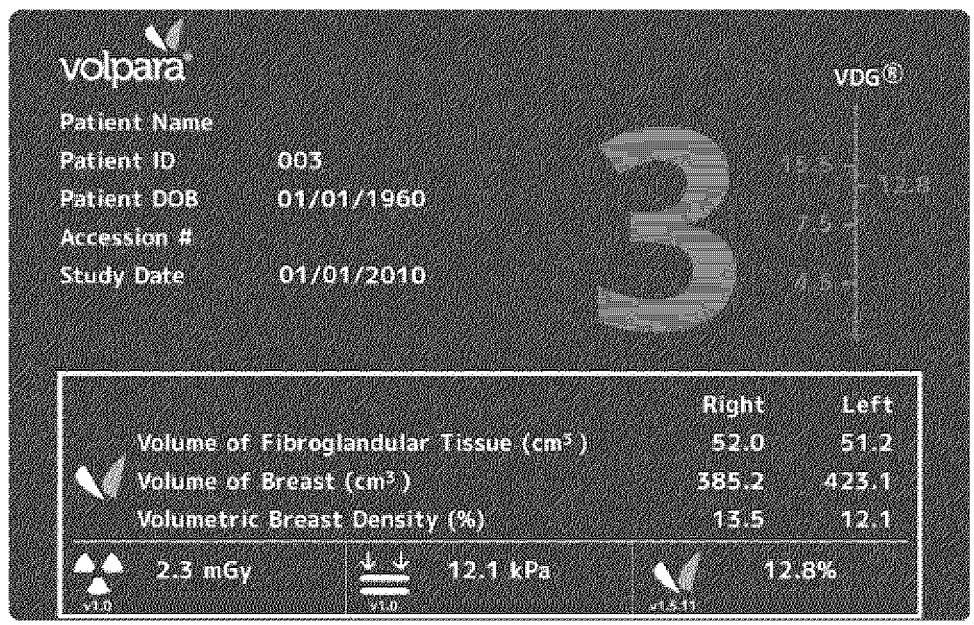
FIG. 6 is an exemplary Volpara Solution™ information panel generated from a mammogram.

Example 5: A Cohort Study Undertaken to Examine the Impact of an Androgenic Agent and an Aromatase Inhibitor in the Reduction of the ABVD and/or a Reduction in VBD % in Peri-Menopausal Women 74 peri-menopausal women were selected from the annual mammographic screening program at the Burnside hospital breast center. These women were having annual breast screening for an increased risk of developing breast cancer secondary to either a family history of breast cancer or high VBD %. These women acted as controls for 74 women undergoing androgen and aromatase inhibitor therapy for either peri-menopausal symptoms and/or for treatment of high VBD %. The dosing varied as per the variables listed in the dosing algorithm disclosed herein. Patients received between 50-120 mg of testosterone and 1-3 mg of anastrozole compounded into a pellet inserted every 4 months into the subcutaneous fat of the lower abdominal wall or upper gluteal region. The VBD % was calculated using the software algorithm generated by Volpara Solution™. This program may be used to generate the exemplary information panel shown in FIG. 6 for a mammogram.

Inclusion criteria for either group 1) not pregnant;
2) high VBD % of greater than or equal to 15.5 percent as calculated by Volpara Solution™ breast density software;
3) No exogenous hormonal usage in the three months prior to enrollment; and
4) no significant comorbidities.

The age statistics for the cohort are set out below in Table 4. The AVBD statistics for the cohort are set out below in Table 5.

TABLE 4

| Age Statistics | | |
|---|---|---|
| | Treatment Group | Control Group |
| Number | 74 | 74 |
| Mean age (years) | 48.8 | 49.2 |
| Standard deviation of age | 6.1 | 6.2 |
| Median age | 48 | 49 |
| Minimum age | 39 | 39 |
| Maximam age | 60 | 60 |

TABLE 5

| | AVBD statistics | | | |
|---|---|---|---|---|
| | Treatment Group | | Control Group | |
| | Pre-treatment | One Year | Baseline | One Year |
| Mean of absolute volumetric breast density (AVBD) - average both breasts (cubic cm) | 101.4 | 85.2 | 100.7 | 104.0 |
| Standard deviation | 56.8 | 43.8 | 49.4 | 49.5 |
| Mean percentage change in the average of both breasts of the AVBD | | −14.7% | | −3.0% |
| Standard deviation | | 11.0% | | 5.3% |
| 99% confidence interval in mean | | +3.4% | | +1.6% |
| Median change | | −11.9% | | −2.6% |
| Minimum change | | −50.5% | | −24.4% |
| Maximum change | | −0.1% | | +11.4% |

Figure 7:
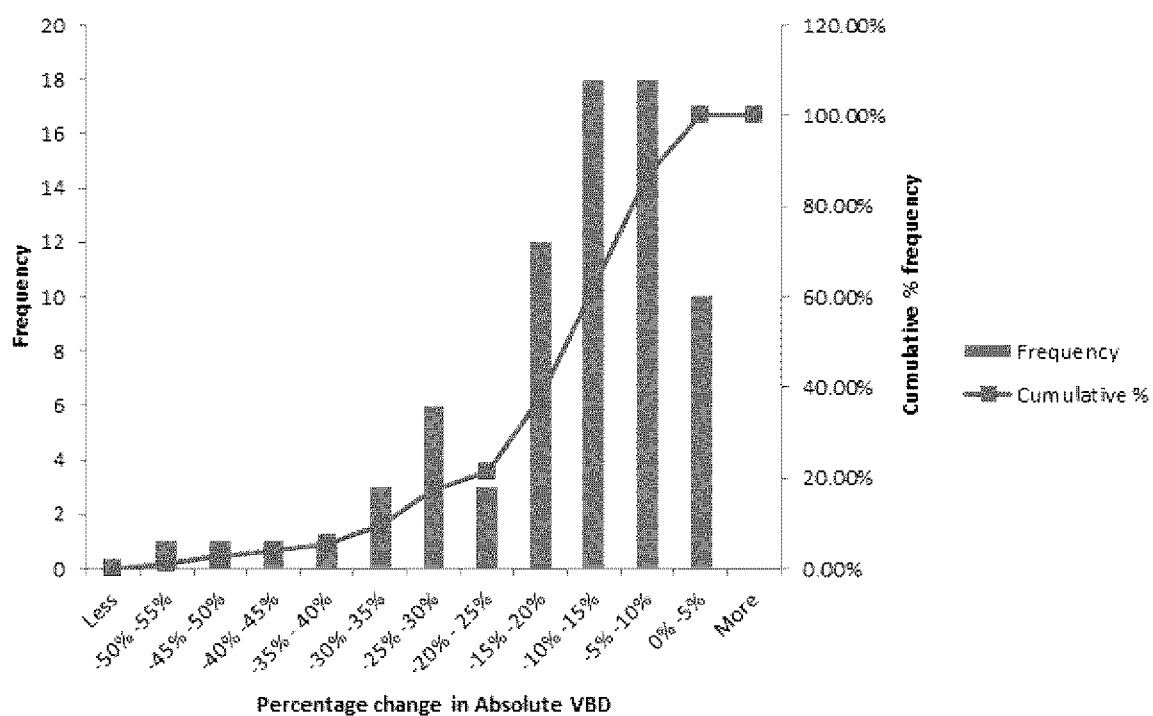
FIG. 7 is a histogram of the percent change in AVBD for the treated patients, according to an exemplary embodiment.
Figure 8:
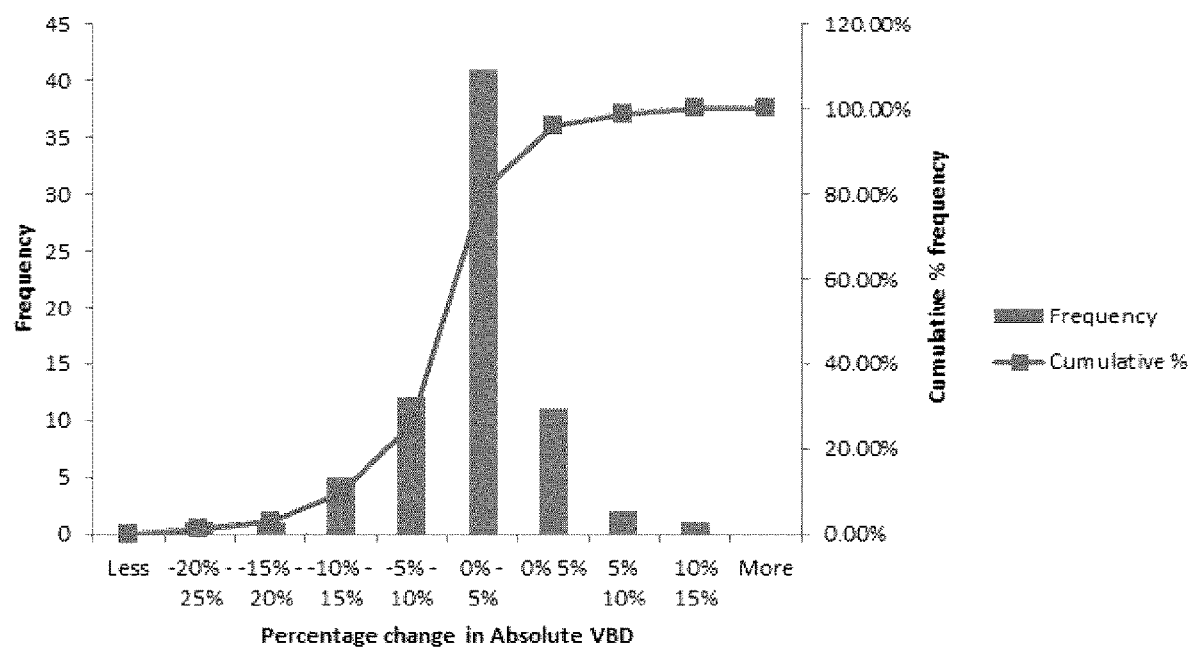
FIG. 8 is a histogram of the percent change in AVBD for the control patients, according to an exemplary embodiment.

FIG. 7 provided a histogram of the percent change in AVBD for the treated patients. FIG. 8 provided a histogram of the percent change in AVBD for the control patients.

FIG. 9 provides a chart that plots for each patient treated with androgen agent and aromatase inhibitor a point having an x-coordinate equal to the pre-treatment average AVBD incubic centimeters and the y-coordinate being the post-treatment AVBD. Also plotted is the through-the-origin linear regression line which has the formula Post-treatment=0.8115×Pre-treatment AVBD. The r-squared of the regression is 0.969 and the 99% confidence interval on the slope is 0.767 to 0.856. Also plotted is the line y-coordinate=x-coordinate which bounds the area above, where post-treatment AVBD is greater than pre-treatment AVBD, from the area below, where post-treatment AVBD is less than pre-treatment AVBD. All points fall below the line in this FIG. 9.

FIG. 10 provides a chart that plots for each control group (untreated) patients a point having an x-coordinate equal to the baseline average AVBD in cubic centimeters and the y-coordinate being the AVBD one year from baseline. Also plotted is the through-the-origin linear regression line which has the formula One year AVBD=0.9722×Baseline AVBD. The r-squared of the regression is 0.997 and the 99% confidence interval on the slope is 0.957 to 0.987. Also plotted is the line y-coordinate=x-coordinate which bounds the area above, where the One year AVBD is greater than the Baseline AVBD, from the area below, where One year AVBD is less than the Baseline AVBD.

Table 6 below provided the VBD % statistics for the cohort. FIG. 11 provides a histogram of the percent change of the mean of the VBD % of the treated patients. FIG. 12 provides a histogram of the percent change of the mean VBD % of the control patients.

VBD % after one year. Also plotted is the through-the-origin linear regression line which has the formula Post-treatment VBD %=0.975×Pre-treatment VBD %. The r-squared of the regression is 0.995 and the 99% confidence interval on the slope is 0.993 to 0.998. Also plotted is the line y-coordinate=x-coordinate which bounds the area above, where post-treatment VBD % is greater than pre-treatment VBD % from the area below, where post-treatment VBD % is less than pre-treatment VBD %. This is a control group therefore no treatment is given.

Discussion

It is recognized that AVBD and/or VBD % reduces around the menopause to a small degree. It has been estimated that over a five-year period menopause women lose between 5 to 10% of AVBD and/or VBD % which then stabilizes following menopause and typically reduces little over the rest of the woman's life.

The control group shows a small reduction in both AVBD (3%) and VBD % (2%) over a 1 year period. The group treated with the androgenic agent and aromatase inhibitor shows a 14.7% reduction in AVBD and a 19.5% reduction in VBD %.

The cohort study set forth in the example has used a combination of an androgenic agent and an aromatase inhibitor in pre-menopausal woman to show a reduction in AVBD and VBD %. This study has also evaluated women with high AVBD and VBD % and pre-menopausal status.

TABLE 6

| | VBD % statistics | | | |
|---|---|---|---|---|
| | Treatment Group | | Control Group | |
| | Pre-treatment | One Year | Baseline | One Year |
| Mean of VBD %(AVBD/volume of breast) (cubic cm) - average both breasts | 24.7% | 19.4% | 25.2% | 24.7% |
| Standard deviation | 5.6% | 7.4% | 5.4% | 5.3% |
| Mean percentage change in the average of both breasts of VBD % | | −19.5% | | −2.0% |
| Standard deviation | | 34.9%* | | 8.3% |
| 99% confidence interval in mean | | ±10.7%* | | ±2.5% |
| Median change | | −20.8% | | −4.0% |
| Minimum change | | −71.7 | | −13.8% |
| Maximum change | | 248.7* | | 26.0 |

*Note:
One patient had a very large decrease in breast volume as a result of treatment which led to an unusually large increase in VBD % as an outlier statistic.

FIG. 13 chart plots for each patient treated with an androgenic agent and an aromatase inhibitor a point having an x-coordinate representing the pre-treatment VBD % and the y-coordinate being the post-treatment VBD %. Also plotted is the through-the-origin linear regression line which has the formula Post-treatment VBD %=0.7657×Pre-treatment VBD %. The r-squared of the regression is 0.873 and the 99% confidence interval on the slope is 0.676 to 0.886. Also plotted is the line y-coordinate=x-coordinate which bounds the area above, where post-treatment VBD % is greater than pre-treatment VBD % from the area below, where post-treatment VBD % is less than pre-treatment VBD %. In this chart the points fall on or below the line except for one patient who had a large increase in VBD % due to a large fall in body weight.

FIG. 14 plots the control group having an x-coordinate equal to the base line VBD % and the y-coordinate being the Not wishing to be bound by a particular theory, however, the present disclosure shows that the use of an aromatase inhibitor in high AVBD and/or VBD % woman is useful because it blocks the aromatase expression which may be higher in high breast density tissue.

Example 6: AVBD and VBD % Reduction

Figure 15B:
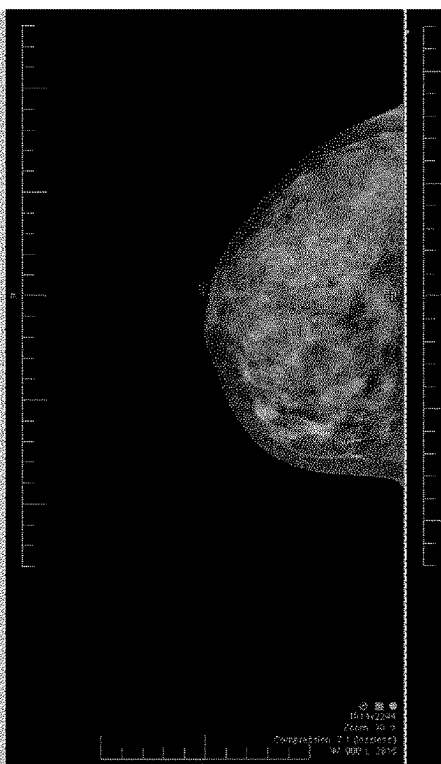
Figure 15C:
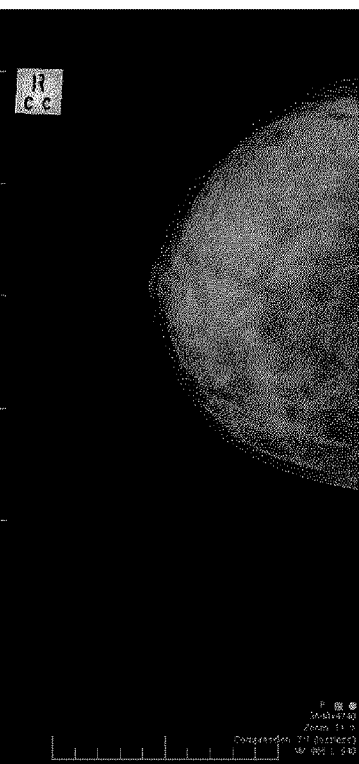

The impact of the AVBD and VBD % reduction is shown in this example of a 44 year old woman with extreme breast density. The reduction in density was associated with a reduction pain, an improved ability to assess breast tissue for lesions and a reduction in pain associated with the compression of the breasts during mammography. FIG. 15C is a mammographic image of the patient's right breast pre-treatment. FIG. 15C illustrates extreme AVBD and VBD %.

Thereafter the patient was treated with a 4.5 mm subcutaneous pellet inserted into the lower abdominal wall. The pellet contained testosterone 80 mg and anastrozole 2 mg. Approximately every four months thereafter the treatment was repeated. FIG. 15B show a mammographic image of the same breast at approximately 12 months after four treatments. As illustrated in FIG. 15B, there has been a substantial reduction in mammographic breast density. The treatment was continued with additional pellets being inserted approximately every four months for another 12 months. FIG. 15A shows a mammographic image of the patient's breast after 24 months of treatment (8 treatments in total). As illustrated in FIG. 15B, there has been a progressive and a further reduction in mammographic breast density.

This example shows that treatment with an androgenic agent and an aromatase inhibitor has brought about a substantial and progressive reduction in mammographic breast density. The patient reported significant symptomatic relief from breast pain. These mammograms demonstrate an improvement in the diagnostic sensitivity of the images at both 12 and 24 months with respect to the ability to assess breast tissue for lesions. In addition, the patient reported at both 12 and 24 months a progressive reduction in the pain associated with the compression of the breasts during mammography.

Example 7: Reduction in VBD % and AVBD

FIG. 16A shows the mammographic image of a 45 year woman who was peri-menopausal pre-treatment. As you can see from FIG. 16A, this patient has high VBD % and a high AVBD. This is also supported in the Volpara Solution™ analysis in FIG. 16B. Before treatment a VBD %=27.2% and AVBD=95.6+100.7=196.3 cubic cm. The patient was then treated with testosterone 80 mg and anastrozole 2 mg as a subcutaneous pellet every 4 months for 4 treatments and the repeat mammogram was taken approximately 1 year later.

As shown in FIG. 17A, after approximately 1 year of treatment there was a substantial reduction in VBD % and AVBD. This is also shown in the Volpara Solution™ analysis found in FIG. 17B which shows a VBD %=15.4% and an AVBD=68.7+69.8=138.5. The relative reduction in the VBD % is 43% and the relative reduction in AVBD is 30% for this patient. It can be seen that there is a much-improved image after the treatment, which improves diagnostic sensitivity and reduces false positive interpretation.

Example 8: Reduction in VBD % and AVBD

FIG. 18A shows the mammographic image of a 48 year woman who was peri-menopausal pre-treatment. As you can see from FIG. 18A, this patient has a high VBD % and a high AVBD. This is also supported in the Volpara Solution™ analysis in FIG. 18B. Before treatment a VBD %=19.9% and AVBD=88.1+74.5=162.6 cubic cm. The patient was then treated with testosterone 80 mg and anastrozole 2 mg as a subcutaneous pellet every 4 months for 4 treatments and the repeat mammogram was taken approximately 1 year later.

As shown in FIG. 19A, after approximately 1 year of treatment the image shows substantial reduction in VBD % and AVBD. This is also shown in the Volpara Solution™ analysis found in FIG. 19B which shows a VBD %=15.8% and an AVBD=68.7+69.8=138.5. The relative reduction in the VBD % is 25% and the relative reduction in AVBD is 15% for this patient. It can be seen that there is a much-improved image after the treatment, which improves diagnostic sensitivity and reduces false positive interpretation.

Example 9: Reduction in VBD % and AVBD

FIG. 20A shows the mammographic image of a 49 year woman who was peri-menopausal pre-treatment. As you can see from FIG. 20A, this patient has high VBD % and a high AVBD. This is also supported in the Volpara Solution™ analysis in FIG. 20B. Before treatment a VBD %=20.0% and AVBD=60+84.6=144.6 cubic cm. The patient was then treated with testosterone 80 mg and anastrozole 2 mg as a subcutaneous pellet every 4 months for 4 treatments and the repeat mammogram was taken approximately 1 year later.

As shown in FIG. 21A, after approximately 1 year of treatment there was a substantial reduction in VBD % and AVBD. This is also shown in the Volpara Solution™ analysis found in FIG. 21B which shows a VBD %=14.7% and an AVBD=53.4+72.3=125.7. The relative reduction in the VBD % is 26% and the relative reduction in AVBD is 13% for this patient. It can be seen that there is a much-improved image after the treatment, which improves diagnostic sensitivity and reduces false positive interpretation.

Example 10: Reduction in Pain

Twenty peri-menopausal women were treated for breast pain at the WellendHealth Clinic Burnside Hospital, Toorak Gardens South Australia. The patients were treated with testosterone (50-100 mg) combined with anastrozole (1-3 mg) compounded into a 4.5 mm pellet and inserted into the subcutaneous fat of either the lower anterior abdominal wall or the upper outer gluteal region. The dosage was initially determined based at least in part on weight. The patient received 50 mg (40 kg to 55 kg), 60 mg (55 kg to 65 kg), 80 mg (65 kg to 85 kg) or 100 mg (85 kg to 120 kg) of testosterone. The anastrozole dosage was based on the amount of testosterone given (1 mg anastrolzole:50 mg testosterone; 1 mg: 60 mg; 2 mg:80 mg; and 3 mg:100 mg.). Below in Table 7 is set forth the dose provided to each patient as well as the pain measurement using the visual analog scale (VAS) disclosed herein. Each patient would have received a 4.5 mm pellet and inserted into the subcutaneous fat of either the lower anterior abdominal wall or the upper outer gluteal region at the beginning of treatment and ever 4 months thereafter. The number of doses received was dependent on the number of months that the patient was treated. For example if treated for 12 months the patient would have received 4 doses. Table 7 sets forth the mean pain VAS before therapy and the mean pain VAS after therapy as well as the time on therapy. Visual analogue scale (VAS) was measured on a 100 mm scale where 0=no breast pain and 100=worse breast pain. P=0.00001 2 tailed student t-test for variance of the mean. As shown in Table 7 there is a substantial and significant overall reduction in the measured pain after therapy.

TABLE 7

| Patient | Pre-Treatment Pain (VAS) | Post-treatment Pain (VAS) | Time on treatment (months) | Dose Testosterone mg | Dose Anastrozole |
|---|---|---|---|---|---|
| 1 | 61 | 32 | 12 | 50 | 1 |
| 2 | 60 | 25 | 13 | 60 | 1 |
| 3 | 85 | 30 | 14 | 100 | 3 |
| 4 | 91 | 0 | 15 | 80 | 2 |
| 5 | 75 | 13 | 12 | 60 | 1 |
| 6 | 65 | 45 | 14 | 80 | 2 |
| 7 | 68 | 17 | 11 | 80 | 2 |
| 8 | 91 | 35 | 12 | 80 | 2 |
| 9 | 75 | 32 | 12 | 80 | 2 |
| 10 | 80 | 33 | 12 | 80 | 2 |
| 11 | 81 | 25 | 14 | 50 | 1 |
| 12 | 74 | 33 | 13 | 60 | 1 |
| 13 | 76 | 45 | 15 | 100 | 3 |
| 14 | 100 | 50 | 14 | 80 | 2 |
| 15 | 71 | 30 | 12 | 60 | 1 |
| 16 | 72 | 12 | 12 | 60 | 1 |
| 17 | 84 | 48 | 14 | 50 | 1 |
| 18 | 69 | 18 | 13 | 100 | 3 |
| 19 | 65 | 24 | 15 | 80 | 2 |
| 20 | 64 | 25 | 12 | 80 | 2 |
| Mean | 75.35 (SD 10.8) | 28.6 (SD 12.6) | | | |

Example 11: Impact of an Androgenic Agent and an Aromatase Inhibitor on the Hypothalamic-Pituitary Axis Peri-Menopausal Woman The 74 women involved in the cohort study discussed in example 5 had blood drawn pre-treatment and at three months after their first treatment with an androgenic agent and an aromatase inhibitor as set forth in example 5 (testosterone and anastrozole pellet). Radio immunoassays were undertaken to determine serum follicular stimulating hormone (FSH) and luteinizing hormone (LH).

TABLE 8

| | FSH U/L (mean (SD)) | LH U/L (mean (SD)) |
|---|---|---|
| Pre-treatment | 12 (6) | 48 (28) |
| Post-treatment | 13 (6) | 50 (29) |
| 2-tailed t-test | p = 0.33 | P = 0.79 |

No significant impact of testosterone and an aromatase inhibitor was demonstrated on hypothalamic-pituitary function as demonstrated by serum FSH and LH.

The use of aromatase inhibitors in women before the menopause has been thought to be contraindicated because of the potential effect on hypothalamic-pituitary function. There have been a few studies which have demonstrated the efficacy of aromatase inhibitors in the management of diseases such as endometriosis and uterine excessive proliferation such as fibroids. The present example demonstrates in the cohort of 74 pre-menopausal women that there has been negligible impact on pituitary function as demonstrated by the lack of alteration in follicular stimulating hormone and luteinizing hormone. The examples demonstrates that a combination of an androgenic agent and an aromatase inhibitor may be given to pre-menopausal women without impacting on hypothalamic-pituitary function, therefore facilitating the blockade of aromatase action in breast tissue without significant measurable endocrine disruption.

Example 12: Measurement of Breast Elasticity and the Ratio of the Fibro-Glandular and Adipose Tissue Before and After Treatments Four peri-menopausal women received one treatment with testosterone 80 mg and anastrozole 2 mg combined in a subcutaneous pellet and inserted into the lower abdomen or upper gluteal region. These four women received a bilateral 4 quadrant ultrasound (US) for shear wave elastography (SWE), both before treatment and 3 months after the subcutaneous pellet was inserted. SWE is a measurement of breast stiffness. Physical forces generated by interactions between cells, and between cells and the extracellular matrix may be associated with an increase in tissue stiffness. Breast stiffness is associated with an increased risk of developing breast cancer. High mammographic density and/or breast stiffness are associated with an increased number of cells and/or extra-cellular matrix, these factors increase breast tissue stiffness. Ultrasonic elastography may be used to measure breast stiffness. Accordingly, reducing breast stiffness is believed to reduce the risk of developing breast cancer.

Ultrasound examinations and ultrasound images were obtained using the Aixplorer system (SuperSonic Imagine, Aix en Provence, France) equipped with a 15 MHz linear-array transducer. Customized presets of shear wave elastography parameters as per those provided by the manufacturer were used representing the elastic modulus in kilopascals (kPa) at each pixel. Quantitative elasticity values were measured using a 2-mm-sized circular quantification region of interest (Q-box™) placed at SWE images that were acquired 2 cm from the edge of the nipple areolar in each 4 quadrants. Table 9 below sets forth the change in SWE measurements after three months of treatment with 80 mg of testosterone and 2 mg of anastrazole.

TABLE 9

| Patient number | Pre-treatment (kPa) Fibro-glandular tissue | Post-treatment (kPa) Fibro-glandular tissue |
|---|---|---|
| 1 | 107.0 | 67.3 |
| 2 | 144.3 | 80.4 |
| 3 | 127.6 | 98.3 |
| 4 | 116.3 | 80.0 |
| Mean | 123.8 | 81.5 |
| SD | 16.05 | 12.75 |

The combined elastography of both breasts as a consequence of scanning all 4 quadrants of the breast measured in kPa. P=0.003 2-tailed student t-test This example demonstrates a reduction in the elastic modulus as measured by the ultrasounds after three months of treatment and an associated reduction in breast stiffness as measured by ultrasound elastography.

The breast is made up of two major components: adipose (or fat) and fibro-glandular tissue. The medial part of the breast has the least amount of fibro-glandular tissue compared to adipose. The breast next to the sternum (breast bone) has more adipose than fibro-glandular tissue and is a site that may be identified by its juxtaposition to the $4^{th}$ intercostal space. Adipose in this region was identified by ultrasound and breast elastography was undertaken in the 4 women above utilizing the technique described above and the following data was obtained (Table 10).

TABLE 10

| Patient number | Pre-treatment (kPa) of Adipose tissue | Post-treatment (kPa) of Adipose tissue | Ratio of fibro-glandualar to adipose - Pre-treatment | Ratio of fibro-glandualar to adipose - Post-treatment |
|---|---|---|---|---|
| 1 | 87.2 | 45.8 | 1.23 | 1.47 |
| 2 | 121.5 | 71.2 | 1.19 | 1.13 |
| 3 | 84.3 | 35.9 | 1.51 | 2.74 |
| 4 | 72.1 | 22.7 | 1.61 | 3.52 |
| Mean | 92.6 | 43.3 | 1.44 | 2.46 |
| SD | 25.7 | 25.0 | 0.22 | 1.22 |

There was a significant reduction in breast adipose stiffness in the 4 treated women with p=0.03 two-tailed student T-test. In addition, alteration in ratio of breast stiffness was observed between the fibro-glandular and adipose tissue before and after treatments. In other words, a more marked reduction in stiffness in the breast adipose tissue versus the fibro-glandular tissue was observed. The mean ratio being 1.44 before and 2.4 after.

Example 13: Effects on the Expression of CD36 in Normal Female Breast Explants Normal breast tissue was excised from 3 peri-menopausal women taken during surgery for other breast conditions. The tissue samples were transported to the laboratory on ice, with a maximum time of one hour between excision and tissue processing. The breast tissue samples were washed in media (phenol red-free RPMI; SAFC biosciences, Kansas, USA), supplemented with 5 ml of 200 mM glutamine (SAFC biosciences, Kansas, USA), 5 ml of 10 µg/ml antibiotic/anti-mycotic (Sigma, St Louis, Mo., USA), 10 µg/ml insulin (Sigma, St Louis, Mo., USA), and 10 µg/ml hydrocortisone (Sigma, St Louis, Mo., USA) to remove excess blood.

A representative piece of each tissue sample was immediately fixed in 4% formalin in phosphate-buffered saline (PBS) overnight at 4° C., followed by dehydration using an automatic tissue processor (Sakura Tissue-Tek VIP, USA) and paraffin wax embedding. A haematoxylin and eosin (H&E) stained section was used to assess tissue pathology. The remaining fresh tissue was cut into small (~3×3×1 mm) pieces, and placed as triplicates on 1 $cm^3$ gelatin sponges (Spongostan; Johnson & Johnson, Skipton, UK) that were pre-soaked and then half submerged in treatment media containing 10% dextran-coated charcoal stripped fetal calf serum (DCC-FCS) (SAFC biosciences, Kansas, USA) in 24-well tissue culture plates (BD Biosciences, NJ, USA). The tissues samples were then cultured for 24 hours in a vehicle of 0.1% ethanol, 5 nM of testosterone and 25 mg/ml of anastrazole.

Western blotting whole cell lysates of and control adipose tissue were prepared by sonication at 48 C in lysis buffer (1% Triton X-100, 50 mM KCl, 25 mM HEPES, pH 7.8, 10 mg/ml of leupeptin, 20 mg/ml of aprotinin, 125 mM dithiothreitol and 1 mM phenylmethylsulfonyl fluoride) and analyzed on the same western blot, 50 mg samples of total protein were mixed with 50 ml of sodium dodecyl sulfate (SDS)-mercaptoethanol sample buffer and boiled for 10 min, then the proteins were separated on 7.5% SDS gels and transferred to a polyvinylidene fluoride membrane. The membrane was then blocked for 1 h at room temperature using 5% skimmed milk in phosphate-buffered saline (PBS) containing 0.5% Tween-20, immunoblotted with antibodies against human CD36 diluted in PBS and horseradish peroxidase-conjugated secondary antibodies (Jackson Immunoresearch) diluted in PBS, followed by detection with Chemiluminescence Reagent (Amersham Bioscience, Buckinghamshire, England). The band density was measured by densitometry, using Image Master VDS and Image Quant Analysis Software (Amersham Pharmacia Biotech, Hong Kong). The relative protein levels of CD36 and b-actin in the original total protein lysate from the breast preparations were obtained. CD36 protein expression was normalized to beta-actin protein expression. Immunizing host produced the antibodies with a synthetic peptide derived from the sequence of human CD36, purified by peptide affinity chromatography and confirmed using control peptides. The results of the western blot analysis CD36 protein in 3 explant samples are shown in FIG. 22 at baseline and after 24 hours of cultivation. Cell lysates were immunoblotted with antibodies to CD36. The experiment was performed twice with similar results. Data are expressed relative to actin. A 2-tailed student t-test revealed significance at p=0.00757. The results are set forth in Table 11 below.

TABLE 11

| Patient number | Pre-treatment | Post-treatment |
| --- | --- | --- |
| 1 | 0.3235 | 0.9845 |
| 2 | 0.2135 | 1.0156 |
| 3 | 0.1478 | 0.4875 |
| Mean | 0.2283 | 0.8292 |
| SD | 0.0888 | 0.29634 |

Increasing CD36 increases conversion of fibroblasts to adipocytes (fat). The adipocytes (fat) is a semi-fluid and therefore has greater elasticity. The present example shows a significant increase in CD36 which is associated with a reduction in breast stiffness. Certain embodiments are directed to use of a combination therapy of an androgenic agent and an aromatase inhibitor to increase CD36 and a reduction in breast stiffness.

Example 14: Normal Peri-Menopausal Breast Tissue and Androgen Receptor Stabilization To test the level of androgen receptor in response to an androgenic agent and an aromatase inhibitor in normal breast tissue, samples of normal breast tissue were taken from 4 peri-menopausal women undergoing surgery for non-malignant breast procedures. The tissue was transported to a laboratory on ice, with a maximum time of one hour between excision and tissue processing. The breast tissue samples were washed in media (phenol red-free RPMI; SAFC biosciences, Kansas, USA), supplemented with 5 ml of 200 mM glutamine (SAFC biosciences, Kansas, USA), 5 ml of 100× anti-biotic/anti-mycotic (Sigma, St Louis, Mo., USA), 10 µg/ml insulin (Sigma, St Louis, Mo., USA), and 10 µg/ml hydrocortisone (Sigma, St Louis, Mo., USA) to remove excess blood. A representative piece of each tissue sample was immediately fixed in 4% formalin in phosphate-buffered saline (PBS) overnight at 4° C., followed by dehydration using an automatic tissue processor (Sakura Tissue-Tek VIP, USA) and paraffin wax embedding. A haematoxylin and eosin (H&E) stained section was used to assess tissue pathology. Additional consecutive sections were subjected to antigen retrieval to assess androgen receptor levels by immunohistochemistry (IHC). The remaining fresh tissue was cut into small (~3×3×1 mm) pieces, and placed as triplicates on 1 cm$^3$ gelatin sponges (Spongostan; Johnson & Johnson, Skipton, UK) that were pre-soaked and then half submerged in treatment media containing 10% dextran-coated charcoal stripped fetal calf serum (DCC-FCS) (SAFC biosciences, Kansas, USA) in 24-well tissue culture plates (BD Biosciences, NJ, USA). The tissues samples were cultured for 24 hours in a vehicle of 0.1% ethanol, 5 nM testosterone and 25 ng/ml anastrozole. Following 24 h culture in a 5% $CO_2$ enriched atmosphere at 37° C., the treated tissues samples were processed for IHC analyses as indicated below.

Immunohistochemistry: Established IHC protocols were used to determine hormone receptor androgen receptor status in the 4 tissue samples prior to culture. Following microwave antigen retrieval in 1 M citrate buffer (pH6.5) tissue sections were incubated at 4° C. overnight with primary antibody for androgen receptor in a ratio of 1:300. Visualization of androgen receptor in uncultured tissues immunoreactivity was achieved with a standard immunoperoxidase reaction utilising biotinylated goat anti-rabbit (AR 1:400, Santa Cruz Biotechnology). Negative controls were generated by replacement of the primary antibodies with PBS. Tissues were dehydrated in ethanol and xylene and mounted with DPX (VWR International Ltd, England, UK).

Image Analysis: Following staining, digital images of stained sections were generated with a NanoZoomer scanner (Hamamatsu, Japan) to enable analyses of AR % positivity in untreated tissues, using Visual Image Analysis software (Video Pro 32, Leading Edge Inc, South Australia). Photos of the pre-treatment slide samples are shown in FIG. 23A with an untreated control being observed in the inner lower corner of Patient 1. Photos of the post-treatment slide samples are shown in FIG. 23B with an untreated control being observed in the inner lower corner of Patient 1. Table 12 below shows that in normal human explant tissue samples the mean percent positive on the androgen receptor went from 31.25 to 57.25 after treatment.

TABLE 12

| Pre-treatment mean % positive | AR Post-treatment mean % positive AR |
| --- | --- |
| 31.25 (SD 6.9) | 57.25 (SD 14.8) | p = 0.001 2-tailed student t-test

This example shows that the application of an androgenic agent and an aromatase inhibitor to normal breast tissue results in stabilization and/or an increase in levels of androgen receptor expression. The benefits of increasing and/or stabilizing androgen receptor expression include, at least in part, one or more of the following:

1. chemo-prevention for estrogen receptor positive, progesterone receptor negative and androgen receptor positive breast cancer;
2. chemo-prevention for estrogen receptor negative, progesterone receptor positive and androgen receptor positive breast cancer;
3. chemo-prevention for estrogen receptor negative, progesterone receptor negative and androgen receptor positive breast cancer;
4. chemo-prevention for estrogen receptor negative, progesterone receptor negative and androgen receptor negative breast cancer;
5. chemo-prevention for estrogen receptor positive, progesterone receptor positive and androgen receptor positive breast cancer; and
6. enhancing androgenecity in the breast tissue of patients with diminished potency of androgen signaling secondary to presence of an expanded number of CAG polymorphic repeats in the amino-terminus of the androgen receptor.

Example 15: Macromastia

A 24 year old woman presented with rapid painful distention of her breasts with superficial inflammation. Prior to the macromastia she wore a B cup brassiere but over a 2 month period her brassiere size went to double E. FIG. 24A shows the inflamed breast after tamoxifen and oral contraceptive therapy failed to cease the breast growth.

The treatment consisted of testosterone 100 mg and anastrozole 3 mg compounded into a 4.5 mm pellet. The pellet was inserted into the subcutaneous fat of the lower abdominal wall. The patient's pain scale was 100 mm (on a 0-100 mm visual analogue pain scale where 100 mm is the worst pain and 0 is no pain) pre-treatment. After one month of treatment the patient's pain scale was 50 mm.

Prior to treatment (Pre-treatment) the right and left breasts were separately placed in a calibrated bucket and the volume of displacement for each breast was measured. This was accomplished by submerging each breast until the breast was fully submerged but the water was not touching the chest wall. After one month of treatment the volume measurements were repeated using the same water displacement methodology. Fluid displacements were measured in mls. FIG. 24B shows the inflamed breasts after treatment. The reduction in breast volume is set forth in Table 13 below.

TABLE 13

|  | Volume (mls) | Total Volume (mls) |
| --- | --- | --- |
| Left breast pre-therapy | 2145 |  |
| Right breast pre-therapy | 2845 | 4990 |
| Left breast post-therapy | 1756 |  |
| Right breast post-therapy | 2187 | 3943 |

As can be seen from Table 13, after one month of treatment there was a substantial reduction in breast volume (approximately 1 liter which approximates 1 kg in breast weight), pain, inflammation and breast elasticity as demonstrated by the ptosis (drooping) of the left nipple to the umbilicus as shown in FIG. 24B. Thereafter a surgical reduction mammoplasty was performed and the results are shown in FIG. 24C three months after treatment and the reduction mammoplasty.

This example demonstrates a significant reduction in massive macromastia in a patient.

Example 16: GCDFP15

The example demonstrates that the plasma of women treated with androgenic agent and aromatase inhibitor results in a beneficial increase in GCDFP15. Four peri-menopausal women with moderate or above classification of breast density were treated at the Wellendhealth Clinic Burnside Hospital, Toorak Gardens South Australia, with testosterone (80 mg) combined with anastrozole (2 mg) compounded into a 4.5 mm pellet and inserted into the subcutaneous fat of either the lower anterior abdominal wall or the upper outer gluteal region. The serum level of GCDFP15 before and after treatment for 3 months (one pellet) and the volume of breast density percentage (VBD %) before and after treatment for 12 months is set forth below in Table 14.

Radioimmunoassay of pre and post treatment of the four women was analyzed for GCDFP15 at baseline and at 3 months. They then went on to have 2 more pellets inserted at 4 and 8 months at the same dosing. As you can see the mean GCDFP15 after 3 months was raised by a factor of approximately 4-fold at baseline (table 15) and the mean breast density was reduced (table 16).

TABLE 14

| Patient | Pre-treatment serum GCDFP15 (ng/ml) | Post-treatment serum GCDFP15 (ng/ml) | Pre-treatment VBD % | Post-treatment VBD % |
| --- | --- | --- | --- | --- |
| 1 | 21 | 145 | 19 | 12 |
| 2 | 32 | 165 | 21 | 16 |
| 3 | 15 | 108 | 20 | 15 |
| 4 | 55 | 94 | 35 | 29 |

TABLE 15

| Mean pre-treatment GCDFP15 | Mean post-treatment GCDFP15 |
| --- | --- |
| 30.75 (SD 17.6) ng/ml | 128 (SD 32.7) ng/ml | p = 0.002 2-tailed student t-test for variance of the mean.

TABLE 16

| Mean pre-treatment VBD % | Mean post-treatment VBD % |
| --- | --- |
| 23.75 (SD 7.5) | 15.58 (SD 14.3) | p = 0.002 2-tailed student t-test for variance of the mean.

This example shows that treating women with moderate or above classification of breast density results in a beneficial increase in GCDFP15 and beneficial reduction of the VBD %.

Example 17: Prophetic VBD %

A 48 year old peri-menopausal woman with high mammographic breast density and has VBD % of 30% is subjected to aromatase inhibitor therapy with 0.5-10 mg anastrozole (2,2'-[5-(1H-1,2,4-triazol-1-ylmethyl)-1,3-phenylene]bis(2-methylpropanenitrile)) orally as a tablet once a day in combination with at least one of the following amounts of an Arl propionamide androgenic agent such as (2S)-3-(4-cyanophenoxy)-N-[4-cyano-3-(trifluoromethyl) phenyl]-2-hydroxy-2-methylpropanamide (also known as Enobosarm, Ostarine, GTx-024, and MK-2866), 3, 6, 9, 12, 15 or 18 mg orally as a tablet once a day. At repeat mammography and repeat breast density analysis at 1 year the VBD % is 25% approximately a 17% reduction in mammographic breast density.

Example 18: Prophetic VBD %

A 43 year old peri-menopausal woman with high mammographic breast density and has VBD % of 15.5% is subjected to aromatase inhibitor therapy with 1 mg anastrozole (2,2'-[5-(1H-1,2,4-triazol-1-ylmethyl)-1,3-phenylene] bis(2-methylpropanenitrile)) orally as a tablet once a day in combination with at least one of the following amounts of a Quinolinone androgenic agent such as (4-((R)-2-((R)-2,2,2-trifluoro-1-hydroxyethyl)pyrrolidin-1-yl)-2-trifluoromethyl)benzonitrile (also known as LGD4033, or Ligandrol), 0.1, 0.3, 0.5, 0.75 or 1 mg orally as a tablet once a day. At repeat mammography and repeat breast density analysis at 1 year the VBD % is 12.5% and approximately a 19% reduction in mammographic breast density.

Example 19: Prophetic Pain

A 35 year old woman with severe breast pain (100 mm on a 0-100 mm visual analogue scale (VAS) where 100 mm is the worst pain) is subjected to aromatase inhibitor therapy with 1 mg anastrozole (2,2'-[5-(1H-1,2,4-triazol-1-ylmethyl)-1,3-phenylene]bis(2-methylpropanenitrile)) orally as a tablet once a day in combination with at least one of the following amounts of a Tetrahydroquinolone androgenic agent such as (3aS,4S,9bS)—N-[2-(8-Cyano-1-formyl-2,3,3a,4,5,9b-hexahydro-1H-pyrrolo[3,2-c]quinolin-4-yl)-2-methylpropyl]-4,6-difluorobenzofuran-2-carboxyamide (also known as S-101479)), 5, 10, 15 or 20 mgmg orally as a tablet once a day for 3 months. At 3 months from initiation of therapy a repeat VAS revealed a reduction in pain score of 45 mm.

Example 20: Prophetic Stiffness

A 45 year old peri-menopausal woman with high mammographic breast density of 28% VBD % selected to undergo therapy to reduce breast stiffness and is subjected to aromatase inhibitor therapy with 1 mg anastrozole (2,2'-[5-(1H-1,2,4-triazol-1-ylmethyl)-1,3-phenylene]bis(2-methylpropanenitrile)) orally as a tablet once a day in combination with at least one of the following amounts of a Hydantoin androgenic agent such as (4-[(7R,7aS)-7-hydroxy-1,3-dioxo-5,6,7,7a-tetrahydropyrrolo[1,2-c]imidazol-2-yl]-2-chloro-3-methylbenzonitrile (also known BMS-564929), 5, 10, 15 or 20 mg orally as a tablet once a day. At baseline mammogram the breast stiffness was measured at 46 (N/cm) as measured by the equation of Boyd (cited in full within this patent) and was 23 (N/cm) at 1 year a reduction of 50%.

Example 21: Prophetic GCDFP15

A 42 year old peri-menopausal woman with high mammographic breast density and has VBD % of 24% is subjected to aromatase inhibitor therapy with 0.5-10 mg anastrozole (2,2'-[5-(1H-1,2,4-triazol-1-ylmethyl)-1,3-phenylene]bis(2-methylpropanenitrile)) orally as a tablet once a day in combination with at least one of the following amounts of an Arl propionamide androgenic agent such as (2S)-3-(4-cyanophenoxy)-N-[4-cyano-3-(trifluoromethyl) phenyl]-2-hydroxy-2-methylpropanamide (also known as Enobosarm. Ostarine, GTx-024, and MK-2866), 3, 6, 9, 12, 15 or 18 mg orally as a tablet once a day to increase her serum GCDFP15. At baseline her serum GCDFP15 was 23 (ng/ml) and after 3 months of therapy repeat serum GCDFP15 was 98 (ng/ml)

Example 22: Prophetic Fat to Fibro-Glandular Ratio

A 39 year old woman with high mammographic breast density and has VBD % of 35% is subjected to therapy to increase her fat to fibro-glandular ratio as part of a reducing her breast tissue elasticity. Aromatase inhibitor therapy with 1 mg anastrozole (2,2'-[5-(1H-1,2,4-triazol-1-ylmethyl)-1,3-phenylene]bis(2-methylpropanenitrile)) orally as a tablet once a day in combination with at least one of the following amounts of a Quinolinone androgenic agent such as (4-((R)-2-((R)-2,2,2-trifluoro-1-hydroxyethyl)pyrrolidin-1-yl)-2-trifluoromethyl)benzonitrile (also known as LGD-4033, or Ligandrol), 0.1, 0.3, 0.5, 0.75 or 1 mg orally as a tablet once a day. Using shear wave elastography (described herein) at baseline adipose elasticity was 93.1 (kPa) and at the end of 3 months of treatment was 43.4 (kPa). Fibro-glandular measurements were 124.4 (kPa) at baseline and 81.7 (kPa) after 3 months of treatment. Thus the fat:fibro-glandular ratio was 1.34 before treatment and increase to 1.88 after treatment.

Example 23: Prophetic Macromastia

A 28 year old woman with severe macromastia is subjected to aromatase inhibitor therapy with Img anastrozole (2,2'-[5-(1H-1,2,4-triazol-1-ylmethyl)-1,3-phenylene]bis(2-methylpropanenitrile)) orally as a tablet once a day in combination with at least one of the following amounts of a Tetrahydroquinolone androgenic agent such as (3aS,4S, 9bS)—N-[2-(8-Cyano-1-formyl-2,3,3a,4,5,9b-hexahydro-1H-pyrrolo[3,2-c]quinolin-4-yl)-2-methylpropyl]-4,6-difluorobenzofuran-2-carboxyamide (also known as S-101479)), 5, 10, 15 or 20 mg orally as a tablet once a day for 3 months. At baseline the volume of both breasts was 3991 mls as measured by water displacement and after treatment the volume of both breasts had reduced to 2132 mls.

Example 24: Prophetic FSH and LH Levels

A 38 year old peri-menopausal woman with high mammographic breast density of 30% VBD % selected to undergo therapy to reduce VBD % and is subjected to aromatase inhibitor therapy with 1 mg anastrozole (2,2'-[5-(1H-1,2,4-triazol-1-ylmethyl)-1,3-phenylene]bis(2-methylpropanenitrile)) orally as a tablet once a day in combination with at least one of the following amounts of a Hydantoin androgenic agent such as (4-[(7R,7aS)-7-hydroxy-1,3-dioxo-5,6,7,7a-tetrahydropyrrolo[1,2-c]imidazol-2-yl]-2-chloro-3-methylbenzonitrile (also known BMS-564929), 5, 10, 15 or 20 mg orally as a tablet once a day. At baseline her FSH and LH levels was 12 (U/L) and 8 (U/L) respectively. After 3 months her FSH and LH levels was 8 (U/L) and 11 (U/L) respectively at the same time of her menstrual cycle; showing there was no change in level of either hormone.

Example 25 Background Parenchyma Enhancement on MRI

In magnetic resonance imaging (MRI), both normal and abnormal breast tissue enhances after contrast material administration. The morphology and temporal degree of enhancement of pathologic breast tissue relative to normal breast tissue forms the basis of MR imaging's diagnostic accuracy in the detection and diagnosis of breast disease. Normal parenchymal enhancement in breast MRI may be termed background parenchymal enhancement (BPE). BPE may vary in degree and distribution in different patients as well as in the same patient over time. Typically BPE is minimal or mild in overall degree, with a bilateral, symmetric, diffuse distribution and slow early and persistent delayed kinetic features. However, BPE may sometimes be moderate or marked in degree, with an asymmetric or non-diffuse distribution and rapid early and plateau or washout delayed kinetic features. These patterns cause diagnostic difficulty because these features can be seen with malignancy. BPE may be difficult to measure. Subjective quantization has been developed to measure the amount of BPE as either mild, moderate, high or extreme. Semiautomated techniques are available but not widely used or validated.

The following examples are directed to the use of an androgenic agent and an aromatase inhibitor and their impact on BPE as determined by MRI. Example 25A demonstrates a correlation of BPE with VBD %. The VBD % in this example was measured using Volpara Solution™ breast density analysis software. Example 25A also demonstrates ions the lack of effect of the treatment on pituitary function (as determined by LH and FSH) whilst in the presence of elevated testosterone levels that fall within the therapeutic window of 5% to 15% free androgen index. The subsequent examples (Examples 25B-E) are pre-menopausal women having received between 10 and 14 months of an androgenic agent and an aromatase inhibitor therapy. BPE may be considered a subjective analysis with radiologists typically placing the value at mild, moderate, high or extreme (also called marked). Examples 25B-E are cases of patients with extreme BPE with 4 of them falling to moderate BPE after treatment and one falling to mild BPE after treatment.

Example 25A: BPE on 46 Year Pre-Menopausal Patient

An MRI image was taken pre-treatment of a 46 year old pre-menopausal woman breasts. This patient had a strong family history of breast cancer and significant peri-menopausal symptoms. The images of the patient's breasts pre-treatment (FIG. 25A) were evaluated by a radiologist and the patient was labeled as having an Extreme BPE in both breasts. Thereafter, the patient was treated with 60 mg testosterone combined with 2 mg anastrozole compounded into a 4.5 mm pellet and inserted into the subcutaneous fat of either the lower anterior abdominal wall or the upper outer gluteal region, as per the dosing algorithm provided herein.

Approximately five days after treatment was commenced, a second set of MRI images of the patient's breast (FIG. 25B) were taken and evaluated by a radiologist. The patient was labeled as having a Moderate BPE in both breasts. Thus a short time after treatment was commenced the patient's BPE was reduced from Extreme to Moderate. This reduction in BPE results in an improved MRI imaging diagnostic accuracy in the detection and/or diagnosis of breast disease for this patient.

Approximately 3 months later the patient was treated with another 4.5 mm pellet of 80 mg testosterone combined with 2 mg anastrozole and again inserted into the subcutaneous fat of either the lower anterior abdominal wall or the upper outer gluteal region, as per the dosing algorithm provided herein. A third 4.5 mm pellet of 80 mg testosterone combined with 2 mg anastrozole was inserted into the patient's subcutaneous fat of either the lower anterior abdominal wall or the upper outer gluteal region at approximately 6 months. In total the patient received three injections of the combined testosterone and anastrozole.

Approximately seven weeks after treatment was commenced blood was drawn from the patient and the FSH and LH levels determined as shown in FIG. 26A. FIG. 26A shows an LH of 6 U/L and a FSH of 7.9. Approximately 24 weeks after treatment commenced blood was again drawn from the patient and the LH and FSH levels determined as shown in FIG. 26B. FIG. 26B shows an LH of 9.7 U/L and a FSH of 7.5. These LH and FSH remained in pre-menopausal range even after treatment was commenced. In short, the androgenic agent and the aromatase inhibitor treatment had no significant impact on the hypothalamic-pituitary function as demonstrated by serum FSH and LH levels.

Mammograms were taken of the patient's breasts both before pre-treatment and post-treatment (approximately 14 months later). Volpara Solution™ analysis was conducted on the data and the results are shown in FIG. 27A (pre-treatment) and FIG. 27B post-treatment. The data shows approximately a 13% reduction in fibro-glandular volume (AVBD) and a 26.5% reduction in the percentage of fibro-glandular tissue volume to total breast volume (VBD %).

Example 25B: Effects Treatment on BPE in a 42 Year Old Pre-Menopausal Patient

An MRI image was taken pre-treatment of a 42 year old pre-menopausal woman breasts. This patient had a strong family history of breast cancer and significant peri-menopausal symptoms. The images of the patient's breasts pre-treatment (FIG. 28A) were evaluated by a radiologist and the patient was labeled as having an Extreme BPE in both breasts. Thereafter, the patient was treated 4 times at 4 month intervals with 80 mg testosterone combined with 2 mg anastrozole compounded into a 4.5 mm pellet and inserted into the subcutaneous fat of either the lower anterior abdominal wall or the upper outer gluteal region, as per the dosing algorithm provided herein.

Approximately 14 months later, a second set of MRI images of the patient's breast (FIG. 28B) was taken post-treatment and evaluated by a radiologist. The patient was labeled as having a Moderate BPE in both breasts. Thus after 14 months of treatment the patient's BPE was reduced from Extreme to Moderate. This reduction in BPE results in an improved MRI imaging diagnostic accuracy in the detection and/or diagnosis of breast disease for this patient.

Example 25C: Effect of Treatment on the BPE a 45 Year Old Pre-Menopausal Patient An MRI image was taken pre-treatment of a 45 year old pre-menopausal woman breasts. This patient had a strong family history of breast cancer and significant peri-menopausal symptoms. The images of the patient's breasts pre-treatment (FIG. 29A) were evaluated by a radiologist and the patient was labeled as having an Extreme BPE with a large number of cysts both in quantity and size in both breasts. Thereafter, the patient was treated 4 times at 4 month intervals with 80 mg testosterone combined with 2 mg anastrozole compounded into a 4.5 mm pellet and inserted into the subcutaneous fat of either the lower anterior abdominal wall or the upper outer gluteal region, as per the dosing algorithm provided herein.

Approximately 14 months later, a second set of MRI images of the patient's breast (FIG. 29B) was taken post-treatment and evaluated by a radiologist. The patient was labeled as having a Moderate BPE in both breasts with a much smaller number of cysts both in quantity and size. Thus after 14 months of treatment the patient's BPE was reduced from Extreme to Moderate and the number of cysts reduced both in quantity and size in both breasts. This reduction in BPE results in an improved MRI imaging diagnostic accuracy in the detection and/or diagnosis of breast disease for this patient.

Example 25D: BPE on a 48 Year Old Peri-Menopausal Patient

An MRI image was taken pre-treatment of a 48 year old peri-menopausal woman breasts. This patient had significant peri-menopausal symptoms. The images of the patient's breasts pre-treatment (FIG. 30A) were evaluated by a radiologist and the patient was labeled as having an Extreme BPE in both breasts. Thereafter, the patient was treated 4 times at 4 month intervals with 80 mg testosterone combined with 2 mg anastrozole compounded into a 4.5 mm pellet and inserted into the subcutaneous fat of either the lower anterior abdominal wall or the upper outer gluteal region, as per the dosing algorithm provided herein.

Approximately 11 months later, a second set of MRI images of the patient's breast (FIG. 30B) was taken during treatment and evaluated by a radiologist. The patient was labeled as having a Mild BPE in both breasts. Thus after 11 months of treatment the patient's BPE was reduced from Extreme to Moderate and the number of cysts reduced both in quantity and size in both breasts. This reduction in BPE results in an improved MRI imaging diagnostic accuracy in the detection and/or diagnosis of breast disease for this patient.

Example 25E: BPE on a 48 Year Old Peri-Menopausal Patient

An MRI image was taken pre-treatment of a 48 year old peri-menopausal woman breasts. This patient had a strong family history of breast cancer and significant peri-menopausal symptoms. The images of the patient's breasts pre-treatment (FIG. 31A) were evaluated by a radiologist and the patient was labeled as having an Extreme BPE in both breasts. Thereafter, the patient was treated 4 times at 4 month intervals with 80 mg testosterone combined with 2 mg anastrozole compounded into a 4.5 mm pellet and inserted into the subcutaneous fat of either the lower anterior abdominal wall or the upper outer gluteal region, as per the dosing algorithm provided herein.

Approximately 13 months later, a second set of MRI images of the patient's breast (FIG. 31B) was taken post-treatment and evaluated by a radiologist. The patient was labeled as having a Moderate BPE in both breasts. Thus after 13 months of treatment the patient's BPE was reduced from Extreme to Moderate and the number of cysts reduced both in quantity and size in both breasts. This reduction in BPE results in an improved MRI imaging diagnostic accuracy in the detection and/or diagnosis of breast disease for this patient.

Example 26: Reduction in Breast Cyst Formation and Breast Pain

FIG. 32A shows the left caudo-cranial mammogram of a 49 years old peri-menopausal woman 12 months before treatment. This mammogram shows moderate to severe breast cysts consistent with peri-menopausal hormonal dysfunction.

The patient was treated over a period of 10 months (the time between mammograms) with 4 doses of testosterone 80 mg and anastrozole 2 mgs compounded in a 4.5 mm pellet. For each treatment the pellet was inserted into the subcutaneous fat of the lower abdominal wall of the patient. The first pellet was inserted on day one of treatment into the lower abdominal wall. Four months later a second pellet with the same dosage was inserted into the lower abdominal wall of the patient. 10 months after initial treatment a mammogram of the left caudo-cranial of the patient was taken as shown in FIG. 32B. The mammogram in FIG. 32B shows a significant reduction in the size and quantity of cysts. The patient reported a substantial reduction in breast pain from 90 mm (FIG. 33A) pre-treatment on a 0-100 mm visual analogue scale to 20 mm (FIG. 33B) after treatment commenced. On this scale 100 mm is the worst pain and 0 mm is no pain. The patient is requested to mark a mark on a line to indicate their pain. There are no markings on the line apart from where the 0 mm and the 100 mm mark are located and the 0 mm is no pain and 100 mm is worse pain. This pain reduction occurred in the first month of treatment. This example demonstrates that treatment with an androgenic agent and an aromatase inhibitor may substantially reduce the size and quantity of cysts as well as substantially reduce in breast pain.

Example 27: Reduction in Breast Cyst Formation

A 45 year old woman with severe breast pain secondary to the inflammation associated with breast cysts was treated with 4 doses over 15 months. The woman had severe breast pain and frequent bouts of inflammatory mastitis with the breast becoming red and intensely painful responding only to cyst aspiration and non-steroidal anti-inflammatories. Her pain scale at baseline was 100 mm on a 0-100 mm VAS pain-scale and fell to 10 mm after 6 weeks of treatment. The doses were given every four months, i.e., day one, 4 months, 8 months and 12 months. The dosage amount was 100 mg of testosterone and 3 mg of anastrazole that were compounded together in a 4.5 mm pellet and each pellet was inserted into subcutaneous fat of the upper outer quadrant of the gluteal region of the patient.

MRI imaging with contrast agent of the patients breasts were taken of the patient pre-treatment as shown in FIG. 34A. FIG. 34A shows 12 large cysts (aggregated over both breasts). FIG. 34B shows the MRI of the patient's breast 15 months after the treatment. FIG. 34B shows a substantial reduction in cysts to 3.

Example 28: BPE on a 45 Year Woman

A 45-year-old woman with high mammographic breast density and a strong family history of breast cancer commenced testosterone and an aromatase inhibitor treatment to reduce the mammographic breast density and her risk of developing breast cancer.

FIG. 35A is an MRI image that shows the BPE of her left breast in a sagittal view pre-treatment. The BPE was labeled as extreme with the upper half of the breast demonstrating similar BPE to the lower half of the breast contained within the rectangle marked on the image in FIG. 35A. The patient received testosterone 80 mg and anastrozole 2 mg combined into a 4.5 mm pillows and inserted in the lower abdominal wall subcutaneous fat. After four repeat administration's of the same dosage of the pellet over approximately a 12 month period with treatments approximately every four months a repeat MRI revealed a substantial difference in the BPE between the upper and lower parts of the breast is indicated by the black rectangle superimposed on the image in FIG. 35B. FIG. 35B is an MRI image taken after approximately 12 months of treatment. Mammography and ultrasound of the region failed to reveal any abnormality and a MRI guided biopsy was undertaken of the region which revealed atypical ductal hyperplasia. This lesion was extensive and probably was present in the pre-treatment MRI image (FIG. 35A) but was obscured by the extreme BPE. FIG. 36 reveals the corresponding mammogram following the biopsy and revealing a clip in the location of the biopsy. There is no mammographic evidence of disease.

This example demonstrates the effectiveness of treatment in aiding in and revealing a premalignant condition within the MRI image which otherwise would not have been located.

In the following, further embodiments are explained with the help of subsequent examples.

Example A1. A method of treating mammographic breast density and/or breast stiffness in a patient in need thereof, comprising administering to the patient:
i) an effective amount of androgenic agent; and
ii) an effective amount of an aromatase inhibitor.

Example A2. A method of treating mammographic breast density and/or breast stiffness in a patient in need thereof, comprising administering to the patient a pharmaceutical composition comprising:
i) an effective amount of androgenic agent;
ii) an effective amount of an aromatase inhibitor; and
iii) optionally, a pharmaceutically acceptable excipient and/or carrier.

Example A3. A method of treating mammographic breast density in a patient having a breast with a BI-RADS® score of 3 or 4 (or c or d), comprising administering to the patient:
i) an effective amount of androgenic agent; and
ii) an effective amount of an aromatase inhibitor.

Example A4. A method of treating mammographic breast density in a patient having a breast with a BT-RADS® score of 3 or 4 (or c or d), comprising administering to the patient a pharmaceutical composition comprising:
i) an effective amount of androgenic agent;
ii) an effective amount of an aromatase inhibitor; and
iii) optionally, a pharmaceutically acceptable excipient and/or carrier.

Example A5. A method of reducing mammographic breast density in a patient having a breast with a mammographic breast density of 7.5% or greater, comprising administering to the patient:
i) an effective amount of androgenic agent; and
ii) an effective amount of an aromatase inhibitor.

Example A6. A method of reducing mammographic breast density in a patient having a breast with a mammographic breast density of 7.5% or greater, comprising administering to the patient a pharmaceutical composition comprising:
i) an effective amount of androgenic agent;
ii) an effective amount of an aromatase inhibitor; and
iii) optionally, a pharmaceutically acceptable excipient and/or carrier.

Example A7. A method of inducing breast involution in a patient in need thereof, comprising administering to the patient:
i) an effective amount of androgenic agent; and
ii) an effective amount of an aromatase inhibitor.

Example A8. A method of inducing breast involution in a patient in need thereof, comprising administering to the patient a pharmaceutical composition comprising:
i) an effective amount of androgenic agent;
ii) an effective amount of an aromatase inhibitor; and
iii) optionally, a pharmaceutically acceptable excipient and/or carrier.

Example A9. A method of inducing net cell death over proliferation in a breast of a patient in need thereof, comprising administering to the patient:
i) an effective amount of androgenic agent; and
ii) an effective amount of an aromatase inhibitor.

Example A10. A method of inducing net cell death over proliferation in a breast of a patient in need thereof, comprising administering to the patient a pharmaceutical composition comprising:
i) an effective amount of androgenic agent;
ii) an effective amount of an aromatase inhibitor; and
iii) optionally, a pharmaceutically acceptable excipient and/or carrier.

Example A11. A method of reversing cell number and mammographic breast density in a breast of a peri-menopausal patient, comprising administering to the patient:
i) an effective amount of androgenic agent; and
ii) an effective amount of an aromatase inhibitor.

Example A12. A method of reversing cell number and mammographic breast density in a breast of a peri-menopausal patient, comprising administering to the patient a pharmaceutical composition comprising:
i) an effective amount of androgenic agent;
ii) an effective amount of an aromatase inhibitor; and
iii) optionally, a pharmaceutically acceptable excipient and/or carrier.

Example A13. A method of reducing mammographic breast density and peri-menopausal symptoms in a patient in need thereof, comprising administering to the patient:
i) an effective amount of androgenic agent; and
ii) an effective amount of an aromatase inhibitor.

Example A14. A method of reducing mammographic breast density and peri-menopausal symptoms in a patient in need thereof, comprising administering to the patient a pharmaceutical composition comprising:
i) an effective amount of androgenic agent;
ii) an effective amount of an aromatase inhibitor; and
iii) optionally, a pharmaceutically acceptable excipient and/or carrier.

Example A15. A method of reducing breast stiffness in a patient in need thereof, comprising administering to the patient:
i) an effective amount of androgenic agent; and
ii) an effective amount of an aromatase inhibitor.

Example A16. A method of reducing breast stiffness in a patient in need thereof, comprising administering to the patient a pharmaceutical composition comprising:
i) an effective amount of androgenic agent;
ii) an effective amount of an aromatase inhibitor; and
iii) optionally, a pharmaceutically acceptable excipient and/or carrier.

Example A17. The method of any one of Examples A1-16, wherein the androgenic agent is a selective androgen receptor modulator.

Example A18. The method of any one of Examples A1-17, wherein the method further comprises:
a) measuring free androgenic index levels and/or aromatase inhibitor levels in serum isolated from a blood sample taken from the patient after at least 1 month of treatment;
b) determining a subsequent dose, comprising a subsequent effective amount of androgenic agent and a subsequent effective amount of an aromatase inhibitor; and
c) administering to the patient the subsequent dose.

Example A19. The method of any one of Examples A1-18, wherein the method further comprises:
a) measuring free androgenic index levels and/or aromatase inhibitor levels in serum isolated from a blood sample taken from the patient after at least 1 month of treatment, comprising centrifuging the patient's blood sample to isolate the serum;
b) determining a subsequent dose, comprising a subsequent effective amount of androgenic agent and a subsequent effective amount of an aromatase inhibitor; and
c) administering to the patient the subsequent dose.

Example A20. The method of any one of Examples A1-19, wherein the patient's breast has a BI-RADS® score of 3 or 4 (or c or d).

Example A21. The method of any one of Examples A1-20, wherein the patient's breast has a BI-RADS® score of 4 (or d).

Example A22. The method of any one of Examples A1-21, wherein the patient's breast has a mammographic breast density of 7.5% or greater.

Example A23. The method of any one of Examples A1-22, wherein the patient's breast has a mammographic breast density of 25% or greater.

Example A24. The method of any one of Examples A1-23, wherein the patient's breast has a mammographic breast density of 50% or greater.

Example A25. The method of any one of Examples A1-24, wherein the patient's breast is a mammographically dense breast.

Example A26. The method of any one of Examples A1-25, wherein the patient's breast has the same or more breast tissue than fat.

Example A27. The method of any one of Examples A1-26, wherein the patient's breast has more breast tissue than fat.

Example A28. The method of any one of Examples A1-27, wherein the method reduces or decreases the patient's BI-RADS® score between 1 or more annual intervening mammographic detections.

Example A29. The method of any one of Examples A1-28, wherein the method maintains or stabilizes the patient's BI-RADS® score between 1 or more annual intervening mammographic detections.

Example A30. The method of any one of Examples A1-29, wherein the patient's BI-RADS® score reduces or decreases by 2 or more.

Example A31. The method of any one of Examples A1-30, wherein the patient's BI-RADS® score reduces or decreases by 3 or 4.

Example A32. The method of any one of Examples A1-31, wherein the patient's BI-RADS® score reduces or decreases by 4.

Example A33. The method of any one of Examples A1-32, wherein the patient is peri-menopausal.

Example A34. The method of any one of Examples A1-33, wherein the patient is post-menopausal.

Example A35. The method of any one of Examples A1-34, wherein the method reduces or decreases the mammographic breast density of the patient's breast between one or more annual intervening mammographic detections.

Example A36. The method of any one of Examples A1-35, wherein the mammographic breast density reduces by at least 2% per annum.

Example A37. The method of any one of Examples A1-36, wherein the mammographic breast density reduces by at least 8% per annum.

Example A38. The method of any one of Examples A1-37, wherein the mammographic breast density reduces by at least 30% per annum.

Example A39. The method of any one of Examples A1-38, wherein the mammographic breast density reduces or decreases 20-40% per annum.

Example A40. The method of any one of Examples A1-39, wherein the reduction or decrease in the mammographic breast density is in the range of between 1% to 99%.

Example A41. The method of any one of Examples A1-40, wherein the reduction or decrease in the mammographic breast density is in the range of between 10% to 90%.

Example A42. The method of any one of Examples A1-41, wherein the reduction or decrease in the mammographic breast density is in the range of between 1% to 50%.

Example A43. The method of any one of Examples A1-42, wherein the method maintains or stabilizes the mammographic breast density of the patient's breast between one or more annual intervening mammographic detections.

Example A44. The method of any one of Examples A1-43, wherein the method reduces or decreases the breast stiffness of the patient's breast between one or more annual intervening mammographic detections.

Example A45. The method of any one of Examples A1-44, wherein the breast stiffness reduces by at least 5% per annum.

Example A46. The method of any one of Examples A1-45, wherein the breast stiffness reduces by at least 10% per annum.

Example A47. The method of any one of Examples A1-46, wherein the breast stiffness reduces by at least 25% per annum.

Example A48. The method of any one of Examples A1-47, wherein the breast stiffness reduces by at least 50% per annum.

Example A49. The method of any one of Examples A1-48, wherein the breast stiffness reduces or decreases 20-40% per annum.

Example A50. The method of any one of Examples A1-49, wherein the reduction or decrease in the breast stiffness is in the range of between 1% to 99%.

Example A51. The method of any one of Examples A1-50, wherein the reduction or decrease in the breast stiffness is in the range of between 10% to 90%.

Example A52. The method of any one of Examples A1-51, wherein the reduction or decrease in the breast stiffness is in the range of between 1% to 50%.

Example A53. The method of any one of Examples A1-52, wherein the method maintains or stabilizes the breast stiffness of the patient's breast between one or more annual intervening mammographic detections.

Example A54. The method of any one of Examples A1-53, wherein the mammographic breast density reduces by at least 2% per annum and the breast stiffness reduces by at least 10% per annum.

Example A55. The method of any one of Examples A1-54, wherein the method mitigates, reduces, or decreases, the treated patient's risk of developing breast cancer.

Example A56. The method of any one of Examples A1-55, wherein the method mitigates, reduces, or decreases, the treated patient's risk of developing breast cancer between one or more annual intervening mammographic detections.

Example A57. The method of any one of Examples A1-56, wherein the method mitigates, reduces, or decreases, the treated patient's risk of developing breast cancer and avoids, mitigates, reduces, or reverses one or more perimenopausal symptoms.

Example A58. The method of any one of Examples A1-57, wherein the method enhances, increases, or improves, mammographic visualization or detection of the breast.

Example A59. The method of any one of Examples A1-58, wherein the method enhances, increases, or improves, the treated patient's fat to breast tissue ratio.

Example A60. The method of any one of Examples A1-59, wherein the patient's fat to breast tissue ratio increases in the range of between 1% to 99%.

Example A61. The method of any one of Examples A1-60, wherein the patient's fat to breast tissue ratio increases in the range of between 1% to 50%.

Example A62. The method of any one of Examples A1-61, wherein the patient's fat to breast tissue ratio increases in the range of between 3% to 20%

Example A63. The method of any one of Examples A1-62, wherein the method increases the percentage of fat in the treated patient's breast.

Example A64. The method of any one of Examples A1-63, wherein the method enhances, increases, or improves, breast compression during mammographic visualization or detection of the breast.

Example A65. The method of Example A64, wherein the method mitigates, reduces, or decreases, pain during the breast compression.

Example A66. The method of any one of Examples A1-65, wherein the method mitigates, reduces, or decreases the treated patient's pain during mammographic visualization or detection of the breast.

Example A67. The method of Example A66, wherein the method enhances, increases, or improves breast compression during the breast compression.

Example A68. The method of any one of Examples A1-67, wherein the method enhances, increases, or improves the treated patient's compliance of having regular mammographic visualizations or detections.

Example A69. The method of any one of Examples A1-68, wherein the method mitigates, reduces, or decreases, the amount of radiation exposure required to visualize or detect the treated patient's breast during one or more subsequent mammographies.

Example A70. The method of any one of Examples A1-69, wherein the method induces breast involution.

Example A71. The method of any one of Examples A1-70, wherein the method induces involution of breast cells in the patient.

Example A72. The method of any one of Examples A1-71, wherein the method induces net cell death over proliferation in the breast of the patient.

Example A73. The method of any one of Examples A1-72, wherein the method reverses cell number and mammographic breast density in the breast of the peri-menopausal patient.

Example A74. The method of any one of Examples A1-73, wherein the treated patient has a free androgenic index level of 30% or greater within their breast within four hours of the administration of the androgenic agent and the aromatase inhibitor.

Example A75. The method of any one of Examples A1-74, wherein the treated patient has a supra-physiological free androgenic index level within their breast within four hours of the administration of the androgenic agent and the aromatase inhibitor.

Example A76. The method of any one of Examples A1-75, wherein the administration of the aromatase inhibitor reduces aromatization of testosterone to estrogen in the subcutaneous fat of the patient's breast by at least 80%.

Example A77. The method of any one of Examples A1-76, wherein the administration of the androgenic agent and the aromatase inhibitor is a co-administration.

Example A78. The method of any one of Examples A1-77, wherein the co-administration comprises concurrently, simultaneously, substantially at the same time, or sequentially.

Example A79. The method of any one of Examples A1-78, wherein the method reduces mammographic breast density and avoids inducing masculinizing androgenic side-effects or inducing a hyper-androgenic state.

Example A80. The method of any one of Examples A1-79, wherein the method reduces mammographic breast density and is exclusive of inducing masculinizing androgenic side-effects or inducing a hyper-androgenic state.

Example A81. The method of any one of Examples A1-80, wherein the method reduces mammographic breast density and minimizes induction of masculinizing androgenic side-effects or induction of a hyper-androgenic state.

Example A82. The method of any one of Examples A1-81, wherein the method provides one or more of the following:
  i) reduces mammographic breast density;
  ii) increases involuntary effects on the treated patient's breast without conversion of testosterone to estrogen;
  iii) reduces or reverses peri-menopausal symptoms; or
  iv) improves the treated patient's physical functioning, comprising cognitive function; reduction of the symptoms of a degenerative CNS disease, comprising dementia or parkinsonism; muscle strength; libido; energy; reduction of monoamine oxidase induced anxiety and depression; or combinations thereof.

Example A83. The method of any one of Examples A1-82, wherein the method provides one or more of the following:
  i) reduces mammographic breast density;
  ii) increases involuntary effects on hormonally affected end organs, comprising breast, without conversion of testosterone to estrogen;
  iii) reduces or reverses peri-menopausal symptoms related to fluctuating estrogen levels; or
  iv) improves the treated patient's physical functioning, comprising cognitive function; reduction of the symptoms of a degenerative CNS disease, comprising dementia or parkinsonism; muscle strength; libido; energy; reduction of monoamine oxidase induced anxiety and depression; or combinations thereof.

Example A84. The method of any one of Examples A1-83, wherein the method substantially reduces or reverses peri-menopausal symptoms.

Example A85. The method of any one of Examples A1-84, wherein the method substantially improves the treated patient's physical functioning.

Example A86. The method of any one of Examples A1-85, wherein the method substantially reduces or reverses peri-menopausal symptoms related to fluctuating estrogen levels.

Example B1. A method of reducing VBD % and/or AVBD in a patient in need thereof, comprising administering to the patient:
  i) an effective amount of an androgenic agent; and
  ii) an effective amount of an aromatase inhibitor.

Example B2. A method of reducing breast stiffness in a patient in need thereof, comprising administering to the patient:
  i) an effective amount of an androgenic agent; and
  ii) an effective amount of an aromatase inhibitor.

Example B3. A method of reducing breast pain in a patient in need thereof, comprising administering to the patient:
  i) an effective amount of an androgenic agent; and
  ii) an effective amount of an aromatase inhibitor.

Example B4. A method of reducing breast elasticity in a patient in need thereof, comprising administering to the patient:
  i) an effective amount of an androgenic agent; and
  ii) an effective amount of an aromatase inhibitor.

Example B5. A method of decreasing mechano-transduction on the genome of a cell in order to reduce the risk of malignant transformation in a patient in need thereof, comprising administering to the patient:
  i) an effective amount of an androgenic agent; and
  ii) an effective amount of an aromatase inhibitor.

Example B6. A method of increasing the ratio of fibroglandular and adipose tissue in a patient in need thereof, comprising administering to the patient:
  i) an effective amount of an androgenic agent; and
  ii) an effective amount of an aromatase inhibitor.

Example B7. A method of increasing CD36 in a patient in need thereof, comprising administering to the patient:
  i) an effective amount of an androgenic agent; and
  ii) an effective amount of an aromatase inhibitor.

Example B8. A method of stabilizing and/or an increase in levels of androgen receptor expression in breast tissue of a patient in need thereof, comprising administering to the patient:
  i) an effective amount of an androgenic agent; and
  ii) an effective amount of an aromatase inhibitor.

Example B9. A method of reducing and/or treating macromastia in a patient in need thereof, comprising administering to the patient:
  i) an effective amount of an androgenic agent; and
  ii) an effective amount of an aromatase inhibitor.

Example B10. A method of increasing GCDFP15 in a patient in need thereof, comprising administering to the patient:
  i) an effective amount of an androgenic agent; and
  ii) an effective amount of an aromatase inhibitor.

Example B11. A method of reducing breast pain associated with having a mammography image taken in a patient in need thereof, comprising administering to the patient:
  i) an effective amount of an androgenic agent; and
  ii) an effective amount of an aromatase inhibitor.

Example B12. A method of increasing mammographic sensitivity in a patient, comprising administering to the patient:
  i) an effective amount of an androgenic agent; and
  ii) an effective amount of an aromatase inhibitor.

Example B13. A method of reducing ABD % and/or AABD in a patient in need thereof, comprising administering to the patient:
  i) an effective amount of an androgenic agent; and
  ii) an effective amount of an aromatase inhibitor.

Example B14. A method of reducing BPE in an MRI image of a patient, comprising administering to the patient:
  i) an effective amount of an androgenic agent; and
  ii) an effective amount of an aromatase inhibitor.

Example B15. A method of reducing the size and/or quantity of cysts in a patient in need thereof, comprising administering to the patient:
  i) an effective amount of an androgenic agent; and
  ii) an effective amount of an aromatase inhibitor.

Example B16. A method of reducing breast cancer in a patient in need thereof, comprising administering to the patient:
  i) an effective amount of an androgenic agent; and
  ii) an effective amount of an aromatase inhibitor.

Example B17. The method of one or more of Examples B1-B16, wherein there is a reduction in breast pain in the patient.

Example B18. The method of one or more of Examples B1-B17, wherein diagnostic accuracy from the MRI image of the patient is improved.

Example B19. The method of one or more of Examples B1-B18, wherein diagnosis of breast disease from the MRI image of the patient is improved.

Example B20. The method of one or more of Examples B1-B19, wherein there is no substantial impact on the hypothalamic-pituitary function of the patient.

Example B21. The method of one or more of Examples B1-B20, wherein there is no substantial impact on a serum FSH level and on a serum LH level of the patient.

Example B22. The method of one or more of Examples B1-B21, wherein the androgenic agent is a selective androgen receptor modulator.

Example B23. The method of Example B22, wherein the selective androgen receptor modulator is one or more of the following: (2S)-3-(4-cyanophenoxy)-N-[4-cyano-3-(trifluoromethyl)phenyl]-2-hydroxy-2-methylpropanamide, (7R,7aS)-2-Chloro-4-(7-hydroxy-1,3-dioxotetrahydropyrrolo[1,2-c]imidazol-2-yl)-3-methylbenzonitrile, 4-((R)-2-((R)-2,2,2-trifluoro-1-hydroxyethyl)pyrrolidin-1-yl)-2-trifluoromethyl)benzonitrile, 4-(3-Hydroxy-8-aza-bicyclo[3.2.1]octyl)-naphthalene-1-carbonitrile, JNJ-28330835, 6-(bis-(2,2,2-trifluoroethyl)amino)-4-trifluoromethyl-1H-quinolin-2-one, 9-chloro-2-ethyl-1-methyl-3-(2,2,2-trifluoroethyl)-3H-pyrrolo[3,2-f]quinolin-7(6H)-one, 2-[4-dimethylamino)-6-nitro-1,2,3,4-tetrahydroquinolin-2-yl]-2-methylpropan-1-ol, and (2S)—N-(4-cyano-3-trifluoromethylphenyl)-3-(3-fluoro-4-chlorophenoxy)-2-hydroxy-2-methyl-propanamide or derivatives thereof.

Example B24. The method of one or more of Examples B1-B23, wherein the androgenic agent is one or more of the following: testosterone, testosterone undecanoate, or methyltestosterone.

Example B25. The method of one or more of Examples B1-B24, wherein at least one of the patient's breasts has a VBD % of 7.5% or greater.

Example B27. The method of one or more of Examples B1-B26, wherein the patient is pre-menopausal, peri-menopausal or post-menopausal.

Example B28. The method of one or more of Examples B1-B27, wherein the method reduces VBD % and/or AVBD in at least one of the patient's breasts between one or more annual intervening mammographic detections.

Example B29. The method of one or more of Examples B1-B28, wherein the method reduces breast stiffness in at least one of the patient's breasts between one or more annual intervening mammographic detections.

Example B30. The method of one or more of Examples B1-B29, wherein the method reduces breast pain in at least one of the patient's breasts between one or more annual intervening mammographic detections.

Example B31. The method of one or more of Examples B1-B30, wherein the method reduce breast elasticity in at least one of the patient's breasts between one or more annual intervening mammographic detections.

Example B32. The method of one or more of Examples B1-B31, wherein the method decreases mechano-transduction on the genome of a cell in order to reduce the risk of malignant transformation in at least one of the patient's breasts between one or more annual intervening mammographic detections.

Example B33. The method of one or more of Examples B1-B32, wherein the method increases the ratio of fibroglandular and adipose tissue in at least one of the patient's breasts between one or more annual intervening mammographic detections.

Example B34. The method of one or more of Examples B1-B33, wherein the method increases CD36 in at least one of the patient's breasts between one or more annual intervening mammographic detections.

Example B35. The method of one or more of Examples B1-B34, wherein the method stabilizes and/or increases levels of androgen receptor expression in breast tissue in at least one of the patient's breasts between one or more annual intervening mammographic detections.

Example B36. The method of one or more of Examples B1-B35, wherein the method reduces and/or treats macromastia in at least one of the patient's breasts between one or more annual intervening mammographic detections.

Example B37. The method of one or more of Examples B1-B36, wherein the method increases GCDFP15 in the patient's breasts between one or more annual intervening mammographic detections.

Example B38. The method of one or more of Examples B1-B39, wherein the method reduces breast pain associated with having a mammography image taken in at least one of the patient's breasts between one or more annual intervening mammographic detections.

Example B39. The method of one or more of Examples B1-B38, wherein the method increases mammographic sensitivity in at least one of the patient's breasts between one or more annual intervening mammographic detections.

Example B40. The method of one or more of Examples B1-B39, wherein the method reduces VBD % in at least one of the patient's breasts by between 2% to 100%, 2% to 5%, 5% to 25%, or 25% to 100% over a 2 week, 3 month, 6 month, year, two year, three year or five year treatment period.

Example B41. The method of one or more of Examples B1-B40, wherein the method reduces VBD % in at least one of the patient's breasts by at least 20,%, 5%, 15% or 20% over a 2 week, 3 month, 6 month, one year, two year, three year or five year treatment period.

Example B42. The method of one or more of Examples B1-B41, wherein the method reduces AVBD in at least one of the patient's breasts by between 2% to 100%, 2% to 5%, 5% to 25%, or 25% to 100% over a 2 week, 3 month, 6 month, one year, two year, three year or five year treatment period.

Example B43. The method of one or more of Examples B1-B42, wherein the method reduces AVBD in at least one of the patient's breasts by at least least 2%, 5%, 15% or 20% over a 2 week, 3 month, 6 month, one year, two year, three year or five year treatment period.

Example B44. The method of one or more of Examples B1-B43, wherein the method reduces breast stiffness in at least one of the patient's breasts by between 5% to 100%, 5% to 20% or 20% to 50% over a 2 week, 3 month, 6 month, one year, two year, three year or five year treatment period.

Example B45. The method of one or more of Examples B1-B44, wherein the method reduces breast stiffness in at least one of the patient's breasts by at least 5%, 20%, 30% or 50% over a 2 week, 3 month, 6 month, one year, two year, three year or five year treatment period.

Example B46. The method of one or more of Examples B1-B45, wherein the method reduces breast pain in at least one of the patient's breasts by between 20% to 100%, 20% to 40%, or 40% to 80% over a 2 week, 3 month, 6 month, one year, two year, three year or five year treatment period.

Example B47. The method of one or more of Examples B1-B46, wherein the method reduces breast pain in at least one of the patient's breasts by at least 20%, 40% 50%, 60% or 70% over a 2 week, 3 month, 6 month, one year, two year, three year or five year treatment period.

Example B48. The method of one or more of Examples B1-B47, wherein the method reduces breast elasticity in at least one of the patient's breasts by between 10% to 100%, 10% to 30% or 30% to 60% over a 2 week, 3 month, 6 month, one year, two year, three year or five year treatment period.

Example B49. The method of one or more of Examples B1-B48, wherein the method reduces breast elasticity in at least one of the patient's breasts by at least 20%, 30% or 50% over a 2 week, 3 month, 6 month, one year, two year, three year or five year treatment period.

Example B50. The method of one or more of Examples B1-B49, wherein the method decreases mechano-transduction on the genome of a cell in order to reduce the risk of malignant transformation in at least one of the patient's breasts by between 10% to 100%, 10% to 30% or 30% to 60% over a 2 week, 3 month, 6 month, one year, two year, three year or five year treatment period.

Example B51. The method of one or more of Examples B1-B50, wherein the method decreases mechano-transduction on the genome of a cell in order to reduce the risk of malignant transformation in at least one of the patient's breasts by at least 20%, 30% or 50% over a 2 week, 3 month, 6 month, one year, two year, three year or five year treatment period.

Example B52. The method of one or more of Examples B1-B51, wherein the method increases the ratio of fibroglandular and adipose tissue in at least one of the patient's breasts by between 5% to 100%, 10% to 30% or 30% to 60% over a 2 week, 3 month, 6 month, one year, two year, three year or five year treatment period.

Example B53. The method of one or more of Examples B1-B52, wherein the method increases the ratio of fibroglandular and adipose tissue in at least one of the patient's breasts by at least 20%, 30% or 50% over a 2 week, 3 month, 6 month, one year, two year, three year or five year treatment period.

Example B54. The method of one or more of Examples B1-B43, wherein the method increases CD36 in at least one of the patient's breasts by between 5% to 100%, 10% to 30% or 30% to 60% over a 2 week, 3 month, 6 month, one year, two year, three year or five year treatment period.

Example B55. The method of one or more of Examples B1-B54, wherein the method increases CD36 in at least one of the patient's breasts by at least 20%, 30%, 40% or 60% over a 2 week, 3 month, 6 month, one year, two year, three year or five year treatment period.

Example B56. The method of one or more of Examples B1-B55, wherein the method stabilizes and/or increases levels of androgen receptor expression in breast tissue in at least one of the patient's breasts by between 5% to 100%, 10% to 30% or 30% to 60% over a 2 week, 3 month, 6 month, one year, two year, three year or five year treatment period.

Example B57. The method of one or more of Examples B1-B56, wherein the method stabilizes and/or increases levels of androgen receptor expression in breast tissue in at least one of the patient's breasts by at least 10%, 30%, 40% or 60% over a 2 week, 3 month, 6 month, one year, two year, three year or five year treatment period.

Example B58. The method of one or more of Examples B1-B57, wherein the method reduces macromastia in at least one of the patient's breasts by between 20% to 100%, 10% to 30% or 30% to 60% over a 2 week, 3 month, 6 month, one year, two year, three year or five year treatment period.

Example B59. The method of one or more of Examples B1-B58, wherein the method reduces macromastia in at least one of the patient's breasts by at least 20%, 30% or 50% over a 2 week, 3 month, 6 month, one year, two year, three year or five year treatment period.

Example B60. The method of one or more of Examples B1-B59, wherein the method increases GCDFP15 in the patient's breasts by between 20% to 100%, 10% to 30% or 30% to 60% over a 2 week, 3 month, 6 month, one year, two year, three year or five year treatment period.

Example B61. The method of one or more of Examples B1-B60, wherein the method increases GCDFP15 in the patient's breasts by at least 10%, 30%, 50% or 60% over a 2 week, 3 month, 6 month, one year, two year, three year or five year treatment period.

Example B62. The method of one or more of Examples B1-B61, wherein the method increases mammographic sensitivity in at least one of the patient's breasts by between 10% to 100% b, 10% to 30% or 30% to 60% over a 2 week, 3 month, 6 month, one year, two year, three year or five year treatment period.

Example B63. The method of one or more of Examples B1-B62, wherein the method increases mammographic sensitivity in at least one of the patient's breasts by at least 10%, 30% 50% or 60% over a 2 week, 3 month, 6 month, one year, two year, three year or five year treatment period.

Example B64. The method of one or more of Examples B1-B63, wherein the method reduces the treated patient's risk of developing breast cancer by at least 10%, 30% or 50% over a 2 week, 3 month, 6 month, one year, two year, three year or five year treatment period.

Example B65. The method of one or more of Examples B1-B64, wherein the method reduces the treated patient's risk of developing breast cancer between one or more annual intervening mammographic detections by at least 10%, 30% or 50% over a one year, two year, three year or five year treatment period.

Example B66. The method of one or more of Examples B1-B65, wherein the method improves breast compression during mammographic visualization of the breast by at least 10%, 30% or 50% over a 2 week, 3 month, 6 month, one year, two year, three year or five year treatment period.

Example B67. The method of Example B66, wherein the method decreases pain during mammographic visualization of the breast by at least 10%, 30% or 50% over a 2 week, 3 month, 6 month, one year, two year, three year or five year treatment period.

Example C1. A combination of an effective amount of an androgenic agent, and an effective amount of an aromatase inhibitor for use in a method for reducing VBD % and/or AVBD in a patient in need thereof, comprising administering of the combination to the patient.

Example C2. A combination of an effective amount of an androgenic agent, and an effective amount of an aromatase inhibitor for use in a method for reducing breast stiffness in a patient in need thereof, comprising administering of the combination to the patient.

Example C3. A combination of an effective amount of an androgenic agent, and an effective amount of an aromatase inhibitor for use in a method for reducing breast pain in a patient in need thereof, comprising administering of the combination to the patient.

Example C4. A combination of an effective amount of an androgenic agent, and an effective amount of an aromatase inhibitor for use in a method for reducing breast elasticity in a patient in need thereof, comprising administering of the combination to the patient.

Example C5. A combination of an effective amount of an androgenic agent, and an effective amount of an aromatase inhibitor for use in a method for decreasing mechano-transduction on the genome of a cell in order to reduce the risk of malignant transformation in a patient in need thereof, comprising administering of the combination to the patient.

Example C6. A combination of an effective amount of an androgenic agent, and an effective amount of an aromatase inhibitor for use in a method for increasing the ratio of fibro-glandular and adipose tissue in a patient in need thereof, comprising administering of the combination to the patient.

Example C7. A combination of an effective amount of an androgenic agent, and an effective amount of an aromatase inhibitor for use in a method for increasing CD36 in a patient in need thereof, comprising administering of the combination to the patient.

Example C8. A combination of an effective amount of an androgenic agent, and an effective amount of an aromatase inhibitor for use in a method for stabilizing and/or an increase in levels of androgen receptor expression in breast tissue in a patient in need thereof, comprising administering of the combination to the patient.

Example C9. A combination of an effective amount of an androgenic agent, and an effective amount of an aromatase inhibitor for use in a method for reducing and/or treating macromastia in a patient in need thereof, comprising administering of the combination to the patient.

Example C10. A combination of an effective amount of an androgenic agent, and an effective amount of an aromatase inhibitor for use in a method for increasing GCDFP15 in a patient in need thereof, comprising administering of the combination to the patient.

Example C11. A combination of an effective amount of an androgenic agent, and an effective amount of an aromatase inhibitor for use in a method for reducing breast pain associated with having a mammography image taken in a patient in need thereof, comprising administering of the combination to the patient.

Example C12. A combination of an effective amount of an androgenic agent, and an effective amount of an aromatase inhibitor for use in a method for increasing mammographic sensitivity in a patient, comprising administering of the combination to the patient.

Example C13. A combination of an effective amount of an androgenic agent, and an effective amount of an aromatase inhibitor for use in a method for reducing ABD % and/or AABD in a patient in need thereof, comprising administering of the combination to the patient.

Example C14. A combination of an effective amount of an androgenic agent, and an effective amount of an aromatase inhibitor for use in a method for reducing BPE in an MRI image of a patient, comprising administering of the combination to the patient.

Example C15. A combination of an effective amount of an androgenic agent, and an effective amount of an aromatase inhibitor for use in a method for reducing the size and/or quantity of cysts in a patient in need thereof, comprising administering of the combination to the patient.

Example C16. A combination of an effective amount of an androgenic agent, and an effective amount of an aromatase inhibitor for use in a method for reducing breast cancer in a patient in need thereof, comprising administering of the combination to the patient.

Example C17. The combination of one or more of Examples C1-C16, wherein there is a reduction in breast pain in the patient.

Example C18. The combination of one or more of Examples C1-C17, wherein diagnostic accuracy from the MRI image of the patient is improved.

Example C19. The combination of one or more of Examples C1-C18, wherein diagnosis of breast disease from the MRI image of the patient is improved.

Example C20. The combination of one or more of Examples C1-C19, wherein there is no substantial impact on the hypothalamic-pituitary function of the patient.

Example C21. The combination of one or more of Examples C1-C20, wherein there is no substantial impact on a serum FSH level and on a serum LH level of the patient.

Example C22. The combination of one or more of Examples C1-C21, wherein the androgenic agent is a selective androgen receptor modulator.

Example C23. The combination of one or more of Example C22, wherein the selective androgen receptor modulator is one or more of the following: (2S)-3-(4-cyanophenoxy)-N-[4-cyano-3-(trifluoromethyl)phenyl]-2-hydroxy-2-methylpropanamide, (7R,7aS)-2-Chloro-4-(7-hydroxy-1,3-dioxotetrahydropyrrolo[1,2-c]imidazol-2-yl)-3-methylbenzonitrile, 4-((R)-2-((R)-2,2,2-trifluoro-1-hydroxyethyl)pyrrolidin-1-yl)-2-trifluoromethyl) benzonitrile, 4-(3-Hydroxy-8-aza-bicyclo[3.2.1]octyl)-naphthalene-1-carbonitrile, JNJ-28330835, 6-(bis-(2,2,2-trifluoroethyl)amino)-4-trifluoromethyl-1H-quinolin-2-one, 9-chloro-2-ethyl-1-methyl-3-(2,2,2-trifluoroethyl)-3H-pyrrolo[3,2-f]quinolin-7(6H)-one, 2-[4-(dimethylamino)-6-nitro-1,2,3,4-tetrahydroquinolin-2-yl]-2-methylpropan-1-ol, and (2S)—N-(4-cyano-3-trifluoromethylphenyl)-3-(3-fluoro-4-chlorophenoxy)-2-hydroxy-2-methyl-propanamide or derivatives thereof.

Example C24. The combination of one or more of Examples C1-C23, wherein the androgenic agent is one or more of the following: testosterone, testosterone undecanoate, or methyltestosterone.

Example C25. The combination of one or more of Examples C1-C24, wherein at least one of the patient's breasts has a VBD % of 7.5% or greater.

Example C27. The combination of one or more of Examples C1-C26, wherein the patient is pre-menopausal, peri-menopausal or post-menopausal.

Example C28. The combination of one or more of Examples C1-C27, wherein the combination reduces VBD % and/or AVBD in at least one of the patient's breasts between one or more annual intervening mammographic detections.

Example C29. The combination of one or more of Examples C1-C28, wherein the combination reduces breast stiffness in at least one of the patient's breasts between one or more annual intervening mammographic detections.

Example C30. The combination of one or more of Examples C1-C29, wherein the combination reduces breast pain in at least one of the patient's breasts between one or more annual intervening mammographic detections.

Example C31. The combination of one or more of Examples C1-C30, wherein the combination reducing breast elasticity in at least one of the patient's breasts between one or more annual intervening mammographic detections.

Example C32. The combination of one or more of Examples C1-C31, wherein the combination decreases mechano-transduction on the genome of a cell in order to reduce the risk of malignant transformation in at least one of the patient's breasts between one or more annual intervening mammographic detections.

Example C33. The combination of one or more of Examples C1-C32, wherein the combination increasing the ratio of fibro-glandular and adipose tissue in at least one of the patient's breasts between one or more annual intervening mammographic detections.

Example C34. The combination of one or more of Examples C1-C33, wherein the combination increases CD36 in at least one of the patient's breasts between one or more annual intervening mammographic detections.

Example C35. The combination of one or more of Examples C1-C34, wherein the combination stabilizes and/or increases levels of androgen receptor expression in breast tissue in at least one of the patient's breasts between one or more annual intervening mammographic detections.

Example C36. The combination of one or more of Examples C1-C35, wherein the combination reduces and/or treats macromastia in at least one of the patient's breasts between one or more annual intervening mammographic detections.

Example C37. The combination of one or more of Examples C1-C36, wherein the combination increases GCDFP15 in the patient's breasts between one or more annual intervening mammographic detections.

Example C38. The combination of one or more of Examples C1-C39, wherein the combination reduces breast pain associated with having a mammography image taken in at least one of the patient's breasts between one or more annual intervening mammographic detections.

Example C39. The combination of one or more of Examples C1-C38, wherein the combination increases mammographic sensitivity in at least one of the patient's breasts between one or more annual intervening mammographic detections.

Example C40. The combination of one or more of Examples C1-C39, wherein the combination reduces VBD % in at least one of the patient's breasts by between 2% to 100%, 2% to 5%, 5% to 25%, or 25% to 100% over a 2 week, 3 month, 6 month, year, two year, three year or five year treatment period.

Example C41. The combination of one or more of Examples C1-C40, wherein the combination reduces VBD % in at least one of the patient's breasts by at least 2%, 5%, 15% or 20% over a 2 week, 3 month, 6 month, one year, two year, three year or five year treatment period.

Example C42. The combination of one or more of Examples C1-C41, wherein the combination reduces AVBD in at least one of the patient's breasts by between 2% to 100%, 2% to 5%, 5% to 25%, or 25% to 100% over a 2 week, 3 month, 6 month, one year, two year, three year or five year treatment period.

Example C43. The combination of one or more of Examples C1-C42, wherein the combination reduces AVBD in at least one of the patient's breasts by at least least 2%, 5%, 15% or 20% over a 2 week, 3 month, 6 month, one year, two year, three year or five year treatment period.

Example C44. The combination of one or more of Examples C1-C43, wherein the combination reduces breast stiffness in at least one of the patient's breasts by between 5% to 100%, 5% to 20% or 20% to 50% over a 2 week, 3 month, 6 month, one year, two year, three year or five year treatment period.

Example C45. The combination of one or more of Examples C1-C44, wherein the combination reduces breast stiffness in at least one of the patient's breasts by at least 5%, 20%, 30% or 50% over a 2 week, 3 month, 6 month, one year, two year, three year or five year treatment period.

Example C46. The combination of one or more of Examples C1-C45, wherein the combination reduces breast pain in at least one of the patient's breasts by between 20% to 100%, 20% to 40%, or 40% to 80% over a 2 week, 3 month, 6 month, one year, two year, three year or five year treatment period.

Example C47. The combination of one or more of Examples C1-C46, wherein the combination reduces breast pain in at least one of the patient's breasts by at least 20%, 40% 50%, 60% or 70% over a 2 week, 3 month, 6 month, one year, two year, three year or five year treatment period.

Example C48. The combination of one or more of Examples C1-C47, wherein the combination reducing breast elasticity in at least one of the patient's breasts by between 10% to 100%, 10% to 30% or 30% to 60% over a 2 week, 3 month, 6 month, one year, two year, three year or five year treatment period.

Example C49. The combination of one or more of Examples C1-C48, wherein the combination reducing breast elasticity in at least one of the patient's breasts by at least 20%, 30% or 50% over a 2 week, 3 month, 6 month, one year, two year, three year or five year treatment period.

Example C50. The combination of one or more of Examples C1-C49, wherein the combination decreases mechano-transduction on the genome of a cell in order to reduce the risk of malignant transformation in at least one of the patient's breasts by between 10% to 100%, 10% to 30% or 30% to 60% over a 2 week, 3 month, 6 month, one year, two year, three year or five year treatment period.

Example C51. The combination of one or more of Examples C1-C50, wherein the combination decreases mechano-transduction on the genome of a cell in order to reduce the risk of malignant transformation in at least one of the patient's breasts by at least 20%, 30% or 50% over a 2 week, 3 month, 6 month, one year, two year, three year or live year treatment period.

Example C52. The combination of one or more of Examples C1-C51, wherein the combination increasing the ratio of fibro-glandular and adipose tissue in at least one of the patient's breasts by between 5% to 100%, 10% to 30% or 30% to 60% over a 2 week, 3 month, 6 month, one year, two year, three year or five year treatment period.

Example C53. The combination of one or more of Examples C1-C52, wherein the combination increasing the ratio of fibro-glandular and adipose tissue in at least one of the patient's breasts by at least 20%, 30% or 50% over a 2 week, 3 month, 6 month, one year, two year, three year or five year treatment period.

Example C54. The combination of one or more of Examples C1-C43, wherein the combination increases CD36 in at least one of the patient's breasts by between 5% to 100%, 10% to 30% or 30% to 60% over a 2 week, 3 month, 6 month, one year, two year, three year or five year treatment period.

Example C55. The combination of one or more of Examples C1-C54, wherein the combination increases CD36 in at least one of the patient's breasts by at least 20%, 30%, 40% or 60% over a 2 week, 3 month, 6 month, one year, two year, three year or five year treatment period.

Example C56. The combination of one or more of Examples C1-C55, wherein the combination stabilizes and/or increases levels of androgen receptor expression in breast tissue in at least one of the patient's breasts by between 5% to 100%, 10% to 30% or 30% to 60% over a 2 week 3 month, 6 month, one year, two year, three year or five year treatment period.

Example C57. The combination of one or more of Examples C1-C56, wherein the combination stabilizes and/or increases levels of androgen receptor expression in breast tissue in at least one of the patient's breasts by at least 10%, 30%, 40% or 60% over a 2 week, 3 month, 6 month, one year, two year, three year or five year treatment period.

Example C58. The combination of one or more of Examples C1-C57, wherein the combination reduces macromastia in at least one of the patient's breasts by between 20% to 100%, 10% to 30% or 30% to 60% over a 2 week, 3 month, 6 month, one year, two year, three year or five year treatment period.

Example C59. The combination of one or more of Examples C1-C58, wherein the combination reduces macromastia in at least one of the patient's breasts by at least 20%, 30% or 50% over a 2 week, 3 month, 6 month, one year, two year, three year or five year treatment period.

Example C60. The combination of one or more of Examples C1-C59, wherein the combination increases GCDFP15 in the patient's breasts by between 20% to 100%, 10% to 30% or 30% to 60% over a 2 week, 3 month, 6 month, one year, two year, three year or five year treatment period.

Example C61. The combination of one or more of Examples C1-C60, wherein the combination increases GCDFP15 in the patient's breasts by at least 10%, 30%, 50% or 60% over a 2 week, 3 month, 6 month, one year, two year, three year or five year treatment period.

Example C62. The combination of one or more of Examples C1-C61, wherein the combination increases mammographic sensitivity in at least one of the patient's breasts by between 10% to 100%, 10% to 30% or 30% to 60% over a 2 week, 3 month, 6 month, one year, two year, three year or five year treatment period.

Example C63. The combination of one or more of Examples C1-C62, wherein the combination increases mammographic sensitivity in at least one of the patient's breasts by at least 10%, 30% 50% or 60% over a 2 week, 3 month, 6 month, one year, two year, three year or five year treatment period.

Example C64. The combination of one or more of Examples C1-C63, wherein the combination reduces the treated patient's risk of developing breast cancer by at least 10%, 30% or 50% over a 2 week, 3 month, 6 month, one year, two year, three year or five year treatment period.

Example C65. The combination of one or more of Examples C1-C64, wherein the combination reduces the treated patient's risk of developing breast cancer between one or more annual intervening mammographic detections by at least 10%, 30% or 50% over a one year, two year, three year or five year treatment period.

Example C66. The combination of one or more of Examples C1-C65, wherein the combination improves breast compression during mammographic visualization of the breast by at least 10%, 30% or 50% over a 2 week, 3 month, 6 month, one year, two year, three year or five year treatment period.

Example C67. The combination of one or more of Example C66, wherein the combination decreases pain during mammographic visualization of the breast by at least 10%, 30% or 50% over a 2 week, 3 month, 6 month, one year, two year, three year or five year treatment period.

Example C68. The combination of one or more of Examples C1-C67, wherein the combination reduces the risk of developing breast cancer in a patient.

Example D1. A combination of an effective amount of an androgenic agent, and an effective amount of an aromatase inhibitor for use in a method for reducing mammographic breast density and/or breast stiffness in a patient in need thereof, comprising administering of the combination to the patient.

Example D2. The combination of one Example D1, wherein the patient has a mammographic breast density of 7.5% or greater.

Example D3. The combination of one or more of Examples D1-D2, wherein the androgenic agent is a selective androgen receptor modulator.

Example D4. The combination of one or more of Examples D1-D3, wherein the patient is pre-menopausal, peri-menopausal or post-menopausal.

Example D5. The combination of one or more of Examples D1-D4, wherein the reduction in mammographic breast density is in the range of between 10% to 25% after 1 year, 2 years, 3 years, 4 years or 5 years of treatment.

Example D6. The combination of one or more of Examples D1-D5, wherein the breast stiffness reduces by at least 10% after 1 year, 2 years, 3 years, 4 years or 5 years of treatment.

Example D7. The combination of one or more of Examples D1-D6, wherein the androgenic agent is selected from the group consisting of testosterone, methyltestosterone, testosterone undecanoate, testosterone propionate, a selective androgen receptor modulator or combinations thereof.

Example D8. The combination of one or more of Examples D1-D7, wherein the method reduces the treated patient's risk of developing breast cancer between one or more annual intervening mammographic detections.

Example D9. The combination of one or more of Examples D1-D8, wherein the combination provides one or more of the following:
i) enhances mammographic detection due to reduced breast density enabling the mammogram to visualize malignancy at an earlier and/or less aggressive stage;
ii) enhances the ability to achieve better mammographic compression due at least in part due to reduced pain;
iii) enhances the ability to achieve better patient compliance in having regular mammographic check-ups;
iv) enhances the ability to treat the patient and at the same time not causing perturbations in the hypothalamic-pituitary axis and/or other endocrine axis;
v) reduces breast pain in a patient;
vi) reduces breast elasticity in a patient;
vii) decrease mechano-transduction on the genome of a cell in order to reduce the risk of malignant transformation in a patient;
viii) increases ratio of fibro-glandular and adipose tissue in a patient;
ix) increases CD36 in a patient;
x) stabilizes and/or an increase in levels of androgen receptor expression in breast tissue of a patient;
xi) increases the level of GCDFP15 in a patient;
xii) reduces BPE in an MRI image of a patient; and
xiii) reduces cysts in size and/or quantity in a patient's breast.

While certain embodiments have been shown and described herein, it will be obvious to those skilled in the art that such embodiments are provided by way of example only. It is intended that the following claims define the scope of the inventions and that methods and structures within the scope of these claims and their equivalents be covered thereby.

What is claimed is:

1. 1. A method of reducing background parenchymal enhancement (BPE) in a patient in need thereof, comprising administering to the patient:
   i) an effective amount of androgenic agent selected from the group consisting of testosterone, methyltestosterone, testosterone undecanoate, testosterone propionate, testosterone cypionate, and testosterone enanthate; and
   ii) an effective amount of an aromatase inhibitor selected from the group consisting of: exemestane, formestane, anastrozole, letrozole, vorozole, and fadrozole;
   wherein the method mitigates the treated patient's risk of developing breast cancer.

2. The method of claim 1, wherein the effective amount of androgenic agent is testosterone and the effective amount of the aromatase inhibitor is anastrozole and is administered by subcutaneous implant.

3. The method of claim 2, wherein:
   i) the effective amount of the testosterone is 2-200 mg; and
   ii) the effective amount of the anastrozole is 0.5-10 mg.

4. The method of claim 3, wherein the method improves breast compression during mammographic visualization or detection of the breast between one or more annual intervening mammographic detections.

5. The method of claim 3, wherein the method stabilizes and/or increases levels of androgen receptor expression in breast tissue in at least one of the patient's breasts between one or more annual intervening mammographic detections.

6. The method of claim 3, wherein the patient is pre-menopausal.

7. The method of claim 3, wherein the patient is peri-menopausal.

8. The method of claim 3, wherein the BPE reduces by at least 1 Breast Imaging-Reporting and Data System (BI-RADS®) level after 1 year, 2 years, 3 years, 4 years or 5 years of treatment.

9. The method of claim 8, wherein the BPE reduces by at least 2 BI-RADS® levels after 1 year, 2 years, 3 years, 4 years or 5 years of treatment.

* * * * *